US006993167B1

(12) United States Patent
Skladnev et al.

(10) Patent No.: US 6,993,167 B1
(45) Date of Patent: Jan. 31, 2006

(54) SYSTEM AND METHOD FOR EXAMINING, RECORDING AND ANALYZING DERMATOLOGICAL CONDITIONS

(75) Inventors: Victor Skladnev, Vaucluse (AU); Alex Gutenev, Dundas (AU); Scott Menzies, Sydney (AU); Richard Thompson, Killarney Heights (AU); Andrew Batrac, Dee Why (AU); Leanne Bischoff, Putney (AU); Roger Caffin, Berrilee (AU); Stephen Rowe, Blaxland (AU); Hugues Talbot, North Ryde (AU); David Varvel, Cherrybrook (AU); Peter West, Wahroonga (AU)

(73) Assignee: Polartechnics Limited, Sydney (AU)

( * ) Notice: Subject to any disclaimer, the term of this patent is extended or adjusted under 35 U.S.C. 154(b) by 0 days.

(21) Appl. No.: 09/473,270

(22) Filed: Dec. 27, 1999

Related U.S. Application Data

(60) Provisional application No. 60/165,072, filed on Nov. 12, 1999.

(51) Int. Cl.
*G06K 9/00* (2006.01)
(52) U.S. Cl. ...................................... 382/128; 600/160
(58) Field of Classification Search ................ 382/128; 600/175, 109, 160, 172, 200
See application file for complete search history.

(56) References Cited

U.S. PATENT DOCUMENTS

| 4,037,249 | A | 7/1977 | Pugsley ....................... 358/505 |
| 4,129,853 | A | 12/1978 | Althauser et al. ........... 382/273 |
| 4,170,987 | A | 10/1979 | Anselmo et al. .............. 600/75 |
| 4,314,281 | A | 2/1982 | Wiggins et al. ............. 358/406 |
| 4,315,309 | A | 2/1982 | Coli ................................ 705/3 |
| 4,602,291 | A | 7/1986 | Temes ......................... 348/243 |

(Continued)

FOREIGN PATENT DOCUMENTS

AU     38975/95 A    6/1996

(Continued)

OTHER PUBLICATIONS

Early detection of skin cancer: knowledge, perceptions and practices of general practitioners in Victoria, S Paine, J Cockburn, S Noy & R Marks, Med J Aust, 1994, 161, pp 188-195.

(Continued)

*Primary Examiner*—Jose L. Couso
*Assistant Examiner*—Tom Y. Lu
(74) *Attorney, Agent, or Firm*—Gottlieb Rackman & Reisman, PC

(57) ABSTRACT

A system for collecting, storing and displaying dermatological images for the purpose of monitoring and diagnosis of skin conditions and skin cancers, including melanoma. A hand-held unit illuminates a section of the patient's skin, and an imaging device generates imaging signals from light derived from a skin section. Pairs of light output ports in the hand-held unit are arranged such that their intensity distributions overlap at their half-intensity levels so that the resulting summation of their intensities has a flat central region. Three image stores are maintained, one for lesion images, one for "nearby skin" images, and one for reference-white images. The "nearby skin" images are used by the system software to automatically determine the skin/lesion border. The reference white images are used to set the dynamic range of the instrument and to compensate for lighting irregularities. Two images of the same lesion taken at different times may be displayed simultaneously so that changes in the lesion may be determined. The calibration system is designed so that image data taken on any of multiple machines built to the same specification will be corrected back to a common reference standard to ensure absolute accuracy in colour rendition.

50 Claims, 27 Drawing Sheets

U.S. PATENT DOCUMENTS

| | | | | |
|---|---|---|---|---|
| 4,704,029 | A | * 11/1987 | Van Heuvelen | 356/39 |
| 4,738,535 | A | 4/1988 | Webster | 356/418 |
| 4,846,184 | A | 7/1989 | Comment et al. | 600/306 |
| 4,905,702 | A | 3/1990 | Foss | 600/476 |
| 4,930,872 | A | 6/1990 | Convery | 359/896 |
| 4,947,245 | A | 8/1990 | Ogawa et al. | 348/66 |
| 4,970,598 | A | 11/1990 | Vogel | 358/461 |
| 5,016,173 | A | 5/1991 | Kenet et al. | 382/128 |
| 5,077,605 | A | 12/1991 | Ikeda et al. | 358/521 |
| 5,146,923 | A | 9/1992 | Dhawan | |
| 5,163,418 | A | * 11/1992 | Fraden et al. | 600/200 |
| 5,198,875 | A | 3/1993 | Bazin et al. | |
| 5,232,781 | A | * 8/1993 | Takemura et al. | 428/404 |
| 5,239,984 | A | 8/1993 | Cane et al. | 600/112 |
| 5,241,468 | A | 8/1993 | Kenet | 600/300 |
| 5,363,854 | A | 11/1994 | Martens et al. | 600/477 |
| 5,437,278 | A | 8/1995 | Wilk | 600/425 |
| 5,442,489 | A | 8/1995 | Yamamoto et al. | 359/810 |
| 5,463,497 | A | * 10/1995 | Muraki et al. | 359/618 |
| 5,527,261 | A | 6/1996 | Monroe et al. | 600/109 |
| 5,527,262 | A | 6/1996 | Monroe et al. | 600/110 |
| 5,662,586 | A | 9/1997 | Monroe et al. | 600/110 |
| 5,745,165 | A | 4/1998 | Atsuta et al. | 348/65 |
| 5,833,612 | A | 11/1998 | Eckhouse et al. | 600/476 |
| 5,836,872 | A | 11/1998 | Kenet et al. | 600/306 |
| 5,836,877 | A | 11/1998 | Zavislan | 600/407 |
| 5,852,494 | A | 12/1998 | Skladnev et al. | 358/243.1 |
| 6,010,450 | A | * 1/2000 | Perkins | 600/175 |
| 6,032,071 | A | * 2/2000 | Binder | 600/476 |
| 6,106,457 | A | * 8/2000 | Perkins et al. | 600/175 |
| 6,118,476 | A | 9/2000 | Morito et al. | |
| 6,208,749 | B1 | * 3/2001 | Gutkowicz-Krusin et al. | 382/128 |

FOREIGN PATENT DOCUMENTS

| | | |
|---|---|---|
| AU | 709459 | 8/1999 |
| JP | 10-333057 A | 12/1998 |
| WO | WO 90/13091 A | 11/1990 |
| WO | 9605489 | 2/1996 |
| WO | 9905961 | 2/1996 |
| WO | 9616698 | 6/1996 |
| WO | 9747235 | 12/1997 |
| WO | 9837811 | 9/1998 |

OTHER PUBLICATIONS

General practitioner and patient response during a public education program to encourage skin examinations, J Lowe, K Balanda, C Mar, D Purdie & A Hilsdon, Med J Aust, 1994, 161, pp 195-198.

Unsupervised Color Image Segmentation, with application to skin tumor borders, G A Hance, S E Umbaugh, R H Moss, W V Stoeker, IEEE Eng in Med & Biol, Jan./Feb. 1996, pp104-111.

A possible new tool for clinical diagnosis of melanoma: the computer, N Cascinelli, M Ferrario, T Tonelli, E Leo, J Am Acad Dermat, Feb. 1987, 16/2 pt 1, pp361-367.

Computer image analysis in the diagnosis of melanoma, A Green, N Martin, J Pfitzner, M O'Rourke, N Knight, J Am Acad Dermat, 1994; 31, pp 958-964.

Computer screening for early detection of melanoma—is there a future?, P N Hall, E Claridge, J D Morris Smith, Brit J Dermatology, Mar., 1995, 132/3, pp 325-38.

Early diagnosis of melanoma using image analysis techniques, V Ng, A J Coldman, Melanoma Research, 1993, 3, p81.

Automated Instrumentation for the Diagnosis of Invasive Melanoma: Image Analysis of Oil Epiluminescence Microscopy, Menzies, et al., Skin Cancer and UV Radiation, Springer Verlag, 1997.

A television method for measuring infrared and ultraviolet reflectances of pigmented lesions, R J Marshall, J Audiovisual Media in Medicine, 1982, 5, pp 51-55.

Reliability of Computer Image Analysis of Pigmented Skin lesions of Australian Adolescents, J F Aitken, J Pfitzner, D Battistutta, P K O'Rourke, A C Green & N G Martin, Cancer, 1996; 78, pp 252-257.

In vivo epiluminescence microscopy of pigmented skin lesions, II: diagnosis of small pigmented skin lesions and early detection of malignant melamona, A Steiner, H Pehamberger, K Wolff, Am Acad Dermat, 1987, 17, pp 584-591.

Clinical Diagnosis of Pigmented Lesions using Digital Epiluminescence Microscopy: Grading Protocol and Atlas, Kenet R O, Kang S, Kenet B J, Fitzpatrick T B, Sober A J, Barnkill R L, Arch Derm, Feb. 1993, pp 157-174.

Computerized evaluation of pigmented skin lesion images recorded by a video microscope: comparison between polarizing mode observation and oil/slide mode observation, S Seidenari, M Burroni, G Dell'Eva, P Pepe, B Belletti, Skin Research and Technology, 1995,1, pp 187-191.

Generalized Inverse Methods for the Best Leastsquares Solution of Systems of Non-linear Equations, R Fletcher, Computer J, 10, pp392-399.

GINV, A Subroutine in ANSI Fortran for Generalized Matrix Inversion, H W Holdaway, Australian Computer J, 9/4, Nov. 1977.

Shape Analysis For Classification Of Malignant Melanoma, Claridge, et al., J Biomed Eng, vol. 14, pp. 229-234.

The ABCD Rule Of Dermascopy, Nachtbar, et al., J Am Acad Dermat, Apr. 1994, pp. 551-559.

Melanocytic Lesions Excised From The Skin: What Percentage Are Malignant? Del-Mar, et al., Aust J Public Health, vol. 18, pp. 221-223.

Skin Surface Microscopy, Stoltz, et al., Lancet, vol. 2, 1989, pp. 864-865.

Computer image analysis of pigmented skin lesions, Melanoma Research, vol. 1, 1991, pp. 231-236.

An Automated Melanoma Diagnosis System, New Approaches in Medical Image Analysis, edited by B. Pham, M. Braun, A. J. Maeder, M. P. Eckert, SPIE Proceedings, 1999.

* cited by examiner

SYSTEM AND METHOD FOR EXAMINING, RECORDING AND ANALYZING DERMATOLOGICAL CONDITIONS

This application claims the benefit of U.S. provisional application No. 60/165,072, filed on Nov. 12, 1999.

FIELD OF THE INVENTION

This invention relates to an integrated system for the acquisition of high quality medical images of skin, the storage and archiving of those images, the analyses of those images in a patient-oriented database, and the subsequent retrieval of those images and their analyses, and more particularly to such a system for use in the monitoring and diagnosis of skin conditions and skin cancers, including melanoma.

BACKGROUND OF THE INVENTION

Malignant melanoma is a form of cancer due to the uncontrolled growth of melanocytic cells just under the surface of the skin. These pigmented cells are responsible for the brown colour in skin and freckles. Malignant melanoma is one of the most aggressive forms of cancer known. The interval between a melanoma site becoming malignant or active and the probable death of the patient in the absence of treatment may be short, of the order of only six months. Death occurs due to the spread of the malignant melanoma cells beyond the original site through the blood stream into other parts of the body. Early diagnosis and treatment is essential for a favourable prognosis.

However, the majority of medical practitioners are not experts in the area of dermatology and each one might see only a few melanoma lesions in a year. In consequence, the ordinary medical practitioner has difficulty in assessing a lesion properly. (See, e.g., *Early Detection of Skin Cancer: Knowledge, Perceptions and Practices of General Practitioners in Victoria*, Paine, et al., Med J Aust, vol. 161, pp. 188–195, 1994, and *General Practitioner and Patient Response During a Public Education Program to Encourage Skin Examinations*, Lowe, et al., Med J Aust, vol 161, pp. 195–198, 1994). There is therefore a strong tendency for the ordinary medical practitioner to remove a lesion if it is at all suspect for the purpose of obtaining a histopathological diagnosis.

Medical statistics show that this tendency means that malignant melanomas form a very small fraction of the lesions being surgically excised, with the rest being harmless. A figure of 3% has been quoted by one authority (see *Melanocytic Lesions Excised from the Skin: What Percentage are Malignant?*, Del-Mar, et al., Aust J Public Health, vol 18, pp. 221–223). This excess of surgical procedures leads to significant wasted expense to the community, and risks of scarring and infection. Most of these problems could be avoided if the ordinary medical practitioner had access to the knowledge of the expert dermatologist. A significant improvement in diagnosis would come from encapsulating the expert knowledge of a skilled dermatologist and making this knowledge more widely available.

Examination of skin lesions and the identification of skin cancers such as melanoma have traditionally been done with the naked eye. More recently dermatologists have used a hand-held optical magnification device generally known as a dermatoscope (or Episcope) (see, e.g., *Skin surface microscopy*, Stoltz et al., Lancet vol. 2, pp. 864–5, 1989). In essence, this device consists of a source of light to illuminate the area under examination and a lens or combination of lenses for magnifying the area of skin under examination. Typically, this instrument has a flat glass window at the front which is pressed against the skin in order to flatten the skin and maximise the area in focus. The physician-user looks through the instrument to see a magnified and illuminated image of the lesion. An expert dermatologist can identify over 70 different morphological characteristics of a pigmented lesion. (See, e.g., *Automated Instrumentation for the Diagnosis of Invasive Melanoma: Image Analysis of Oil Epiluminescence Microscopy*, Menzies, et al., Skin Cancer and UV Radiation, Springer Verlag, 1997.) These instruments are now available commercially (see, e.g., the Episcope™ by Welch-Allyn, Inc., 4341 State Street Rd, Skaneateles Falls, N.Y. 13153-0220).

The dermatoscope is used with an index matching medium, usually mineral oil between the window and the patient's skin. The purpose of the "index matching oil" is to eliminate reflected light due to the mismatch in refractive index between skin and air. Reflected light contains little information about the skin. Information about the skin and the sub-surface melanoma cells is contained in the reradiated light. By limiting the light reaching the observer to just reradiated light, the best possible image of the medically important sub-surface details is obtained. The user sees more of that part of the skin where the malignant melanoma cells are initially located. This method is known as epiluminescence microscopy or ELM. (See, e.g., *In Vivo Epiluminescence Microscopy of Pigmented Skin Lesions, II: Diagnosis of Small Pigmented Skin Lesions and Early Detection of Malignant Melanoma*, Steiner, et al., Am Acad. Dermat, 1987, vol. 17, pp. 584–591; *Trends in Dermatology: Differential Diagnosis of Pigmented Lesions Using Epiluminescence Microscopy*, in Sober et al., eds, 1992 Year Book of Dermatology, St Louis, Mo.; *Clinical Diagnosis of Pigmented Lesions Using Digital Epiluminescence Microscopy: Grading Protocol and Atlas*, Kenet et al., Arch. Derm, February 1993, pp. 157–174; and U.S. Pat. No. 5,836,872 in the name of Kenet et al.).

Polarised light may also be used for the purpose of eliminating reflections, and its use is well known in the scientific and medical literature (for medical examples in this area see, e.g., *Computerised evaluation of pigmented skin lesion images recorded by a video microscope: comparison between polarising mode observation and oil/slide mode observation*, Seidenari et al., Skin Research and Technology, pp. 187–191, 1995 and publication WO 96/16698). The use of polarised light in this context has been shown to produce lower contrast inside the lesion borders than are observed with ELM.

We have found that due to total internal reflection (TIR) in the glass window, ELM images are subject to a self-illuminating effect. The perceived brightness of the object can increase almost twofold when the brightness of the background increases. The effect is independent for each colour channel which makes colour of the object depend on the colour of the background. This introduces errors into colour analysis of the ELM images as well as reduces the image contrast.

In view of the complications introduced by the use of a window, the advantages of designing the system without a window have been considered. Two approaches are possible—either a cone may be placed on the camera and used without a window, or the camera may be operated without any sort of cone whatsoever. The second approach is shown in publication WO 97/47235. The absence of a cone means that the image scale is essentially uncontrolled.

The influence of unknown external lighting prevents the production of an image which is colour-calibrated across its whole region. Use of a cone without a window is shown in U.S. Pat. No. 4,930,872. It proves to have a significant disadvantage, in that the unsupported skin is allowed to bulge inwards towards the camera. This means that any optical system involving lenses must cope with a significant depth of focus, which requires a smaller aperture and hence a higher level of illumination than would otherwise be needed. It also means that the shape of the lesion may vary from inspection to inspection due to varying amounts of bulge, and the colour appearance of the lesion will vary due to the varying angle the lesion surface presents to the observer. This bulge may be reduced by reducing the unsupported area, but this is not a realistic approach with a large lesion.

Some dermatologists have used film-based cameras to photograph skin lesions, both as a way of magnifying the image of the lesion and as a way of recording the image. However, skill is required in using such photographs as the repeatability of the images and hence the range of recognisable features can be affected by a range of factors in the photographic process. Attempts have been made to convert these photographic images to digital form and to locate the skin lesion border (see, e.g., *Unsupervised Colour Image Segmentation, with Application to Skin Tumor Borders*, Hance, et al., IEEE Eng in Med & Biol, January/February 1996, pp. 104–111). Attempts in this direction have highlighted the fact that a skilled dermatologist sees and uses detail in the image down to a very small size, meaning that both high quality colour and high resolution imaging is required for this task.

A number of other medical instruments exist for the direct illuminated optical inspection of parts of the human body, e.g., the opthalmoscope and the otoscope. In these instruments, a miniature TV camera is added to a standard medical instrument or even substituted for the user's eyes. This has created a range of video microscopes of various forms (see, e.g., U.S. Pat. No. 4,905,702 in the name of Foss, U.S. Pat. No. 4,930,872 in the name of Convery, U.S. Pat. No. 4,947,245 in the name of Ogawa, et al., U.S. Pat. No. 5,363,854 in the name of Martens et al., U.S. Pat. No. 5,442,489 in the name of Yamamoto et al., U.S. Pat. No. 5,527,261 in the name of Monroe et al., U.S. Pat. No. 5,662,586 in the name of Monroe et al., U.S. Pat. No. 5,745,165 in the name of Atsuta et al., U.S. Pat. No. 5,836,872 in the name of Kenet et al., publication WO 96/16698 in the name of Binder and publication WO 98/37811 in the name of Gutkowicz-Krusin et al.). It is also known to save such images of the skin in a computer database (see, e.g., U.S. Pat. No. 4,315,309 in the name of Coli and U.S. Pat. No. 5,016,173 in the name of Kenet, et al.), although computer databases came into existence with the first computers, and medical researchers have in fact been using computers for many years to store and analyse digital images of melanoma lesions (see, e.g., *A Possible New Tool for Clinical Diagnosis of Melanoma: the Computer,* Cascinelli, et al., J Am Acad Dermat, 1987, February, vol. 16/2 pt 1, pp. 361–367).

It is known that a melanoma lesion will have a complex geometry and this may serve as an indication of malignant melanoma (see, e.g., *Shape analysis for classification of malignant melanoma*, Claridge et al., J Biomed Eng, vol. 14, pp. 229–234, 1992). However, the complexity of a lesion makes the identification of even the boundaries between the lesion and the surrounding skin difficult. (See, e.g., *Unsupervised Color Image Segmentation with Application to Skin Tumor Borders*, Hance, et al., IEEE Eng in Med and Biol, January/February 1996, pp. 104–111.) This problem is compounded by the obvious fact that human skin colour is widely variable between different individuals and across different races. It is also found that skin colour can vary significantly across the body on any individual, due to effects such as sun tan, skin thickness and capillary density. Thus it is not possible to specify any particular colour as being "always skin".

Identification of the fine details within a lesion by computer image analysis of directly recorded colour video images is a problem whose solution has been attempted by some researchers (see, e.g., Computer image analysis of pigmented skin lesions, Green et al., Melanoma Research, vol. 1, pp. 231–6, 1991, and *Computer Image Analysis in the Diagnosis of Melanoma*, Green, et al., J Am Acad Dermat, 1994, vol. 31, pp. 958–964) but with limited success. Some work has been done with medium resolution grey-scale images but mainly with the borders of the lesion. (See, e.g., *Early Diagnosis of Melanoma using Image Analysis Techniques*, Ng, et al., Melanoma Research, 1993, vol. 3, p. 81). It is generally true that the specification and measurement of lesion geometries has not been achieved in a systematic and reproducible manner suitable for widespread use, although descriptive broad rules have been developed and are generally accepted as being useful (see, e.g., *The ABCD rule of dermatoscopy*, Nachtbar et al., J Am Acad Dermat., pp. 551–59, April 1994).

The analysis problem is compounded by the fact that the resolution of the images taken with common single-CCD miniature colour TV cameras is not very high (typically, poorer than 0.1 mm on the lesion with a 25 mm field of view), which limits the ability to discriminate fine detail during either on-screen inspection or software-driven image analysis of geometrical features. Such cameras are used in both publication WO 96/16698 and U.S. Pat. No. 4,930,872. Resolution of fine colour detail requires the use of high performance TV cameras such as the type known in the industry as "3-CCD". Full use of such cameras also requires the use of a lens of matching quality. The alternate approach to the generation of high resolution colour images is to use a high resolution monochrome camera, sequentially illuminate the skin area of interest with light in three different colour bands such as red, green and blue, and to take an image under each colour of illumination. Such coloured light may be generated from white light with a set of filters in the illumination path. This generates essentially the same red/green/blue (RGB) set of colour images as is obtained from a 3-CCD camera, and is used in publication WO 98/37811. However, this technique suffers from a disadvantage in comparison to the use of a 3-CCD camera. The process of changing filters takes time, and this permits movement of the skin area of interest during the process. Should this happen there would be a loss of colour registration within the composite image. Times of up to three minutes are quoted in publication WO 98/37811. This problem is exacerbated by the use of an index matching oil between the skin and the front window since such oil serves as a lubricant. The problem may be reduced by applying pressure between the window and the skin, but this compresses the skin, excludes blood from the underlying dermal layers and changes the skin colour in an unacceptable manner. This whole problem may be largely eliminated by using a high resolution 3-CCD camera with a fast exposure.

It is also known that a melanoma will feature a range of colours with the range being created by the depth of pigment within the lesion. This is illustrated in *An Atlas of Surface*

*Microscopy of Pigmented Skin Lesions*, Menzies et al., McGraw-Hill, Sydney, 1996. These colours are typically classified by expert dermatologists with a small set of common names such as light brown, dark red, black, etc. Some attempts have been made to measure these colours. (See, e.g., Marshall op cit). However, the specification and the measurement of these colours has not been achieved in a systematic and reproducible manner, with current research publications still focusing on very simple measurements of lesion colour. (See, e.g., *Reliability of Computer Image Analysis of Pigmented Skin lesions of Australian Adolescents*, Aitken, et al., Cancer, 1996, vol. 78, pp. 252–257). The ordinary medical practitioner does not have sufficiently frequent contact with malignant melanomas to retain familiarity with these colours. An added complication lies in the way a typical colour TV-based image analysis system measures colour using red, green and blue channels, each measured nominally to 1 part in 256. Typically, there is the potential for up to 16 million different colours ($256^3$) to be recorded. To allow any sort of analysis it is necessary to condense this enormous range down to a small number of medically significant colours. This is done by a process commonly known as colour binning. In this process, all colours within a certain range are given one name, such as red or brown. Defining the boundaries of these bins in a useful manner is a difficult task. It also requires that the imaging system be colour stable.

The system shown in publication WO 96/16698 reduces the image intensity to shades of grey but does not provide colour binning. Since a skilled dermatologist relies heavily on the range of colours present in forming a diagnosis, this approach is not adequate. Furthermore, it is done in an ad hoc manner as the system does not provide any stability in either illumination intensity or illumination colour temperature (lamp brightness can be varied by the user at will). Hance et al. (op cit) were only able to reduce images to skin plus 2 (or 3 in one case) lesion colours. Again, there was no attempt to stabilise the illumination.

It may therefore be seen that some form of stabilisation of the illumination is essential. This may be done in two main ways—by driving the illuminator with a stable source of power or by feedback. The latter may be done by sensing the lamp brightness in standard ways, and is used in U.S. Pat. No. 4,930,872, although it has been found that a stable voltage source driving a high quality quartz iodine (QI) lamp provides basic stability. However, further compensation for brightness variations both in time and across the image may still be required to ensure that each individual image can be appropriately calibrated to an international colour standard.

Given that a high stability illumination field has been generated, that provision has been made for monitoring it over time, and that a high resolution 3-CCD camera and lens is used to take images rapidly to avoid colour registration problems, compensation may then be profitably applied to correct for any other imaging problems encountered.

As mentioned above, a significant problem not previously reported which may be encountered with the use of ELM is a variation in apparent image brightness and colour due to total internal reflection in the window otherwise used to keep the skin flat. Prior art calibration means and techniques, e.g., as disclosed in publication WO 98/37811, virtually ignored the existence of the glass surface adjacent to the skin by putting the reference strip of diffusely reflecting grey material on the observer side of the glass surface.

SUMMARY OF THE INVENTION

Being able to image a suspect lesion to high resolution and with high colour stability and to analyse it for features which a dermatologist would identify as significant would be very helpful to the general practitioner. Such analysis, performed by image analysis software using known methods of assessing shape and texture, and by using research information about the characteristics of such lesions obtained by research involving expert dermatologists and scientists skilled in the art of image analysis, is facilitated by the present invention, but such analysis per se, except in regard to certain features which by themselves do not allow full diagnosis, does not form part of the invention. The desirability and possibility of such automatic analysis has already been pointed out, as outlined in Cascinelli et al., op cit, and *Computer Screening for Early Detection of Melanoma—is there a Future?*, Hall, et al., Brit J Derm, May 1995, vol. 132/3, pp. 325–38, But before automatic analysis can be performed, there is an infrastructure that must be in place. The subject invention concerns primarily that infrastructure—an integrated system for the acquisition of high quality medical images of skin, the calibration of these images to international colour standards the storage and archiving of those images, the limited analyses of those images in a patient-oriented database, and the subsequent retrieval of those images and their analyses.

The hardware of the invention consists of an image capture device, such as a video camera or digital still camera, in a hand-held unit that can be brought to the patient, and a light source either within the hand-held unit or remotely located that includes optics such as a bundle of optical fibres for conveying light to the hand-held unit to illuminate the area to be imaged. The illumination system is designed to produce a very even and stable illumination to permit calibrated assessment of the colours in a lesion. Means are provided for calibrating the imaging system and for ensuring the system remains within calibration. These include the provision of a special reference white material for recording and checking the illumination field before skin and lesion images are recorded, compensation targets located within the field of view of the camera, and software for the correction of spatial or temporal deviations in the illumination field. Reference is made in some of the above cited patents to the need for a uniform illumination field but, apart from mentioning the use of a fibre optic ring light, none of them give any details on how this might be achieved.

A range of imaging devices may be used, from video cameras giving images in real-time to digital still cameras with slower responses. In all cases, the lighting has to be carefully controlled to allow colour calibration across the whole image. Thus while lighting mechanisms and image acquisition may vary, all must provide a colour-calibrated image suitable for subsequent analysis.

The images may be transferred to a computer for subsequent analysis and storage either immediately, as with a video connection from a video camera into a frame grabber located within the computer, or later, via either some form of direct link between the camera and the computer or indirectly via some form of image file transfer such as memory chip, magnetic or optical disk copying, modem file transfer or otherwise.

The software system controls the acquisition of images; calibration of the system and checking the calibration of the system; handling the entry and storage of all patient details, all lesion details, and all images; the analysis of the images using image analysis techniques for a range of features including those which might be used by an expert dermatologist but also including other features that may be found from further research to be medically significant; and the routine management (backup, archiving and restoring) of the image and data files resulting from the use of the system in a medical practice. A graphical screen-oriented or Windows-style user interface is employed, although it is not essential.

The first stage of any automatic skin analysis requires distinction between skin and lesion. This distinction is rendered difficult in practice by the variability in skin colour for any one patient. As noted above, previous attempts to do this automatically gave poor results as it was difficult to give general rules about the colour of skin and the distinction from lesion colour. (See, e.g., *Unsupervised Color Image Segmentation with application to skin tumor borders*, Hance, et al., IEEE Eng in Med and Biol, January/February 1996, pp. 104–111). The system shown in publication WO 96/16698 has an option to determine the threshold automatically using information from the red and green channels of the TV image of the lesion, but this proves in practice to be not very successful. This is to be expected given the absence of stable illumination in the design. The system shown in publication WO 98/37811 claims automatic segmentation between skin and lesion using the blue channel of the TV image of the lesion, but this too would be limited by the unknown (to the computer) skin colour and variability in skin colour. The system shown in publication WO 96/16698 also permits manual identification of the boundary between skin and lesion by the user, as a series of points on the image, but experience has shown that this too has significant problems and sometimes fails. Accordingly, in our invention one or more images of lesion-free skin adjacent to the lesion are recorded in order to provide information to assist in the automatic discrimination between the lesion and skin.

One indication of a malignant melanoma is that the area and shape of the lesion changes within a period of several months. Considerable benefit would accrue to the medical practitioner and the patient were it possible to objectively compare the state of the lesion at different times, for example, at monthly intervals. Other features on the skin may also be of concern such that it is desirable to track them over time in a similar manner. It is therefore another object of our invention to allow the medical practitioner to capture and record images of suspect lesions and other skin features for each patient in such a manner that both the images, and the associated data and analyses, can be retrieved later for examination or comparison with new images and new analyses. This comparison can be done manually by the physician or automatically by the system software, by means of a monitoring report. This object goes beyond the detection of skin cancer and can be used to monitor changes in any skin condition that has been imaged. Prior art already exists in this medical database area. (See, e.g., U.S. Pat. No. 5,016,173, and Cascinelli, 1987, op cit.) In our invention, provision is made for manual or automatic comparisons of images of a single lesion over time and for distinguishing between several lesions in close proximity.

A patient may often have lesions or other features on several positions on his or her body, or may have several lesions close together on one area of the body. Our invention provides for separately identifying the different lesions or feature positions on the patient's body, tracking which images and associated data are associated with which positions on the patient, and the dates when those images were taken. Should an analysis be done on an image, the results of that analysis may optionally also be included in the associated data. More specifically, provision is made in our invention to record the position of a lesion image with respect to the patient body. This may be done in either of two ways: on a default generic "bodymap" image, showing multiple views of the different sides of a human body at various magnifications, and on "photomaps". These latter are images taken of a substantial area of the patient body, such as one shoulder. A photomap may be used to handle situations where several lesions are found in close proximity, such that they could not be distinguished on the default bodymap. Where only a single lesion exists in a reasonable area, the location of the lesion with respect to parts of the body as shown on the default bodymap is sufficient. Where confusion might arise, the existence of and the position of a photomap is recorded on the default bodymap, and the position of the lesions are then recorded on the photomap. A "tree structure" of images is thereby maintained. Our invention allows for the lesion data to be made available directly through accessing the lesion location marker on the generic bodymap, or the alternate photomap or photomaps.

Our invention provides for routine data backup and long term archiving of patient information and images. This includes assisting in the retrieval of images and associated data from backups and archives.

Our research has shown that the illumination field may still be upset by the phenomenon of total internal reflection (TIR) within the front window. The presence of oil between the skin and the window optically couples the surface of the glass adjacent to the skin with the skin surface. This allows the re-radiated light from an arbitrary spot on the skin within the area, illuminated by the light source, to enter the window at a low angle to the surfaces of the window. This angle can be low enough for such light to suffer total internal reflection from other surfaces (edge and surface close to the viewer) of the glass window and be cast back onto the skin surface some distance away from the source spot (FIG. 26). Thus the colour of one oil-immersed area of the skin may alter the illumination reaching another area. It should be noted that the area immediately adjacent to the spot gets virtually none of this secondary illumination but gets the illumination from spots further away. This leads to a visual change in skin brightness and tinge depending on the presence of dark objects (lesions) within the field of view. It should be noted that the change in brightness of the background from black to white can amount to as much as a doubling of an object's observed intensity.

The geometrical analysis of the TIR phenomenon shows that the image self-illuminating effect depends on the glass thickness. The thinner the glass the more localised is the effect and less light is contributed from the picture elements (pixels) distant to a given pixel. For 0.1 mm glass, it manifests itself in visible smoothing of sharp dark-to-bright transitions within the image. On the other hand, thicker glass results in larger amounts of smaller contributions from pixels distant from a given one. As a result, each pixel of the image gets approximately the same amount of TIR light from the whole illuminated area. The variation in lighting due to TIR can be measured in this case by small areas of known colour located within the field of view on the side of the glass adjacent to the image object. Any small deviations from nominal in the colour of these targets may be interpolated across the image and suitable corrections applied to bring the targets back to nominal. This reduces the colour shift induced by the total internal reflection to the noise level of the image capture device.

Thus means of counteracting the TIR effect include: a thick front window material, rendering of the front window edges absorptive and non-radiating to minimise edge contribution to the TIR effect, and at least one colour/grey scale target on the surface of the window that makes contact with the image object to allow the TIR effect to be quantified and compensated.

OBJECTS OF THE INVENTION

Some of the objects of the invention include the following:

- To provide high quality stable colour images of small areas of skin as might be covered by a melanoma lesion or some other skin condition, at a known and fixed scale;
- To assist the image analysis process of automatically identifying the boundary between clean skin and lesion by providing for each lesion or group of lesions one or more images of adjacent clean skin, to the same scale as that of the lesion image, for use as a statistical skin colour reference;
- To provide images ("photomaps") of larger areas of the body, which images are not of the same high stability in colour, such as might illustrate where a particular lesion or skin condition is located, or to allow the physician to discriminate between several lesions in close proximity (these photomap images to be in addition to a default bodymap or generic graphic image of a human body and with the photomap positions identified on that default bodymap);
- To associate the images of lesions with the photomap images of larger areas of the body featuring those lesions, in order to assist the user to locate a particular lesion at a later time or date;
- To provide illumination to the imaged area of high temporal stability and spatial uniformity, such that the images of small areas may be calibrated to international colour metrology standards, and different machines of the invention will give substantially identical colour measurements on the same skin sample or lesion;
- To correct small spatial or temporal variations in the lighting and camera response of any system for small area images to further enhance and maintain calibration to international colour metrology standards during use, and so that different machines will give substantially identical colour measurements of the same lesion;
- To monitor the calibration of the system to international colour metrology standards in every small area image of skin or a lesion, allowing users of different machines to confirm that their machines remain within calibration and will give substantially identical colour measurements of the same lesion;
- To minimise optical effects found when imaging through a transparent window in optical contact with the surface being studied;
- To provide further monitoring and compensation for the optical effects found when imaging through a transparent window in optical contact with the surface being studied in order to maintain colour measurement precision;
- To provide small area images of high resolution in all colour channels to permit detailed image analysis of the coloured boundary and internal geometrical structures of a lesion in order to identify features normally recognised by the expert dermatologist as being medically significant;
- To facilitate automatically (by software) identifying the boundary between clean skin and lesion with accuracy, that is, given information about what clean skin should look like, distinguish between clean skin and a lesion;
- To reduce the full range of colours registered by the imaging system to a small medically significant range of colours to facilitate the provision of diagnostic information to a physician;
- To provide storage for all images and all information associated with the images, including the positions of the image areas on the body and any results from the image analysis for a particular patient, in such a manner that the images may be retrieved at a later time or date and each lesion image is again associated with the correct lesion on the patient; and
- To allow a person not skilled in computer database management to operate an integrated system for the back-up, archiving, storage and tracking of patient images and records.

DESCRIPTION OF THE DRAWINGS

Further objects, features and advantages will become apparent upon consideration of the following detailed description in conjunction with the drawings, in which.

DETAILED DESCRIPTION OF THE ILLUSTRATIVE EMBODIMENT

Figure 1:
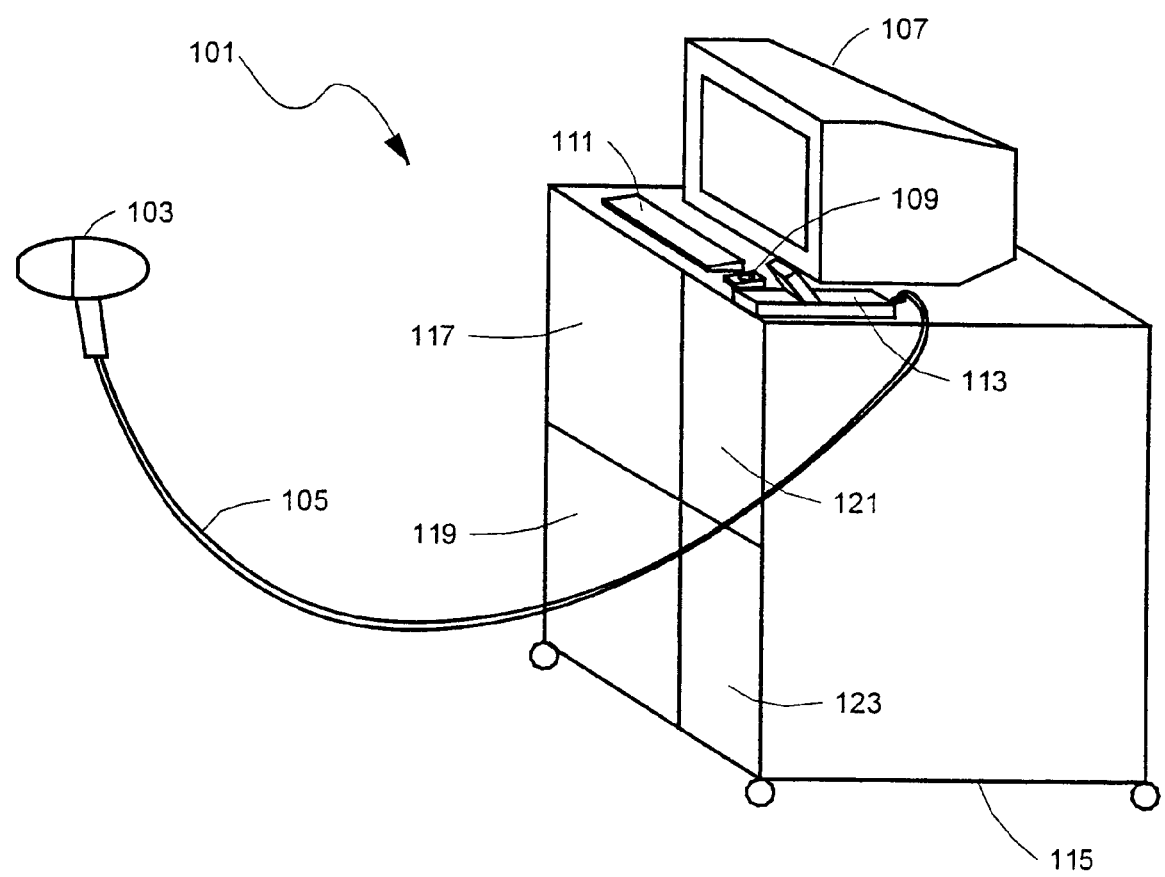
FIG. 1 is a block diagram of one version of a medical diagnostic system in accordance with the present invention.

The preferred embodiment of the invention, illustrated in FIG. 1 and bearing numeral 101, uses video technology and includes a hand-held unit 103; a system trolley 115 containing a computer system 119, a printer 117 connected to the computer system, an illumination source 123 and a video camera controller 121; and, on top of the trolley, a computer monitor 107, a keyboard 111, a mouse or pointing device 109, and a camera cradle 113 for the hand-held unit 103. A flexible cable 105 connects the hand-held unit 103 to the system trolley 115.

Figure 2:
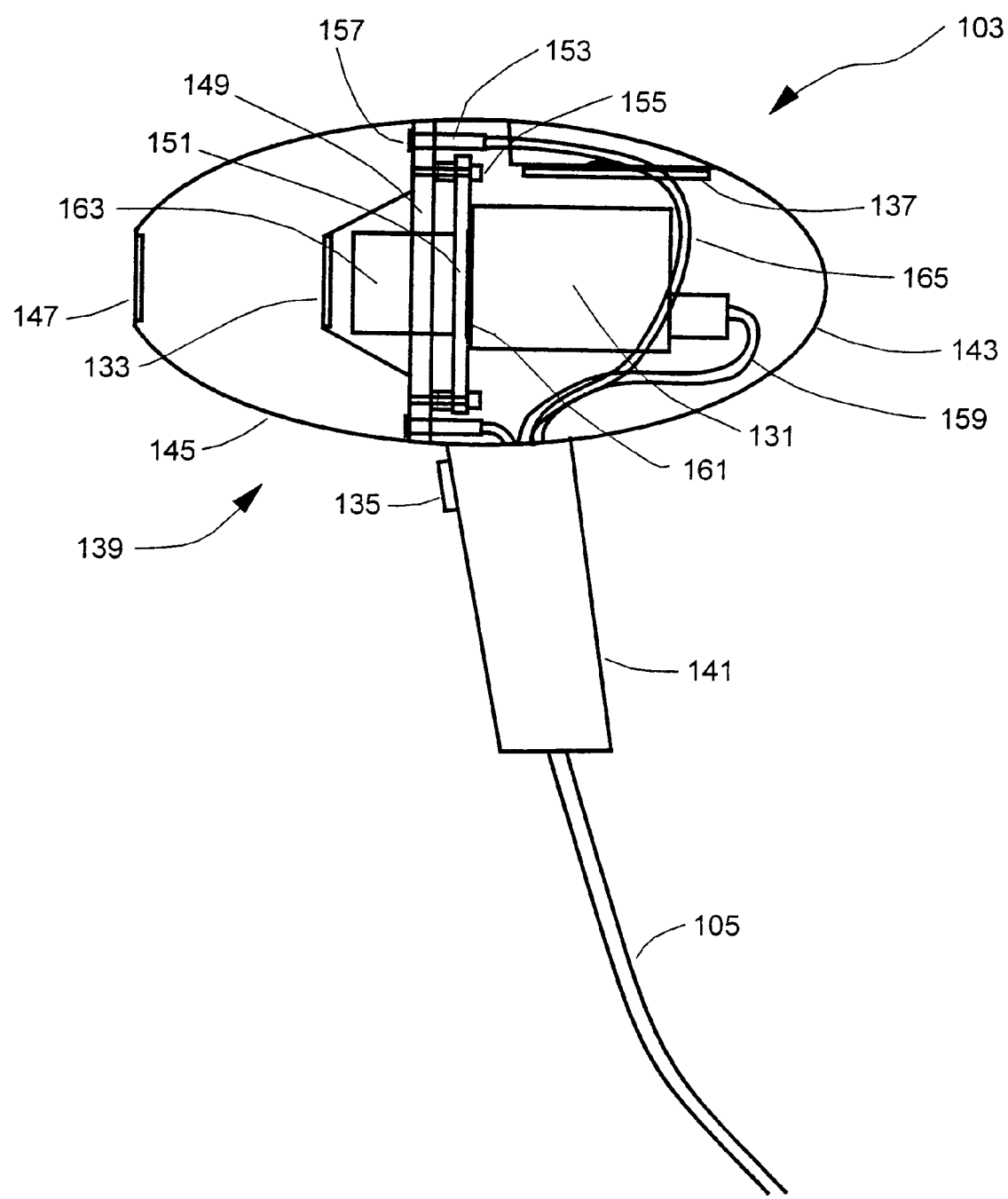
FIG. 2 depicts the hand-held unit of FIG. 1 and includes a video camera and optical fibre illumination source.

As illustrated in FIG. 2, the hand-held unit 103 contains a video camera head 131, an optional inner protective cone and window 133, a trigger switch 135, and an optional miniature computer mouse or pointing device 137. The case 139 of the hand-held unit consists of a handle 141, a main body 143, and a removable outer front cone 145 with window 147. Inside the case there is an internal bulkhead 149, and an adjustable camera mount 151 secured by three mounting bolts 155. Light for an area of skin to be imaged is derived from optical fibres which come out of flexible cable 105 and are connected to four output ports 153 which are located in the bulkhead 149. Each of these output ports 153 has a holographic diffuser 157 mounted in front of it. It is equally possible to use four small lights located at the output ports 153 and to draw power thought the flexible cable 105. The flexible cable also contains the video camera cable 159. The video camera head 131 is attached through a clamp ring 161 located inside the adjustable camera mount 151 to a miniature video camera lens 163. The lens may use a standard C-mount fitting or other more specialised mounts.

Figure 3:
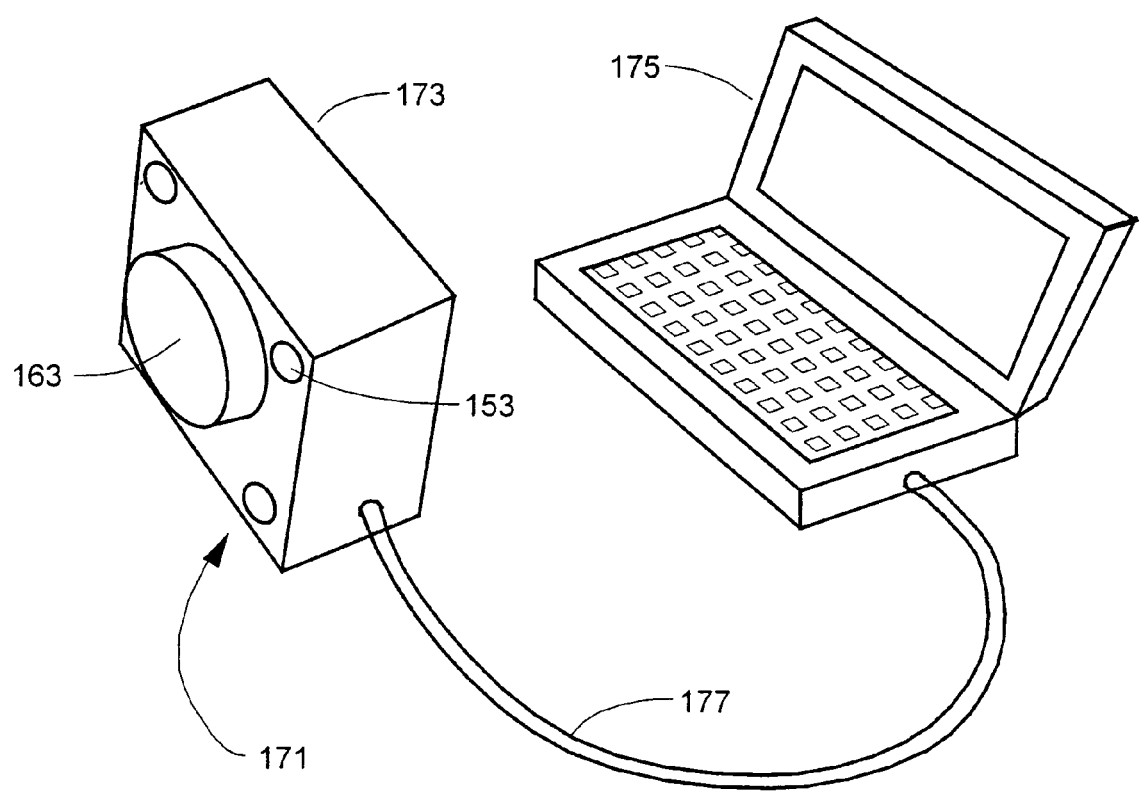
FIG. 3 is a block diagram of another version of a medical diagnostic system in accordance with the present invention.

As illustrated in FIG. 3, another embodiment of the invention uses digital still camera technology. In this case, hand-held unit 171 contains a digital still camera 173, shown here without the necessary cone 145 and window 147. A computer system 175, which may be a laptop, is connected by flexible cable 177 to the hand-held unit 171. The equivalents of the handle 141, the main body 143 and the bulkhead 149 of FIG. 2 are not shown in FIG. 3. The camera 173 may be a custom-designed unit or of readily available commercial still digital camera design, and as the latter change regularly the exact form of the handle 141, the main body 143, the cone 145 and the bulkhead 149 will change with them. However, the same optical arrangement of FIG. 2 is used in the system of FIG. 3, including lens 163, illumination ports 153 around the lens, and the removable front cone 145 (not shown). The cone is in front of the lens at the appropriate distance to obtain the same size field of view as in FIG. 1.

The camera 173 uses digital imaging. This allows transfer of an image directly to the laptop computer 175 by cable, optical or electromagnetic communication means or indirectly by memory chip, disk transfer or other portable memory means. The cable 177 may therefore optionally contain signal cables for the image transfer and optionally fibre optic cables or power cables for the lighting ports 153. In the event that memory chip or disk transfer of images is used, the hand held unit 171 may not have any cable associated with it. Lighting is then built into the camera and powered by a battery.

Images may also be acquired by use of conventional film imaging, giving rise to another embodiment using a format similar to that shown in FIG. 3. Film imaging has the advantage of higher resolution at the present time but the transfer of image information to the computer is slow owing to the film processing and scanning stages involved. The optional cable conduit 177 may supply light or power for lighting to the hand-held unit. It is anticipated that direct digital imaging may eventually offer resolution to match that of film.

The following description is directed to the video camera embodiment. Similar remarks apply to the embodiment based on a digital imaging camera or a conventional film imaging camera where appropriate.

Figure 4:
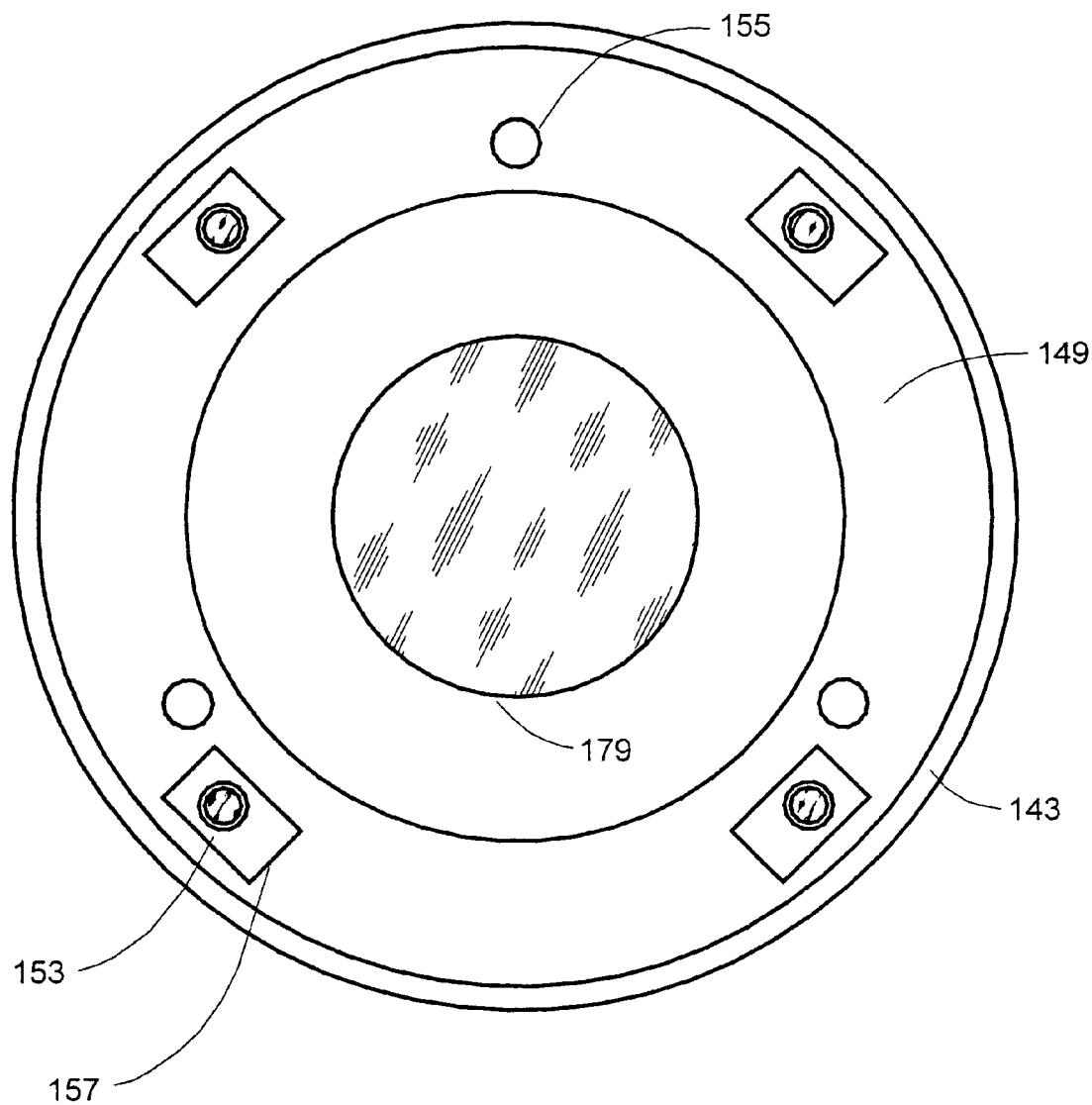
FIG. 4 illustrates the front view of the interior of the hand-held unit of FIG. 2 showing the layout of the illumination ports 153 and the camera mounting screws 155.

The camera mount 151 shown in FIG. 2 has four functions:

1. To hold the video camera head 131 in position inside the hand-held unit 103;
2. To allow rotational alignment of the video camera head 131 with respect to the standard front window 147 by rotation of the clamp ring 161;
3. To provide alignment of the video camera head 131 with respect to the standard front window 147 in X and Y directions by differential adjustment of the three mounting bolts 155 as shown in FIG. 4; and
4. To adjust the size of the field of view 211 at the front of the standard cone 145 (see FIGS. 6A and 7A) by parallel adjustment of the three mounting bolts 155.

Figure 6A:
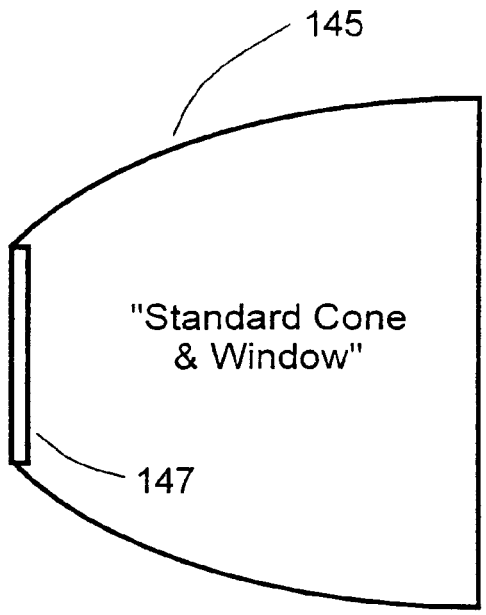
FIGS. 6A–6D illustrate a set of cones that may be placed on the front of either hand-held unit to provide a range of functions in use.

The alignment process is facilitated by the use of a modified standard cone (not shown), one having access holes in the side of the cone and a standard window 147 at the front (see FIG. 6A). The access holes serve to allow adjustment of the aperture and focus of the video camera lens 163 (or the equivalent still camera lens) while the modified standard cone is in place; the edges of the targets 213–217 on the standard window 147 (see FIG. 7A) provide both a scale (the distance between edges across the centre of the field of view 211) and sharp edges for focusing and adjustment of the alignment. It will be apparent to one skilled in the art that other forms of scales and focusing edges may be used on the front of a standard cone 145.

The optional inner protection cone and window 133 shown in FIG. 2 has a clear glass window at the front and serves to protect the video camera lens 163 from being touched or from becoming contaminated, especially while the outer cones are being removed and attached. Contaminants include any optical coupling medium used between the window 147 and the patient's skin.

The cable 105 shown in FIGS. 1 and 2 contains the electrical cable connecting the video camera head 131 to the video controller 121, a bundle of optical fibres 165 with one inlet port at the illuminator 123 and four output ports 153 in the hand-held unit 103, a cable connecting the mouse or pointing device 137 on the hand-held unit 103 to the mouse port on the computer system 119, and a trigger switch cable connecting the trigger switch 135 to the computer system 119.

The trigger switch 135 shown in FIG. 2 is connected to the computer system 119 in the system trolley 115 through an image digitising board or frame grabber 181 (see FIG. 5) such that the actuation of this switch may be sensed by software running on the computer system 119. This provides a trigger signal from the user to the software to cause certain actions such as digitising an image with the frame grabber 181 to take place. The mouse 137 located in the hand-held unit 103 is similarly connected to the computer system 119 through an adapter 183.

The video camera controller 121 provides the majority of the electronics required to support the video camera head 131. The video camera should be of very high colour image quality, preferably a 3-CCD unit with a resolution of at least 760*570 pixels for each of the three colour sensors (commonly being red, green and blue). Alternatively, solid state cameras using sensors based on other technologies such as CMOS or CID may be used. The term "pixels" is commonly used to denote the individual sensor sites found in the CCD sensor arrays in a 3-CCD camera, but would equally apply to cameras made with other technologies such as CMOS and CID. It also applies to the picture elements of a digitised image from a film camera. If a digital still camera is used, it should provide an image of high quality at least similar to that of the 3-CCD camera.

Figure 5:
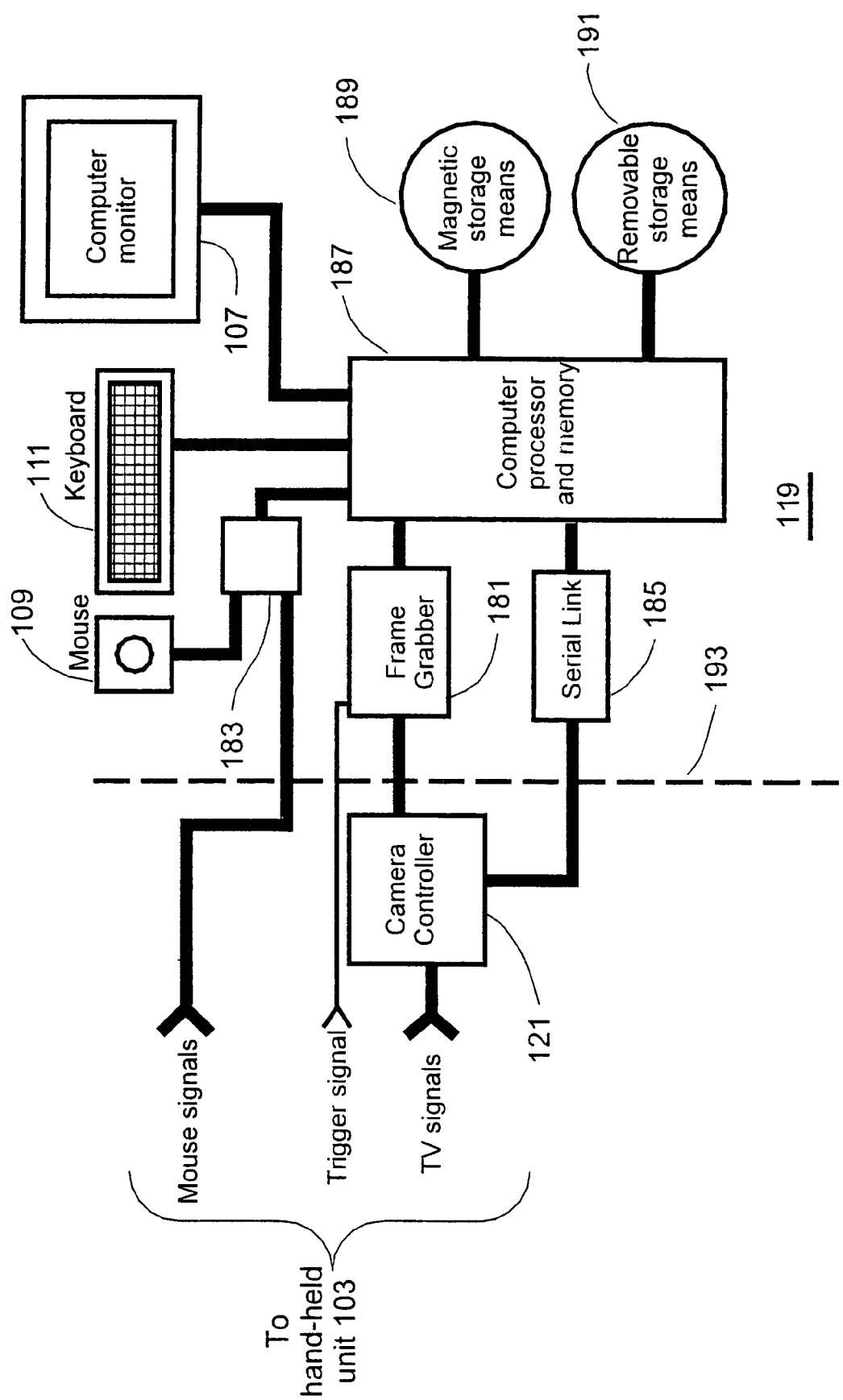
FIG. 5 is a block diagram of the computer system, interfaces and storage media.

It is also desirable that the functions of the camera controller 121 be controllable from the computer system 119 via a standard RS232C serial port 185 (see FIG. 5). Best quality images are normally obtained from a video camera by using RGB signals rather than composite video. The video camera system (consisting of the camera head 131 and the camera controller 121) may be, for example, a Toshiba IK-TU48P, although other video camera systems of similar quality may also be used. It will also be clear that a video camera system with a "remote" camera head small enough to fit into the hand-held unit 103 is desirable for convenience. The Toshiba IK-TU48P camera head 131 has dimensions of approximately 40 mm*40 mm*33 mm wide.

If a video camera is used the video signals or images output from the video camera controller 121 are converted to digital form by a computer interface unit commonly known as a frame grabber 181 and located in the computer system 119, as shown in FIG. 5. (The computer system 119 is depicted to the right of dashed line 193 in FIG. 5. Elements to the left of the line with the exception of camera controller 121 are in the hand-held unit 103.) The digitised images are then taken into the computer processor and memory 187 of the computer system 119 for processing, and may also be stored on various forms of computer storage means 189 (such as a hard disk drive) and displayed on the computer monitor 107.

If a digital still camera is used, the images are normally converted to digital format within the camera and may be transmitted to the computer system 119 via means as previously discussed.

It is advantageous to use a combination of imaging means such as a video camera and image digitisation means such as a frame grabber which give a digital image having what are termed "square pixels". That is, an area of the digital image measuring N pixels wide by N pixels high should actually represent a square area of the surface being imaged. However, for good results this must be achieved by the use of a video or digital imaging camera having square pixels and a frame grabber rate adjusted to take one sample per pixel.

While it is possible to use a camera with non-square pixels and to attempt to compensate for this by altering the frame grabber sampling rate, as shown in U.S. Pat. No. 5,836,872, this results in significant loss of image quality and sometimes serious image artefacts known as "aliasing". Such an approach is well-known to be unsatisfactory. The Toshiba camera referred to above does have square pixels.

It will be obvious to a person skilled in the art that the computer system 119 used in our invention may be of any form able to support a frame grabber 181, computer storage means 189, and a computer monitor 107. Alternatively, if another form of camera is used such that the data is transferred by means other than a frame grabber, these means must be supported. The computer storage means may optionally include removable media 191 such as magnetic disk storage media and removable optical storage media such as writable CDs of various forms and writable DVDs.

Figure 6B:
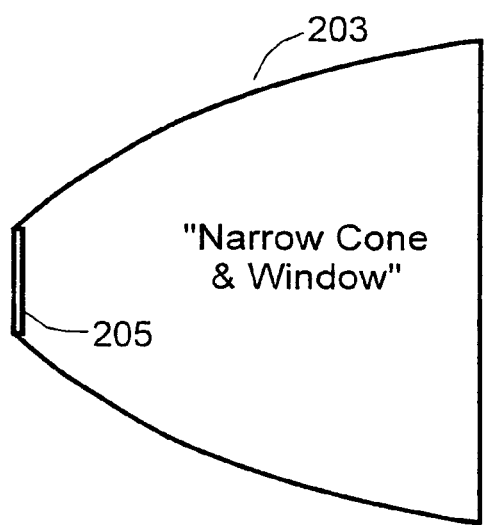
Figure 6C:
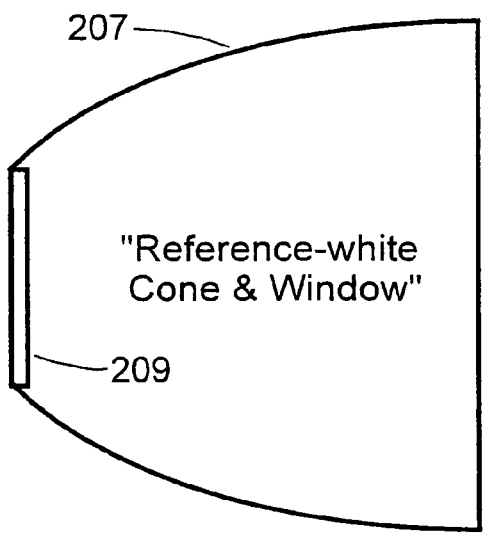

FIGS. 6A–6B show a set of cones that are used with the hand-held unit 103. The cones serve to define different fields of view for different applications, and the individual functions they serve will be discussed in detail below. Appropriate thickness windows are used in these cones in order to minimise the TIR effect, as described above.

Figure 7A:
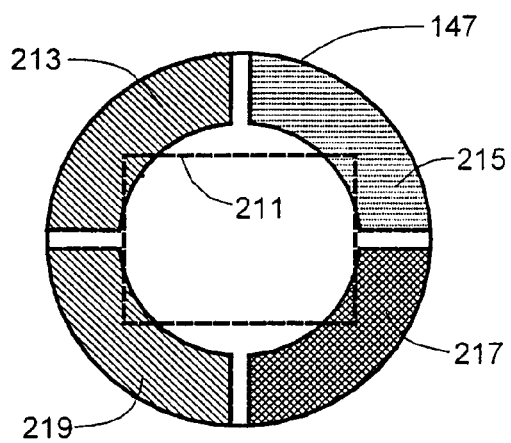
FIGS. 7A–7D illustrate the fields of view of the video camera when different cones are used.

FIGS. 7A–7D are views from inside the various cones toward the windows. The field of view of the video camera head 131 is generally shown as a rectangle 211, although this may include the special case of a square. FIG. 7A shows the rectangular field of view 211 of the video camera head 131 (or still camera head 173) when the hand-held unit 103 (or 171) is fitted with a standard cone 145. The size of the field of view 211 is determined by the effective focal length of the lens 163 and the distance from the lens 163 to the window 147. The effective focal length of the lens 163 is determined by the nominal focal length, as defined by the manufacturer, optionally slightly modified by a spacer placed between the lens 163 and the video camera head 131. This spacer functions as any normal extension ring used on an ordinary camera. However, if used, it may also form part of the clamp ring 161 which holds the camera in place on the adjustable camera mount 151. Other forms of camera mount 151 and clamp ring 161 are obviously possible. Since the effective focal length of the lens is largely determined by what is commercially available, the distance from the lens 163 to the window 147 is used to achieve the desired size of the field of view 211. Once this distance to the window 147 has been determined, the focusing of the lens 163 is adjusted to ensure best focusing on the window. With the focusing fixed, other cones such as the narrow cone 203 must be designed to place their corresponding windows such as the narrow window 205 at the same distance to also be in focus. Operator adjustment of the focus is not required.

The field of view 211 encompasses the clear central region of the standard window 147, as shown in FIG. 7A. However, a peripheral band of opaque paint or other coloured material of suitable form is placed around the edge of the standard window 147, and portions 213–219 of this peripheral band are visible in the field of view of the imaging device. These portions are those previously referred to as targets and may be used during the image analysis to check on the stability of the lighting and the colour calibration, and aid in compensating for the TIR effect, as will be described below. They may be of a range of colours, including either all white or white, light grey, dark grey and black, or some other combination.

Figure 7B:
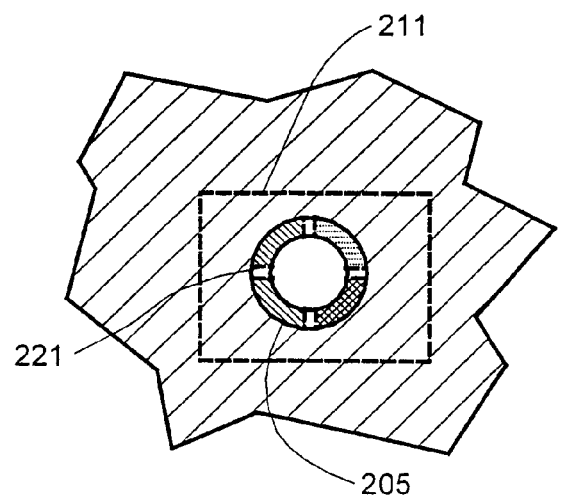

FIG. 7B shows the rectangular field of view 211 of the video camera head 131 (or still camera head 173) when the hand-held unit 103 (or 171) is fitted with the narrow cone 203 of FIG. 6B. The field of view now encompasses the whole window 205 (see FIG. 6B) and much of the surrounding interior of the cone 203. The narrow cone 203 permits the narrow window 205 to be applied to smaller regions of the patient's body such as the ear or beside the nose. Such a smaller window is used for two reasons. First, the standard window 147 may be physically too large for some locations. Second, in some images, such as that of the ear, it is found that the shadows due to the natural crevices outside the area of real interest may interfere with the image analysis algorithms. With the narrow cone 203, a smaller area of skin will be available for image analysis. A peripheral band of paint 221 is placed around the edge of the narrow window 205 on the side of the window which is in contact with a patient's skin. The full circumference of this paint is visible in the field of view. This peripheral band is divided into sectors of multiple colouring.

Both cones 145 and 203 are made so as to seal the front region where the window is set into the cone to eliminate or at least minimise the entry or retention of any contaminants, such as any optical coupling medium that is used between the window and the patient's skin.

Figure 7C:
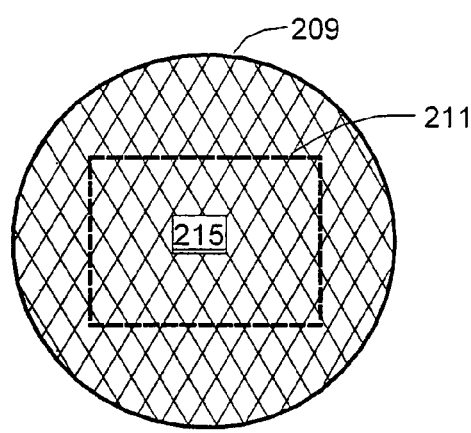

FIG. 7C shows the rectangular field of view 211 of the video camera head 131 (or still camera head 173) when the hand-held unit 103 (or 171) is fitted with a reference-white cone 207. This field of view is filled with the reference-white colour 215, a suitable reference-white material being applied to the outer surface of the reference-white window 209. (While the cone 207 may have a transparent window at its front, the effect of the reference-white colour is to make the window non-transparent.) Reference-white window images provide information on lighting and imaging system conditions at the time of image capture.

Figure 7D:
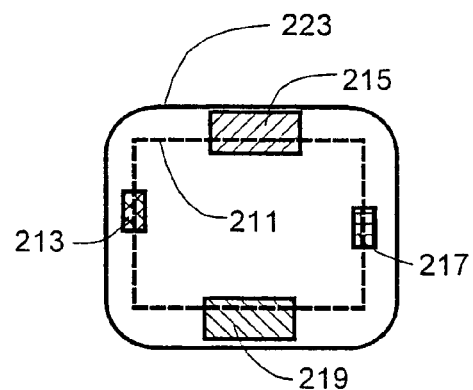
Figure 8:
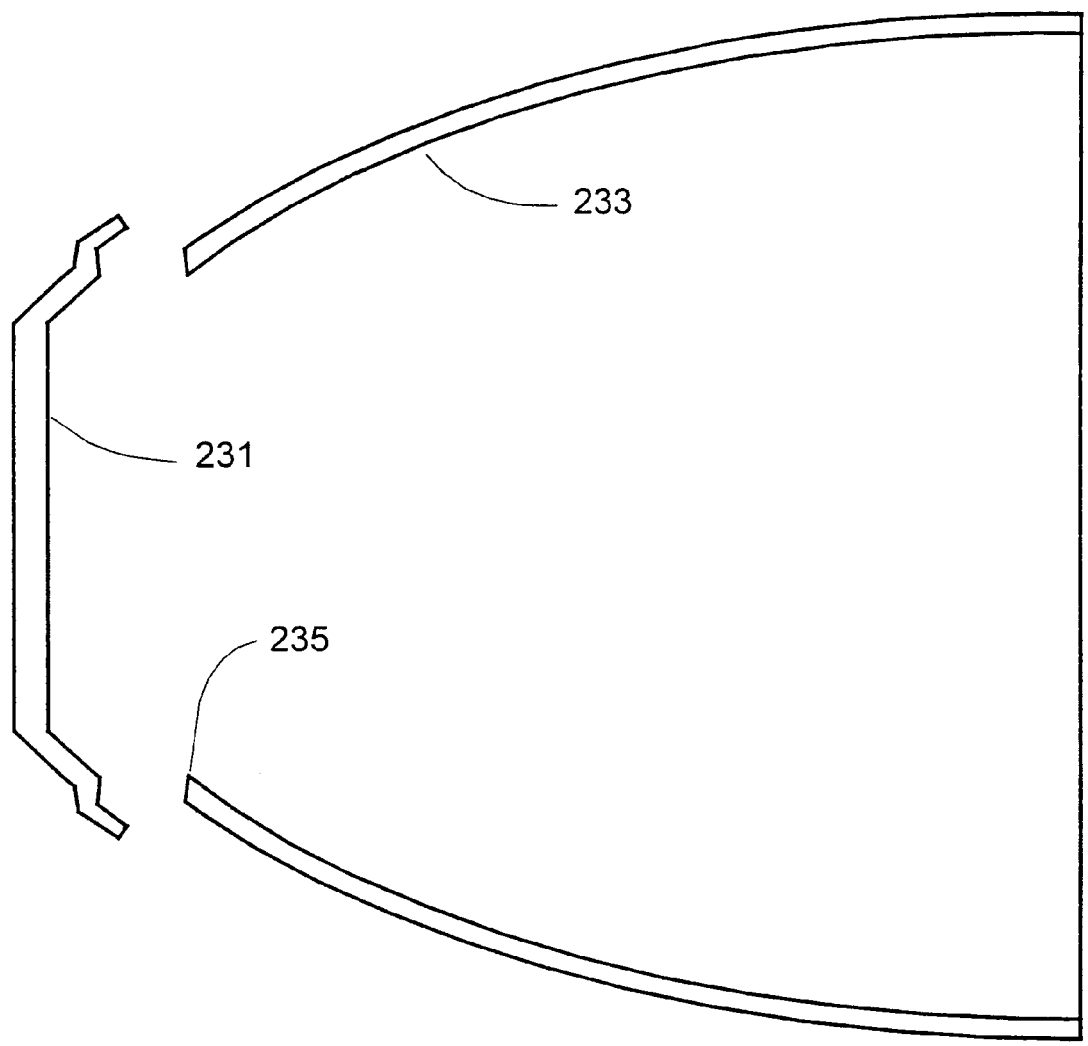
FIG. 8 illustrates a design for a cone with a replaceable front window, which can be configured to be used only once.

FIG. 7D shows another version of the standard window. In this case, the window 223 is not round and the targets 213–219 have been moved to the edges of the field of view 211 rather than being at the corners. This format is particularly appropriate for use with a removable front section 231 as shown in FIG. 8 where the removable front section is made by a method such as injection moulding. The standard cone 233 of FIG. 8 is open at the front but has a suitable designed rim 235 into which the removable front section can be snapped. The rim shown is illustrative only; other forms of the rim may be used.

All windows illustrated in FIG. 7 are made from a transparent optical quality material reasonably resistant to abrasion under normal clinical use. They all have smooth surfaces. Glass such as that known as B270 made by Schott Garsco may be used, with the added advantage of it being hard and therefore very resistant to scratching or other damage caused by abrasion or cleaning. Sapphire or optical plastics may also be used. In the event that a material is used with a refractive index significantly higher than that of the B270 glass (approximately 1.525), it will be necessary to increase the window thickness to maintain the necessary reduction in the TIR effect.

The removable cones shown in FIGS. 6A–6D have different forms which may be referred to as the standard cone 145 having a standard viewing window 147 at the front, the narrow cone 203 having a small viewing window 205 at the front, the reference-white cone 207 similar to the standard cone 145 but having a reference-white (opaque) "window" 209 used for image normalisation at the front in place of the standard window 147, and the photomap cone 201 having a wide-angle adapter lens 210 in place of a window. Each of the standard cone 145, the narrow cone 203 and the reference-white cone 207 has a diffuse matt black interior which is substantially non-reflecting. In addition, there may be grooving on the inside surface parallel to the front window to minimise light from the optical fibre ports 153 from reflecting off the inside surface of the cone onto the window at the front. This is similar to the standard black grooving found on the front of a film camera lens and is a common technique in optics.

Alternatively, the interior of the standard cone 145 may be a diffuse matt white, which will of course reradiate white light in a substantially non-directional manner, unlike reflected light which is highly directional. Similar grooving may also be provided. This produces a different lighting regime known as an integrating sphere. In this case the illumination reaching the skin surface contains a substantially non-directional component. The design of the inner cone surface must then ensure that the uniformity of the total light field is not impaired.

The standard window 147 is held by the standard cone 145 at a fixed distance from the camera head 131, and the video camera lens 163 is focused on the outer surface of the window 147. Maintaining the standard window 147 at this fixed focal distance is a major function of the standard cone 145 and this applies equally to the narrow cone 203 and the reference-white cone 207. The functions of the standard window 147 and the narrow window 205 are to hold the skin of the patient, which is pressed against the flat front of the window, at a fixed focal distance from the video camera head 131 such that the whole field of view will be in sharp focus, and to provide a suitable surface for the index matching oil used in the ELM technique. A further function of the cones and windows is the maintenance of a fixed magnification or scale in all images taken this way. Thus it is a requirement that all forms of cones place their windows at the same distance from the camera head 131. It follows from this that the video camera lens used need not include provision for automatic or computer-controlled zooming or focusing. It should be noted here that an optical coupling medium such as an oil may be used between any of the windows and the skin of the patient in order to reduce the effect of surface-scattered light and hence to improve the imaging performance. It is therefore important that the windows be sealed into the cones in such a manner as to preclude any of this optical coupling medium from getting inside the cone during use. Alternatively, the window can be moulded as a part of the cone. The wide angle cone 207 serves to hold the wide angle lens 210 at the appropriate distance from the video camera head 131 so as to provide a field of view subtending an angle in the order of 10–15 degrees. The wide angle cone 207 is not subject to the fixed magnification requirements. The focus of this lens may be adjustable.

The layers of material forming the targets on the standard window 145 and the narrow window 203 are required to be very stable in spectral response, substantially opaque and yet thin, typically under 0.15 mm thick for operational reasons associated with shadows at the edges of the material. A thick layer creates shadows due to the directional beams from the fibre optic ports and the small lens aperture on the camera, as well as compression of the imaged skin, adding to the loss of image area.

The layer of material applied to the reference-white window 209 is required to be very stable in spectral response, substantially opaque, extremely uniform across the whole window, and substantially white or spectrally flat in the visible region. Reference-white window glass should be of the same thickness as the other window glass to ensure imaging conditions equivalent to those of skin imaging. As a thin paint layer can be somewhat translucent, if paint is used for this material it is necessary to ensure that the total paint layer is thick enough that there is negligible light transmission through it. This may be achieved by using several coats of paint. Alternatively a separate reference surface may be used, viewed through a window of the same thickness as the standard window 147, with the standard optical coupling medium between to eliminate all air. This ensures that the imaging conditions are equivalent to those for skin imaging. The requirements of opacity, stability and uniformity for the surface are the same. Suitable materials include glazed ceramic tiles and other smooth stable materials.

It is essential that the reference-white material be very uniform across the field of view. If a material of the general form of paint is used, it is necessary to use pigment carriers and pigments of high quality and purity, to ensure such materials are well mixed before use, and to maintain strict attention to cleanliness during the manufacturing process. In this case, procedures such as continuous in-plane motion of the material or averaging a plurality of images, as claimed in publication WO 98/37811, are not necessary. It has been found that $TiO_2$ and carbon pigments give uniform and spectrally stable white and black colours over time. Both the paint or other material forming the targets and the reference-white material must adhere to the window surfaces in such a manner as to exclude all air. The reason for this is as follows. Taking paint on glass as a representative case, most paint carriers have a refractive index quite close to that of glass, so the glass/paint loss due to the change in refractive index is minimal. Provided the paint adheres properly to the glass this loss will also be stable. However, most paints do not adhere properly to glass or to some transparent plastics. Poor adhesion results in specular reflection and creates imaging conditions dissimilar to those of ELM skin imaging. Epoxy-amine paint does bond chemically to glass and this type of paint should be used on glass. Sericol Polyscreen PS two pack screen ink has been found suitable (Sericol Ltd, Pysons Rd, Broadstairs, Kent, CT10 2LE, UK). Other materials may require other specialised paint carriers to achieve proper bonding. It is possible to use one layer of clear epoxy-amine paint on the glass for bonding and then layers of another kind of paint on that, provided that adhesion between the two kinds of paint is good. Enamel paint applied over a ground glass surface of the appropriate roughness also has a high level of adhesion provided extended cure-time is allowed. Grinding with 40 um grit or 220 gauge grit has been found satisfactory.

A second method of implementing the reference-white material is to use a material containing a suitable white pigment placed against the outer surface of the standard window. To prevent any reflections, an index-matching liquid or air excluding mechanism must be used between the surface and the window. This can take a number of forms. One form consists of a suitable reference white material such as a glazed ceramic tile with a very flat surface, placed against a standard clear window of standard thickness, with the standard index-matching liquid between the two. A second form consists of a thin film which may be opaque white or clear. If the film is clear, a layer of suitable white paint or other material may be placed upon it without an air gap. The film may be attached to the window with a layer of adhesive which serves both to retain the film in place and to act as the air-excluding mechanism. Following the recording of the reference-white image the film could then be removed to leave the standard window in place for use as previously described. Another implementation uses a material sprayed or otherwise coated onto the front of the window and subsequently peeled off. In this case, no index matching fluid is used; the material adheres directly to the window and excludes air. The adhesion does not have to be of a permanent or long-term nature. (Such materials are used as single-use protective coatings on objects with finished surfaces during transport.) The material may incorporate the necessary white pigment directly or may have a paint or other material applied over it. Other variations on this method involving elastomers suitable for a more simple sensor than a TV camera are disclosed in U.S. Pat. No. 5,852,494 in the name of Skladnev at al.

As discussed above, the alternative standard cone of FIG. 8 has a replaceable window 231. The window is referred to as a "per-use" window. The cone 233 is basically the same as cone 145 but with the tip removed and transferred to the removable front section 231. This removable front section incorporates the window in it. It may be made as a single unit from optically clear material with opaque coatings on the inner and outer surfaces except where the window 147 should be, or it may alternatively be made from two components joined together. The removable front section 231 clips into or otherwise joins the cone 233 at the bevelled edge 235. The junction at the rim 235 should protect against the ingress of contaminants. The form shown in FIG. 8 is a simple form for the purpose of illustration; other forms of junction are possible. It is of course desirable that the removable front section 231 should actually clip onto the cone 233 in a stable manner. The region around the window may have paint applied to it just as it is applied to the standard cone 145.

The per-use window 231 is cheaper to manufacture than the whole cone 145 and window 147, and could be provided to the user as a clean or even sterile unit. This permits the user to use a new unit for each patient, avoiding cross-contamination between patients. The use of a per-use element for avoiding cross-contamination is known in the medical environment, and is shown for solely this purpose in U.S. Pat. Nos. 4,930,872, 5,527,261, 5,527,262, 5,662, 586 and 5,836,872. However, this concept is extended as follows. If made by injection moulding, the shape of the front surface may be arranged so as to present a flat surface after the application of the peripheral band of paint, avoiding any physical discontinuities. The replaceable window unit, as supplied to the user, may incorporate the reference-white material over the top as a removable film layer, as discussed above. Once the reference-white image has been acquired, as will be described below, the removable layer may be peeled off, leaving a window of standard design. However, in the process of removal it is intended that the reference-white material, be it paint or other adherent layer, will be effectively damaged, preventing it from being reused. Since a reference-white image must be acquired for each patient examination, a new sterile front window would be required for each patient. This is in keeping with current medical ethics.

In addition our invention allows for the incorporation into the "per-use" cone during manufacture a unique identification mark, serial number, barcode, electronic tag or character string, either on the "per-use" window or incorporated as identification on the window packaging. This identification will allow the system software to verify that each "per-use" window will only be used once, thus ensuring that a clean window is used for each patient. The system software will verify that the "per-use" window is valid before the acquisition of the reference-white image. If the "per-use" window has been used previously a message will prompt the system operator to place a new "per-use" window on the cone.

Throughout this application, a reference-white material is used. However, this is only the preferred colour material. Any reference material of known stable colour can be used.

Referring back to FIG. 2, it is important that video camera lens 163, which is also referred to as a miniature C-mount lens, transmit the image from the front of the standard cone 145 to the internal CCD sensors with maximum fidelity. This means that the lens should provide a flat field, negligible pincushion distortion, sharp focusing and precise geometrical colour registration between the red, green and blue images. These requirements are well known to a person skilled in the art of optics. It has been found that a miniature C-mount lens made specifically for high-resolution 3-CCD cameras and described as an "apochromat" provides satisfactory performance. A suitable lens is made by Fujinon (Fuji Photo Optical Co Ltd, 1-324 Uetake, Omiya City, Saitama 330-8624, Japan) and designated TF-15DA-8.

The quality of the illumination field is very important. If a fibre optic lighting arrangement is used as described above, the individual optical fibres 165 are randomised before being split into the output ports 153; this ensures the most even possible distribution of light between the output ports. The glass currently used for the optical fibres is selected to have a low absorption and flat spectral response across the visible light range of wavelengths to avoid significant light loss and any coloration being added to the light passing through the fibres. The illustrative embodiment of the invention utilises four output ports or light sources, but the invention is not limited to this number. However, as will be discussed below, four ports allows a particularly flat illumination field to be generated.

Figure 9A:
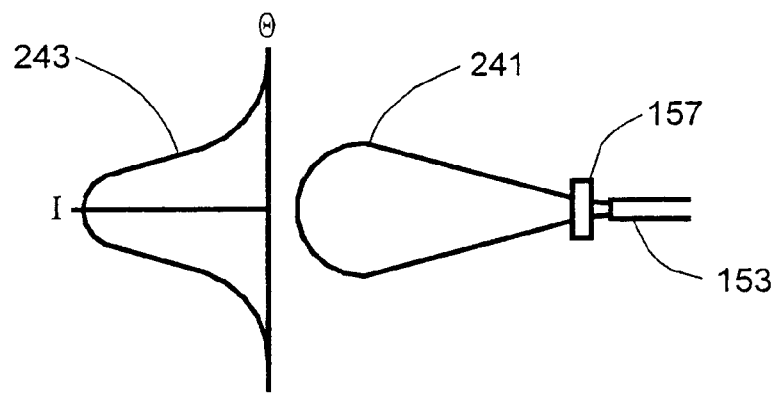
FIG. 9 depicts one method of providing a substantially uniform illumination field at the window at the front of a hand-held unit.
Figure 9B:
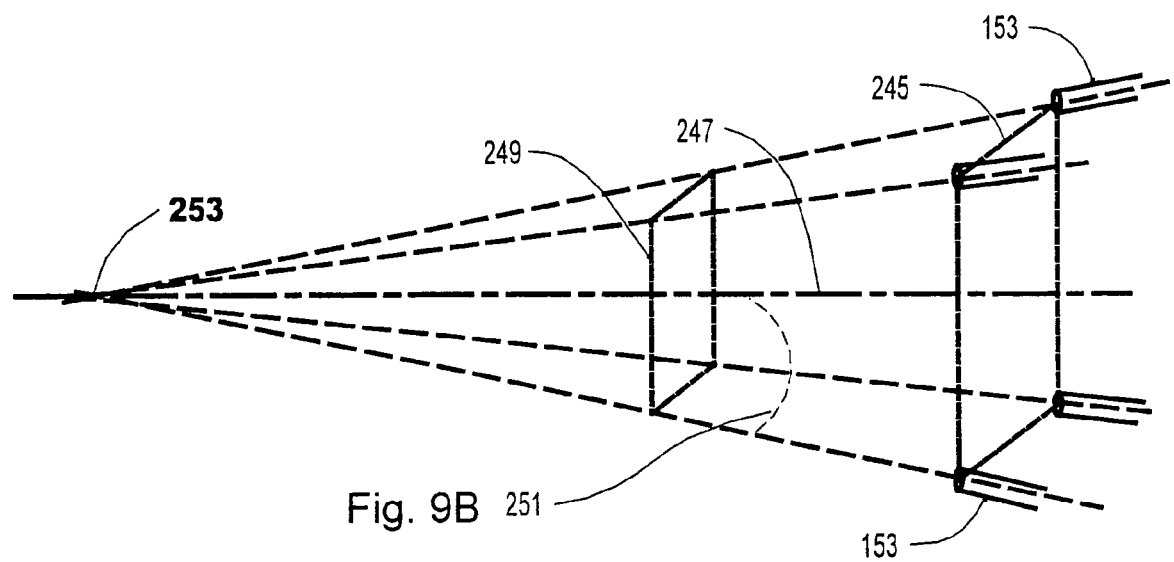

The output ports 153 of the optical fibres, as shown functionally in FIGS. 2, 4 and 9, may each optionally have a holographic diffuser 157 placed in front of them to further randomise and smooth the light coming from the output ports to the window 147 at the front of the cone 145. This has been found beneficial in removing any pattern in the illumination created by facets in the reflector of the quartz-iodine lamp (the preferred light source) in the illuminator section 123. An ordinary ground glass diffuser as used in the system in publication WO 96/16698 scatters light in all directions and hence results in the loss of most of the available light from the forward direction, which is undesirable; a holographic diffuser may be designed to spread out a beam by a certain amount in the forward direction only, so the use of a holographic diffuser preserves most of the light in the forward direction. Suitable holographic diffusers are made by Physical Optics Corporation, 20600 Gramercy Place, Building 100, Torrance, Calif., 90501-1821; a unit with a 20 degree beam-spread is preferred.

The illuminator section 123 in the trolley 115 (FIG. 1) consists of a regulated power supply typically providing a stable supply to a quartz-iodine lamp. A 12-volt 50-watt quartz-iodine lamp of the ANSI EXN type has been found suitable. This lamp shines through an infrared filter to illuminate the source face of the optical fibre bundle, thereby providing cool white light with a colour temperature of about 3050K to the hand-held unit 103. A cooling fan is typically included in the illumination source. Other lamps and reflectors may also be used. For example, a unit with an elliptical reflector is more efficient in putting light into a small aperture such as a fibre optic bundle, but must be aligned with more care.

Alternatively, a light source may be placed elsewhere inside the hand-held unit 103 or a separate light source may be placed at each of the output ports 153, in a similar arrangement so as to produce a reasonably flat light field. These lights may include small quartz-iodine lamps, light emitting diodes or small flash lamps. It is important that the illumination generated be substantially uniform and reproducible from image to image, and that the power dissipated within the hand-held unit be limited.

In the case of light emitting diodes it is possible to use units of different wavelengths such that the light produced for any one image may be of a substantially single colour, but that the sum of the wavelengths or images provides a representation equivalent to that created by white light. In this case the camera need not be able to separate the colours in the same way a colour video camera separates the image into red, green and blue components. This allows the use of a "black and white" camera in place of a colour camera, reducing the cost of the camera.

The same effect may be achieved by placing suitable colour filters over the quartz-iodine or flash illumination sources either in the hand-held unit or externally such that substantially red, green and blue illumination may be created for different images. The use of coloured filters between an external quartz iodine lamp and the fibre optic bundle is well known, being disclosed, for example, in publication WO 98/37811 and in U.S. Pat. No. 4,738,535. Again, these single-colour images may be combined to produce a full-colour image. The filters may be separate physical units such as are commonly used in film photography, or a single switched liquid crystal colour filter may be used. While the foregoing has been discussed in terms of the red, green and blue colours commonly used in video cameras, the use of other colour combinations (not necessarily limited to three in number) to achieve better analysis of the final image is possible.

In the illustrative embodiment of the invention, as a result of the properties of the components of the illumination system (the beam spread of the type EXN quartz-iodine lamp that is used, the distance between the quartz-iodine lamp and the entry to the fibre-optic bundle 165, the numerical aperture of the glass optical fibres making up the bundle 165, and the 20 degree beam-spread of the diffusers 157), the light beams 241 (FIG. 9A) coming from the four outlet ports 153 have approximately the same Gaussian beam spread 243. The four output ports 153 are arranged in a plane at the corners of a square 245 (FIG. 9B) around the central axis 247 of the hand-held unit 103. The four output ports may be slightly inclined to the central axis 247 by an angle of inclination 251. If this angle is non-zero and the tilt is inwards, the beams may come to a common convergence at point 253 on the central axis 247. Such a tilt may be used to meet the light field flatness criteria described below.

Figure 9C:
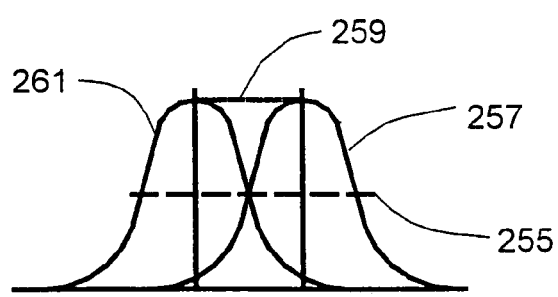

By careful selection of the distance between the plane containing the square 245 of output ports 153 and the plane 249 containing window 147, the length of the sides of the square 245 and the angle of inclination 251 to the central axis, it is possible to obtain a substantially flat field of illumination over the window 147. It should be noted that the distance between the plane containing the square 245 of output ports 153 and the plane 249 containing window 147 is largely constrained by the required distance between the lens 163 and the window 147 as mentioned above. The method of achieving this flat field is based on overlapping the decreasing intensity of one Gaussian beam spread 243 (FIG. 9A) with the increasing intensity of another similar Gaussian beam spread as illustrated in FIG. 9C by beam spreads 257 and 261. When the two intensity distributions are spatially separated such that they overlap at the half-intensity level 255 as shown in FIG. 9C, the resulting summation of intensities has a flat central region 259, this separation being known as the Raleigh criterion for the separation of two Gaussian pulses. The distance from the centre of the Gaussian beam spreads 257 and 261 to the half-intensity point may be termed the half-width of the Gaussian curve, and at the Raleigh separation the centres of the two similar distributions will be at twice this half-width. Similarly, when four such distributions are combined in a square in the plane 249 as in the arrangement shown in FIG. 9B, the central region of illumination has a substantially uniform intensity. Thus the sides of the square of centres in plane 245 should be each two times the half-width of the Gaussian curve of the intensity distribution in the plane 249. In the illustrative embodiment of the invention, the half-width of the light distribution coming from each port is approximately 24 mm at the plane 249, although the distribution is not strictly Gaussian. This small departure is due to the influence of the beam profile from the reflector of the illuminating lamp. To achieve this Raleigh criterion with the fibre optic ports aligned parallel to the central axis requires, in principle, that the sides of the square 245 be twice 24 mm or 48 mm. Owing to the mentioned departure from a strict Gaussian beam curve this turns out to be slightly too large, but a smaller separation has disadvantages of reflections, as discussed below. Thus, while this dimension is used in the illustrative embodiment of the invention, a slight inwards tilt is also used to compensate for the small departure from a strictly Gaussian beam profile and simulate a smaller separation. (The use of two overlapping light fields in this manner to produce a flat region is known and has been shown in Australian patent No. 709,459 entitled "Systems and Methods for Measuring at Least Two Visual Properties of an Object" in the name of Adriaansen et al.) The shape of the light field distribution may be altered by the amount of light reflected off the inner surface of the cone 145 (FIG. 6A). This is particularly so if a white inner surface is used in the cone, in the integrating sphere mode mentioned above. With a high level of scattering from the white inner surface, the additional illumination may also be made substantially uniform across the field of view. This uniformity of light field contributes to the colour calibration of the system as will be explained below.

It will be obvious that the precise dimensions, material properties and number of optical fibre ports may be varied over a wide range while still enabling a combination of intensity distributions to yield a uniform central region of illumination. However, the use of four ports on a square is found to be particularly simple and effective.

A number of lighting systems for achieving a similar objective are available commercially. A four-port illuminator using a half-silvered mirror is available from Edmund Scientific (101 East Gloucester Pike, Barrington, N.J., 08007-1380): The light is reflected downward by the mirror while the user looks through the mirror. The device is called a diffuse axial illuminator, but since the lighting source geometry is not tightly controlled the light field uniformity is variable. This general loose arrangement is similar to that claimed in publication WO 96/16698. The R-90M Munchkin illuminator sold by Chiu Technical Corporation (252 Indian Head Rd, Kings Park, N.Y. 11754) uses eight similar fibre-glass ports at a variable tilt. Neither of the aforesaid devices uses a holographic diffuser. Illumination Technologies Inc, USA (1-800-7384297, http://www.ntcnet.com/it) sells a 15-port ring illuminator. Several companies such as Edmund Scientific and Fostec Inc. (62 Columbus St, Auburn, N.Y., 13021-3136) market ring illuminators which have a continuous line of fibre-optics in a circle. The overlap is controlled in these cases by varying the distance to the subject plane; variable tilt is not possible although a fixed tilt is possible. These devices are generally designed for use in microscope illumination, and sometimes for dark-field illumination. The Lite-Mite by Stocker & Yale Inc. (32 Hampshire Rd, Salem, N.H., 03079) goes further, by placing a ring-shaped fluorescent tube around the microscope or camera lens. Finally, ring flashguns are available for use with scientific cameras for close-up photography. However, all of these have some degree of variability in operation and are principally designed to give "surround" illumination to reduce the presence of shadows. They are not designed primarily to give a very even field of illumination. No prior art device provides an even field of illumination to the extent possible with our invention.

Figure 10:
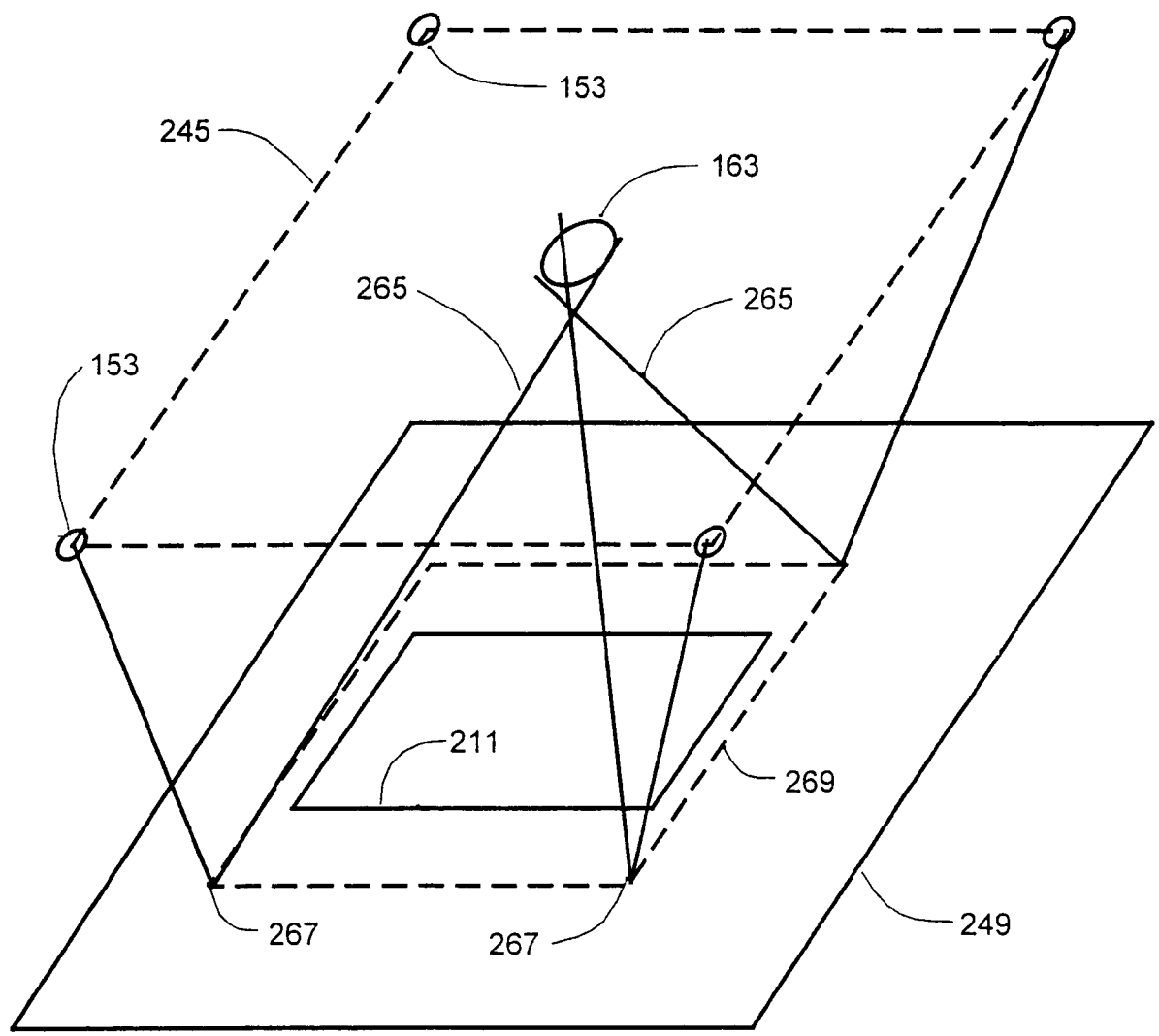
FIG. 10 illustrates the geometry involved in avoiding reflections of the fibre optic ports.

A further constraint on the arrangement of the four output ports 153 is that there should be no light reflected from the window 147 into the video camera lens 163. The geometry of this problem is illustrated in FIG. 10. The constraint is met by ensuring that the sides of the square 245, on whose corners the fibre optic ports 153 are located, are sufficiently large that the reflections 265 of each port 153 from the plane 249 lies outside the field of view of the lens 163. The plane 249 corresponds to the inner surface of the window 147. With the actual dimensions used in the illustrative embodiment of the invention, the positions 267 of the reflections 265 in plane 249 as would be seen by the lens 163 are on the corners of a square 269 of approximately 27 mm on each side. This square is obviously larger than the actual field of view 211 of lens 163 which is 24 mm by 18 mm, so the reflections 265 are outside the field of view.

Figure 25:
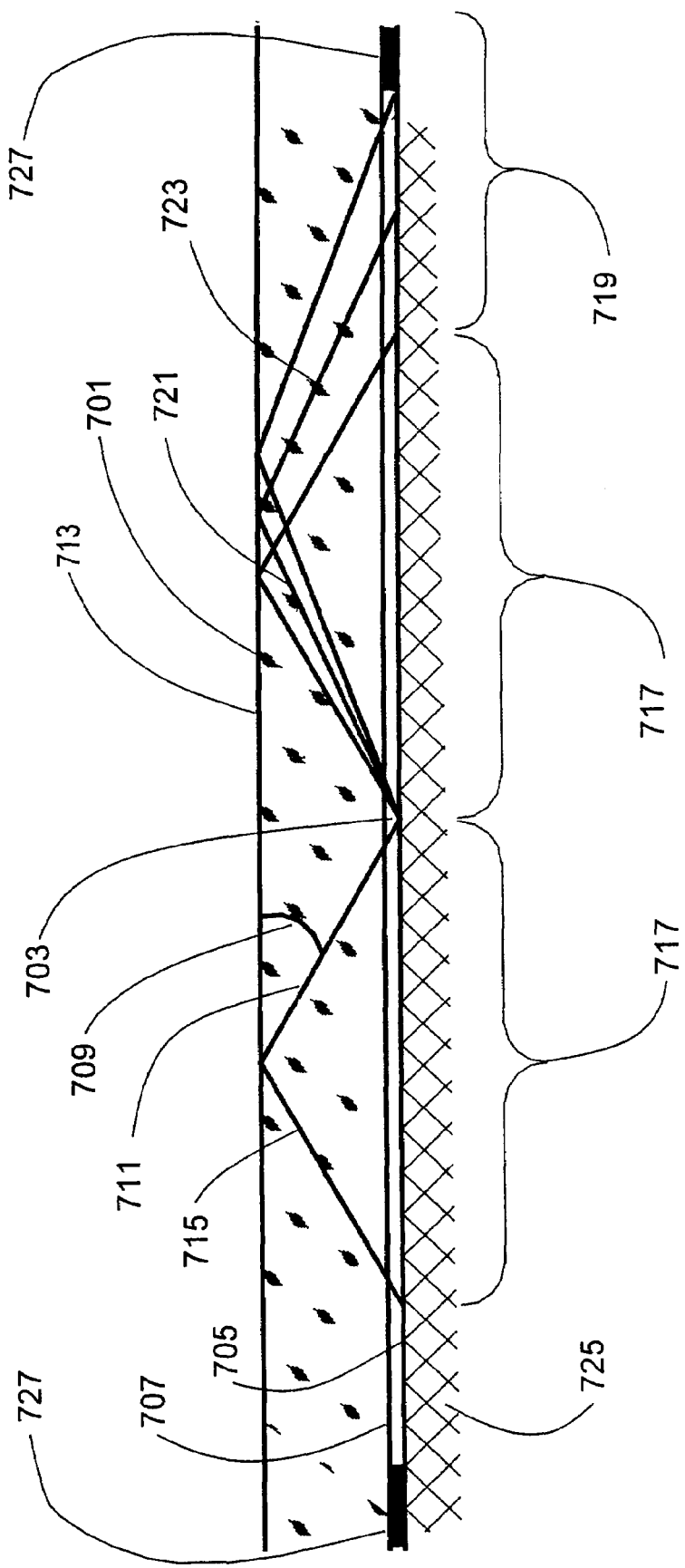
FIG. 25 illustrates the phenomenon referred to elsewhere as total internal reflection (TIR) or "oil effect"

FIG. 25 illustrates the phenomenon of total internal reflection (TIR). The outer surface 707 of window 701 lies against the surface 705 of skin 725, and the index matching medium oil lies in a thin film between the two. Consider an arbitrary source point 703 on the surface 705 of the skin. This point will reradiate light, shown symbolically as rays 721, and in particular ray 711. If ray 711 meets the inner surface 713 of window 701 at an angle 709 which is less than the critical angle where total internal reflection takes place, then it will be reflected as ray 715 back onto the skin surface 705. The rays 721 symbolically illustrate that this can occur for a range of angles to produce reflected rays 723, illuminating a range of skin 719 located some distance from the source point 703. The region 717 adjacent to the source point is substantially free of such reflected light because to reach this region the equivalent angle of incidence on the inner surface 713 would not meet the criterion for total internal reflection. The critical angle of total internal reflection depends on the refractive index of the window 701. Thus it may be seen that the TIR effect has substantial range. (Other internal reflections can be reduced by rendering the side edges of all windows absorptive and non-radiating, but the TIR effect remains.) The effect does attenuate with distance because the reflection path is longer, but research has shown that it still may be easily discerned for a distance several times the thickness of the window 701. We have found that using a thick window produces a uniform TIR illumination effect. Given that the targets 727 are located on the surface 707 of the window 701 and are permanently in the field of view of the camera, this effect may be discerned and measured at the targets 727 in the corners of the field of view in order to standardize images taken. The effect will be dependent on the image in the field of view, but some compensation for it may be achieved by measuring the effect at each target 727 and applying a correction linearly interpolated from the four corners of the image across the whole image. In order to have a uniform TIR effect that can be compensated, we have found that, unlike the prior art researchers who favoured thin glass windows, a thick window of at least 4 millimeters is useful, and at least 5 millimeters is preferred.

FIGS. 11 to 24 are high-level flow charts illustrating steps in the operation of the overall system. The flow charts do not include standard steps that are well known to system designers such as an option to cancel out of the current flow and return to a top menu to allow a novice user to recover from an error. Also not shown are various checks automatically performed by the software at various stages to ensure the integrity of the imaging and of the database, and the availability of backup for the removable storage means 191 (FIG. 5); such routine administrative functions are well known.

Figure 11:
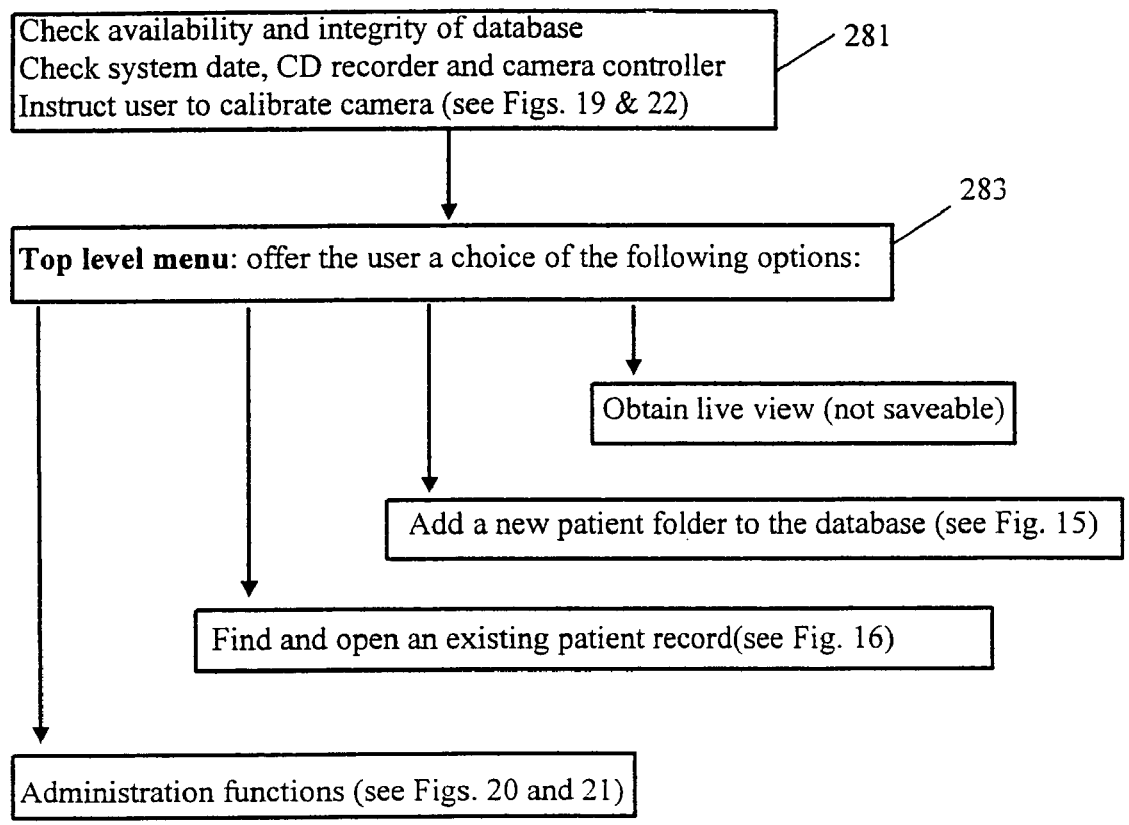
FIG. 11 is a high-level flow chart depicting the system operation.
Figure 22:
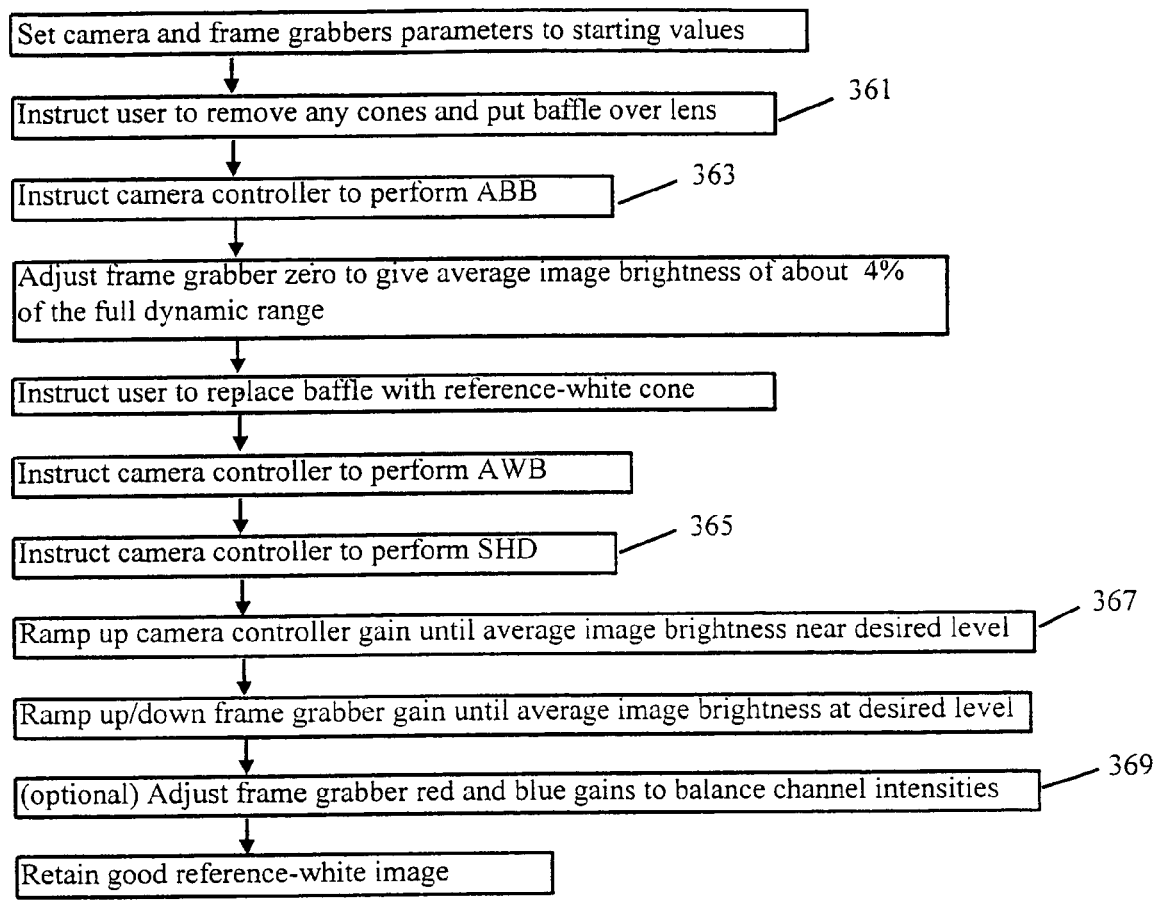
FIG. 22 is a flow chart illustrating the steps involved in a full camera calibration (black & white calibration)

The system operation starts as illustrated in FIG. 11. In step 281 a number of checks are performed as shown. These include a full camera calibration as shown in FIG. 22, and taking a reference-white image and checking it as detailed in FIG. 19. The user may also be advised that it is time to perform the archive task or to complete a backup. These ensure that the magnetic storage means 189 (FIG. 5) does not exceed its capacity and that copies of patient data will survive any computer hardware failure. Normally the backup task is performed when a patient record is closed as will be described in connection with FIG. 16, but the user can defer this if desired. After these checks are performed, the system software progresses to step 283, where the user can control four possible actions.

Figure 12:
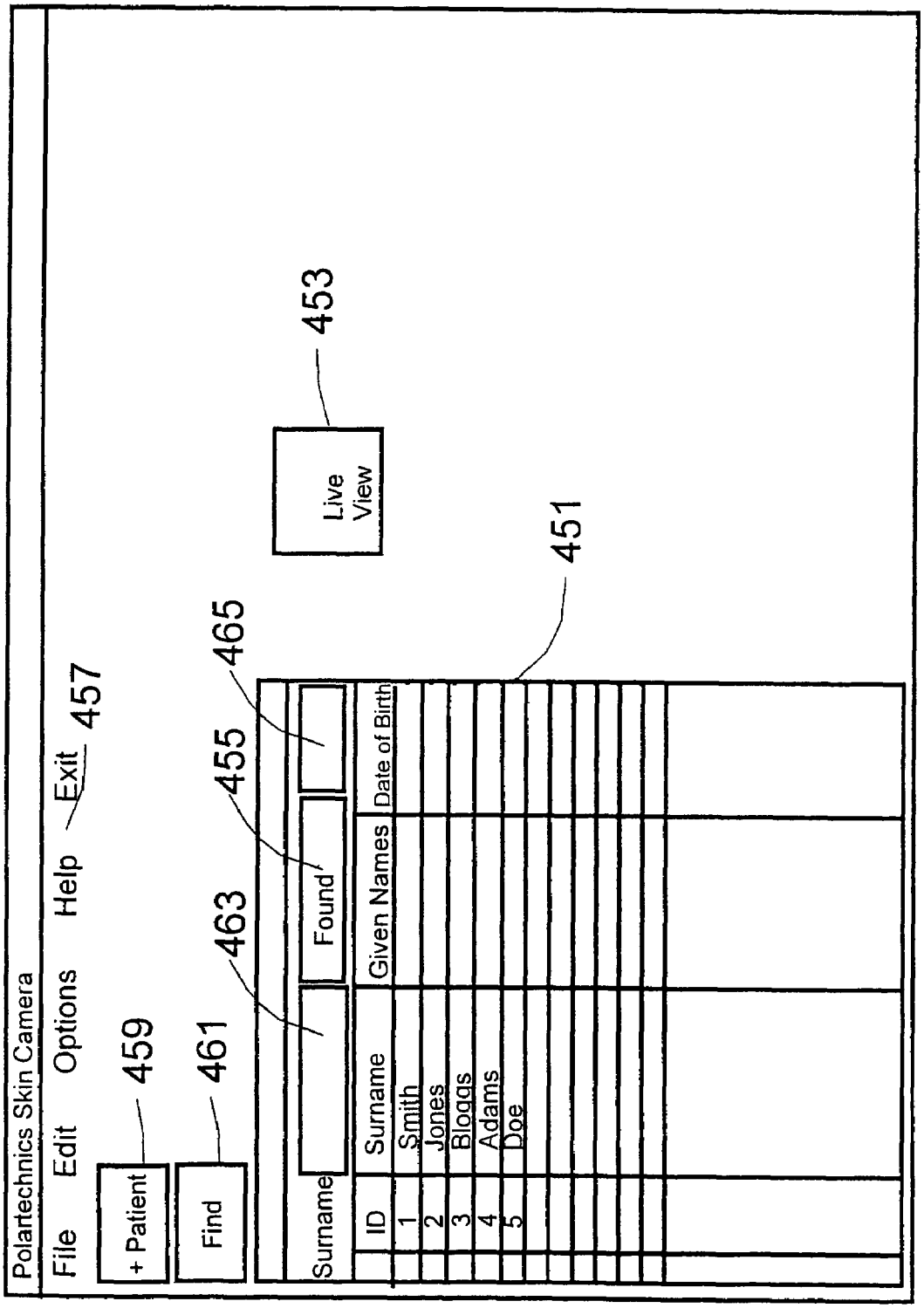
FIG. 12 is a simplified depiction of the main software screens seen by the user, at the locate-patient stage of operation.

The resulting state is known as the main menu. The appearance of the monitor screen 107 at this stage is shown in FIG. 12. This screen is one of two presentations of the main screens available to the user, the second being shown in FIG. 13. It should be noted that both screens will feature small or large changes as the user invokes various operations.

The "Obtain live view" option is activated when the user clicks with mouse 109 on the "button" 453 (FIG. 12), in the normal manner well known to those accustomed to the use of "Windows"-type operating systems. This places a live view image from the camera 131 in a separate window in the middle of the screen, and allows the user to demonstrate the system or to obtain a quick preview of a suspect lesion without having to create a new patient record or access an existing patient record. However, by design this image cannot be saved in the database. When the user is finished with the live view it is cancelled, returning the screen of the monitor 107 to the state shown in FIG. 12.

The user can "Add a new patient" by clicking on the button 459. The system will then take the user through the process shown in FIG. 15, creating a new patient record. [A patient record is simply a collection of images and data for a particular patient.] To "Find and open an existing patient record" the user may enter the patient name in area 463 and then click on button 461. Alternatively, the user may scroll through the displayed patient names in the table in area 451 and select one by clicking on the appropriate row. Having located the desired existing patient name or having just created a record for a new patient, the name will appear in area 463 and the Date of Birth in area 465. Clicking on the Found button 455 will cause the system to follow the procedure shown in FIG. 16. This will lead to a screen with the general appearance of FIG. 13.

It is also possible while in the state shown in FIG. 12 to invoke various Administration functions from the menu bar 457. These are outlined in FIGS. 20 and 21 and discussed later.

Figure 13:
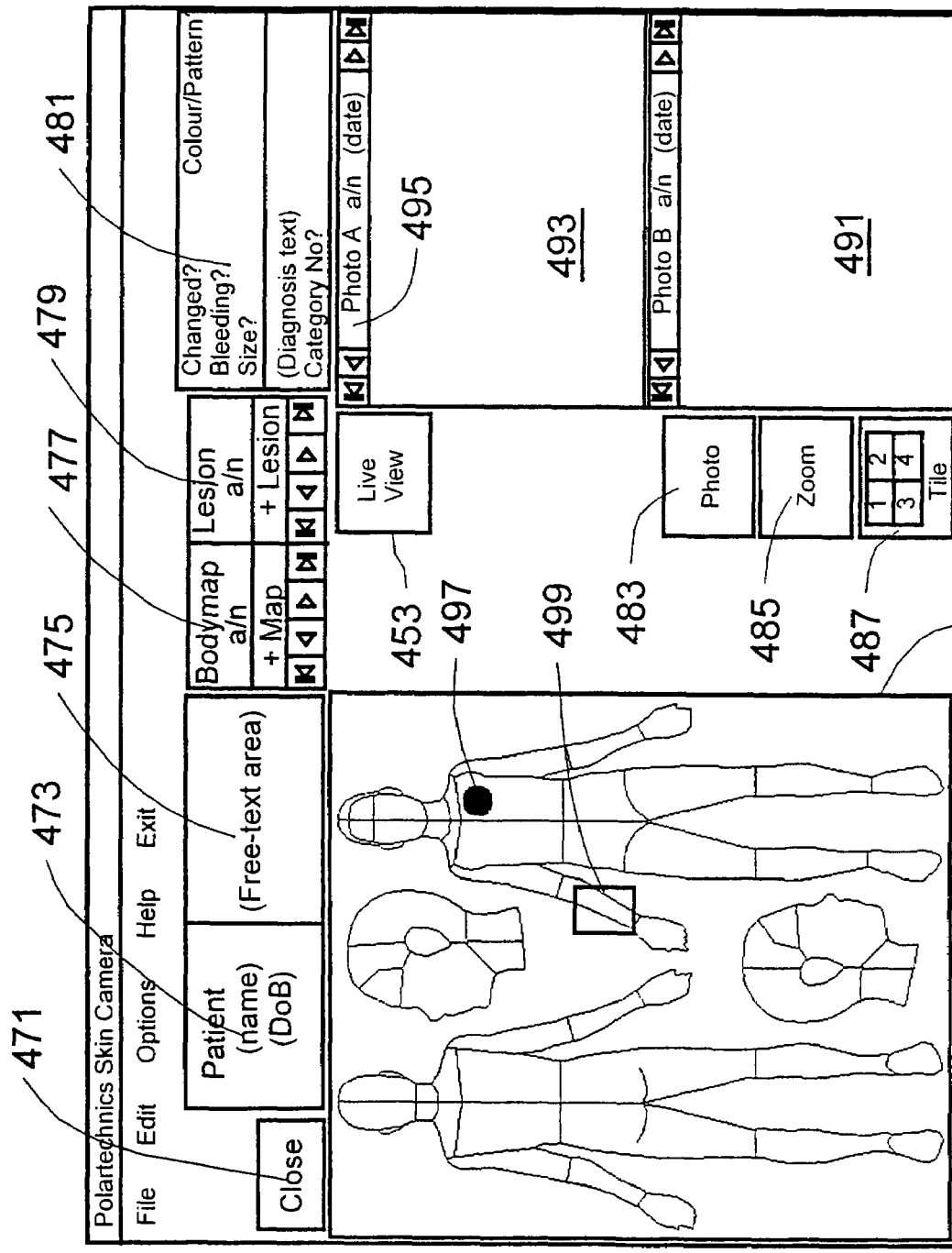
FIG. 13 is a simplified depiction of the main software screens seen by the user, displaying details including images for a patient.

The screen shown in FIG. 13 contains several major functional areas. The table 451 of FIG. 12 is replaced by the map 489, in the same area. This map may show the default (pictorial) bodymap for that patient or a photomap if one exists. At first entry the default bodymap will be displayed. If any lesions exist on this map they will be marked by a dot 497; the dot is red for a suspect lesion and blue for a lesion which has since been excised. If any photomaps are available for this patient they will be marked on the default bodymap as a square 499. Multiple dots and squares may be seen on the map although only one of each is shown in FIG. 13.

If there are any lesions on this map, then the first recorded lesion site will be made the "current" lesion site as shown in step 295 on FIG. 16. Text data entered by the user for this lesion will be displayed in box 481. The "Lesions are displayed" routine shown in FIG. 17A is then performed. This places the latest image for the current lesion in Photo B which is area 491 in FIG. 13, and if more than one image of the current lesion site exists, the oldest image is placed in Photo A, which is area 493. Photo B will be made the "current Photo". Either Photo may be made "current" by clicking on it. The other photos for the current lesion site may be accessed by clicking on the arrow buttons in the "bar" 495 at the top of the current Photo, thereby incrementing or decrementing the photo number. The bar 495 also contains text shown as "a/n": the "a" indicates which photo from those available for this lesion site is displayed, while the "n" indicates how many are actually available for this lesion site. The date of record for the image being displayed is also shown in the bar 495.

The initial simultaneous display of oldest and latest images for the current site immediately allows the user to see if any significant changes in the appearance of the lesion have occurred. Significant changes are an indication of malignancy. The ability to scroll through the n images for the current lesion site allows the user to observe the changes in time.

If more than one lesion site is shown on the map the user may access them in several ways. The first is to click on the appropriate dot 497 on the map 489. This will make that lesion site current, triggering the "Lesions are displayed" routine in FIG. 17A again. Alternatively, the user may step through the lesion sites by clicking on the arrow keys in the lesion box 479. This box also contains an "a/n" indicator for how many lesion sites are located on the current map (n) and which one (a) is current. If the default bodymap is current in window 489, then the existence of optional photomaps is indicated by squares 499 on the bodymap. The available photomaps may be scrolled through using the arrow buttons in the map box 477 or they may be accessed directly by clicking on the appropriate square 499. It will be noted that the methods of access to maps, lesions and images are essentially the same for ease of operation.

Figure 16:
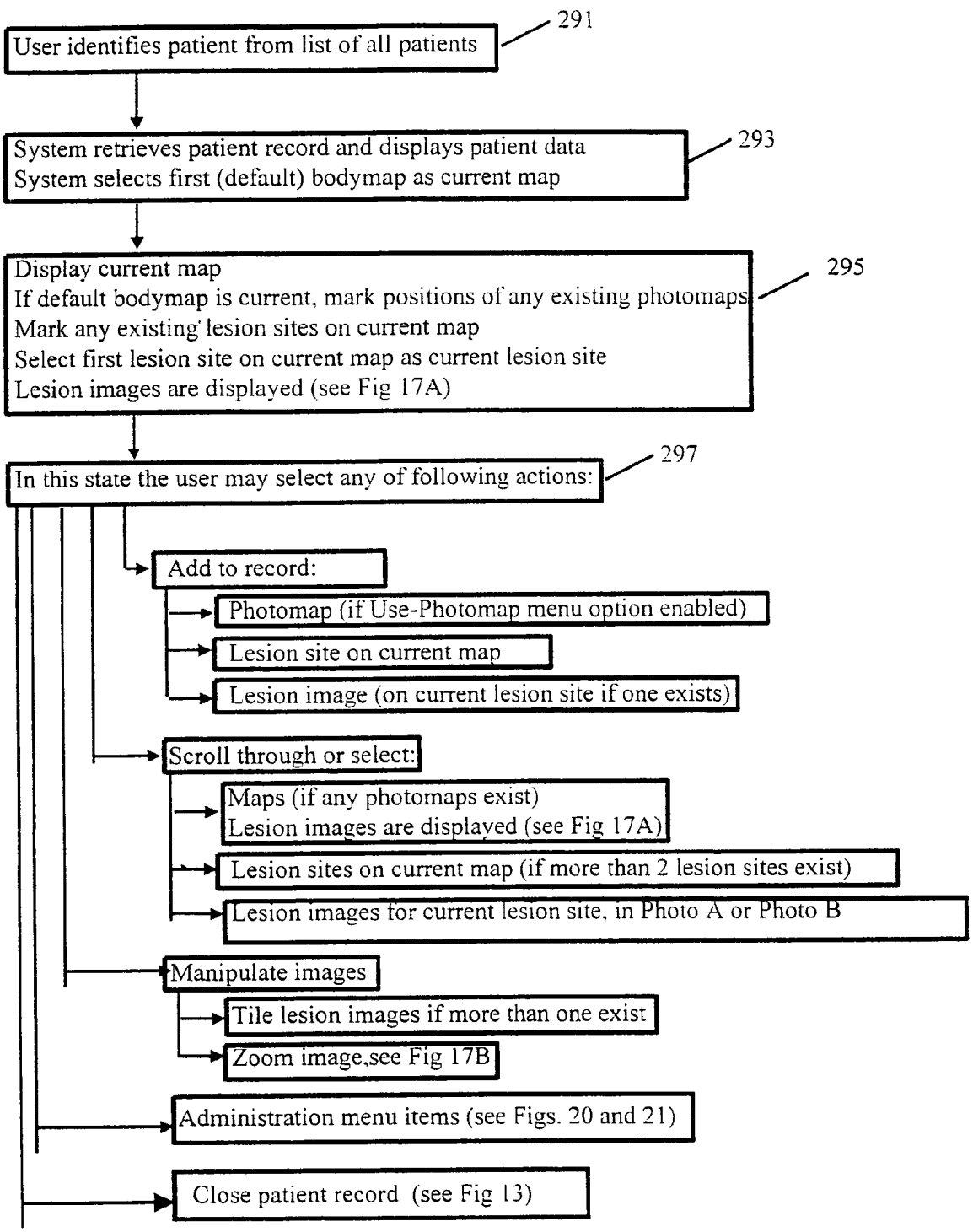
FIG. 16 is a flow chart showing processing of data of a patient already included in the database.
Figure 17A:
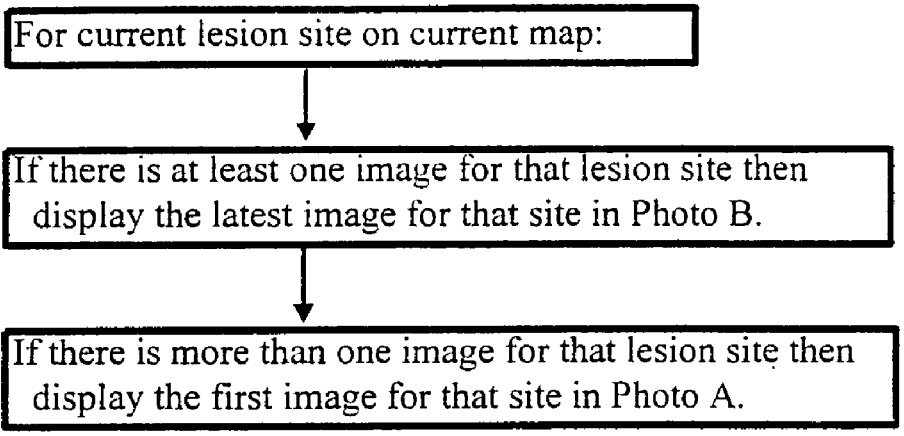
FIGS. 17A and 17B depict two flow charts of routines that may be invoked for displaying images of lesions.

The above description applies to the "Scroll-through or select" option in FIG. 16. In general, scrolling is done with the arrow keys, while selecting is done by clicking on a map.

It will be seen that the major difference between the two screen images is that, absent a current patient, the default bodymap of FIG. 13 is replaced by a patient selection menu in FIG. 12. The relatively fixed screen layout enables the user to see at a glance all relevant information and possible actions.

Figure 15:
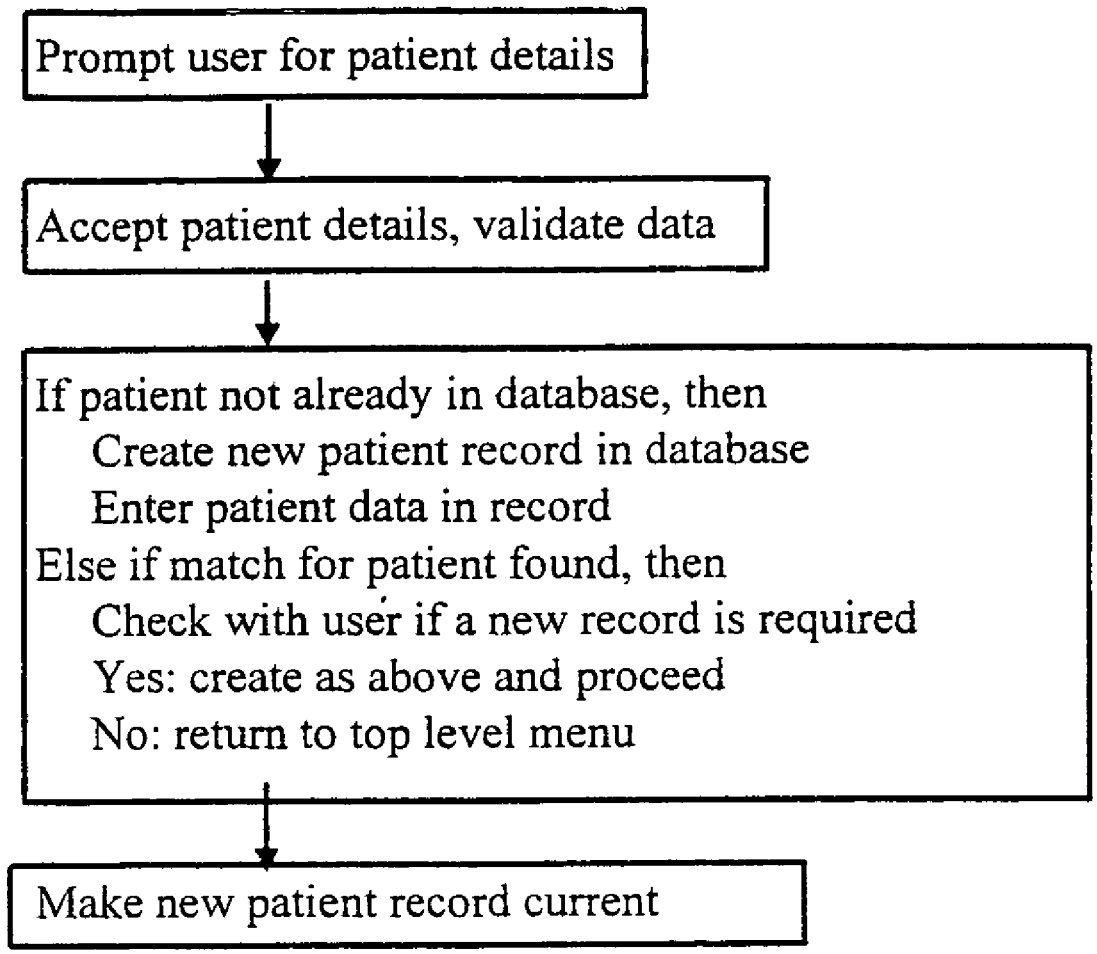
FIG. 15 is a flow chart showing how a patient is added to the database.

The first option in FIG. 11 is to place a live view on the screen of what the camera in the hand-held unit 103 sees. This is useful for preliminary investigation, training and demonstrations and is invoked by clicking on button 453. As discussed above, the image taken at this stage can not be saved. The second option is to add a new patient record to the database by clicking on button 459. This creates a new entry in the patient table in the database, provided that there is no match with any existing entry. As shown in FIG. 15, in the event that the user has just created a new patient entry by exercising the second option, he is prompted for data for that patient. The third option is to select a patient (record) from those already in the database, by either entering part of the patient name in box 463 or scrolling down the list of patient names as shown in area 451. Once the user has selected a patient, the system accesses the data for that patient and a range of further options becomes available. The fourth option gives access to various administrative functions, as detailed in FIGS. 20 and 21.

Figure 14:
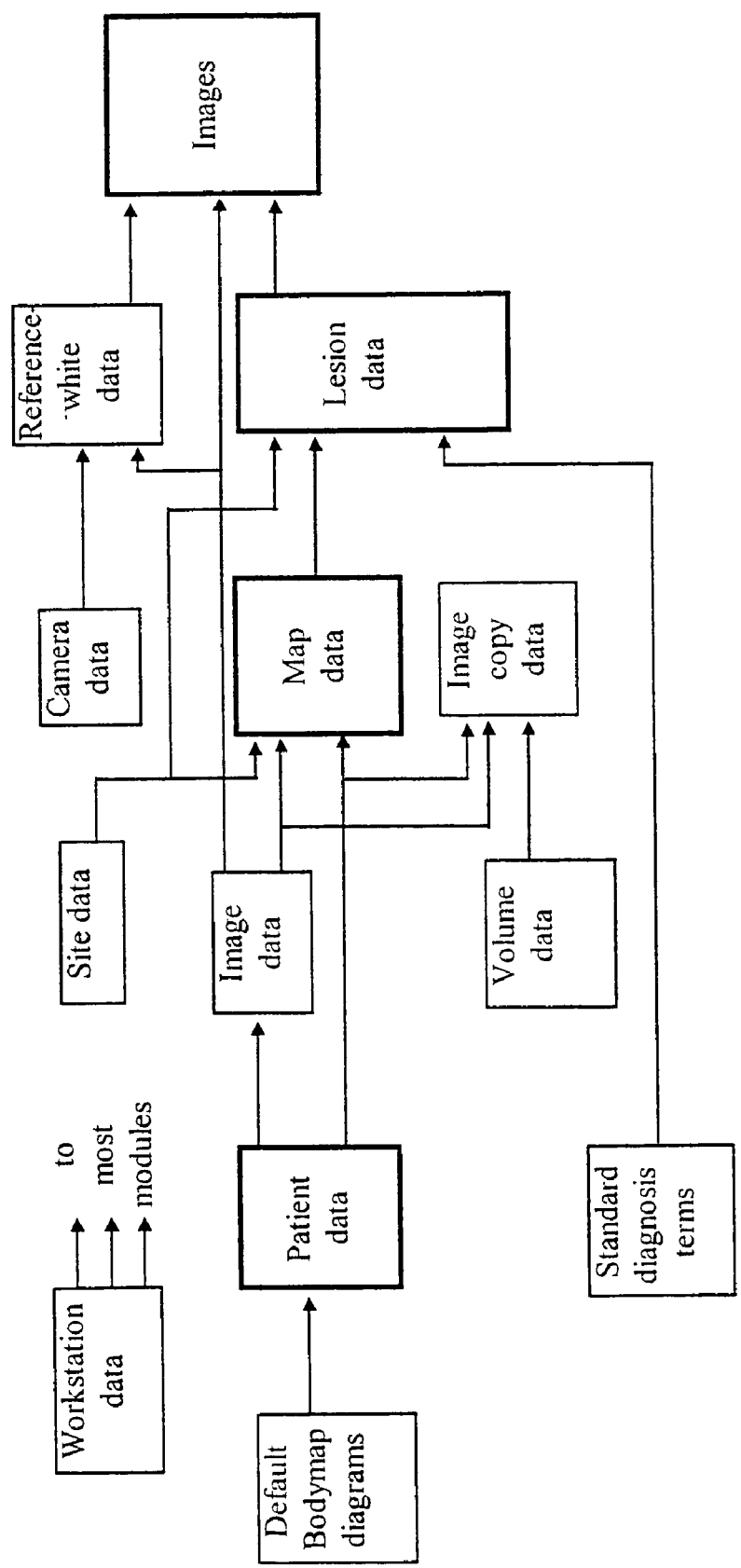
FIG. 14 shows the simplified structure of the underlying database.

FIG. 14 represents the structure of the database underlying the system. The database complies with the relational database model and is made up of a number of tables with linkages as shown. Four tables with heavy outlines—patient, map, lesion, and image—are the tables most obvious to the user. The patient table contains all the text data about each patient. The map table contains the data about all the photomaps applicable to each individual patient; for each patient, what is termed map zero is the relevant default bodymap. There may be several possible bodymap diagrams in the system, but only one of these will be linked to any patient as that patient's default bodymap. On the other hand, one default bodymap diagram may be linked to multiple patients as the default; it is not necessary to save a separate copy of the default bodymap for each patient. This permits, for example, one user to use only one generic asexual default bodymap, while another user may prefer to use generic male and female default bodymaps. The lesion table contains all the data about a lesion, and each lesion is linked to a map. Thus access to any lesion must be through the relevant map. The image table contains the data for each image, and can only be directly accessed through the lesion table.

It should be noted that the image table does not have to actually contain the images themselves. The images are stored outside the main database file as separate files in order to minimise the size of the main database file and maximise the speed of data retrieval.

While FIG. 14 illustrates the underlying database structure, the structure seen by the user is different. The data is conceptually organised into "records", encompassing text data and images, with a record for each patient. There are a number of other tables in the database. The reference-white table contains data about the reference-white images. The camera data table contains the camera settings for each reference-white image. There is a one-to-many relationship between records in the camera data table and the reference-white table.

The site data table contains descriptive labels for various areas within the default bodymap and is used to provide familiar text feedback to the user about the placement of lesion and photomap images. The workstation table contains information about the physical hardware and forms in essence an ID code or serial number for the system. Reference is made to it by most other tables. It may contain more than one entry as it is possible for hardware elements to change during the life of the system. For example, the camera might be replaced.

The table of standard diagnosis terms shown in FIG. 14 is accessed through the lesion table. A lesion may have one diagnosis entry, but many lesions will have no diagnosis entries. A particular case of this is where the user takes follow-up images of a lesion site after the lesion has been excised for the purpose of monitoring success. The user may enter free text about the lesion in the free text box 475 (FIG. 13). The standard diagnosis terms table lists medically standard descriptions for various lesions, e.g., "malignant melanoma", "basal cell carcinoma", etc. One of these standard diagnoses may be selected for the lesion site by filling in the "Category No" in box 481; the text description for that number will be displayed in the same box 481.

The three tables image data, image copy data, and volume data are part of the internal database structure. The image copy data table contains data about where copies of images are to be found—on the magnetic storage means 189 or on a removable storage means 191 (FIG. 5). The hardware (drive) for the removable storage means 191 is able to handle many volumes of storage (e.g., zip disks or CD-ROM disks) and each one has a unique label. The volume data table contains data about each of these, and this data is referenced by the image copy data table. Finally, the image data table contains internal linkage information about each image, including whether copies have been made on the removable storage means 191 and whether a copy still exists on magnetic storage means 189.

Database structures are well known in the art. What is unique about the database structure in our invention is the association maintained between the three types of images—the reference-white image, the skin image and the raw lesion image. (By "raw" images is meant the unprocessed data as read from the camera.) All three are needed to provide calibrated images and automatic skin/lesion boundary identification. By storing all three together, all possible methods of quality control and image analysis are preserved for future research use and improved image processing techniques. When reference is made to copying an image, it refers to handling all three together, as a triplet, even if the reference white image serves multiple lesion images.

FIG. 15 illustrates the procedure to add a new patient to the database. The user first enters the patient's name and date of birth, and this data is then validated, i.e., complete identification data must be entered. The system then checks existing entries to see if this patient has already been entered into the database. This is to avoid the well-known problem of duplicate entries found in many database systems. If there are no matches with existing patient entries, then a new patient record or entry is created and the data entered by the user is placed in that record. If a match is found with an existing entry or patient, then the user is asked to confirm that a new record should really be created; it is possible for two patients to have the same name and date of birth. If the new entry is rejected, control returns to the top level menu. In the last step, the new record is made "current."

FIG. 16 illustrates the procedure for accessing data for an existing patient. In step 291, the user identifies the required patient either by entering the patient name or by scrolling through a list of entries. If the user has just been through the actions shown in FIG. 15, then the system will already be displaying the basic details for the current patient/record, and the user may accept this patient/record. With the required patient identified, the patient record is made current, as shown in step 293.

Figure 6D:
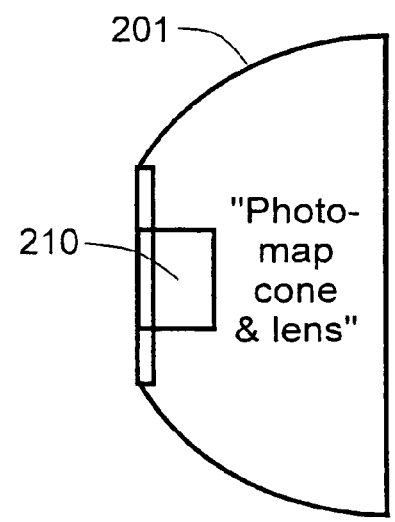

As discussed above, there are two kinds of maps. The first, a bodymap, is a generic drawing of a human body, as shown in FIG. 13, on which two different types of marks may be found. The first type of mark (dot) indicates the location of an individual lesion for which a respective image is available. Clicking on a lesion mark of this type brings up the lesion images in Photos B and A. The second type of mark (square) identifies a part of the body, of which a photomap image has been taken with photomap cone 201 (FIG. 6D). Clicking on this photomap mark brings up the photomap so the user can see the overall region of interest. On a photomap, an actual image of the patient's skin, there are lesion marks indicating individual lesions. Clicking on one of them brings up the respective lesion. Initially, the default bodymap for the selected patient is made the current map.

In step 295, the current bodymap is displayed. Any photomaps recorded for this patient are marked on the bodymap display with the appropriate distinctive square icon or photomap mark, and any lesion sites recorded for this patient on the bodymap are also marked on the bodymap display with the appropriate distinctive dot icon or lesion mark. The (x,y) coordinates of the site within the map are recorded in the database. When either the default bodymap or a photomap is displayed, the dots and squares are added to the display at the appropriate (x,y) positions. These dots and squares are not stored in the map images. With this done, the "lesions are displayed" routine as shown in FIG. 17A is executed. If there is at least one lesion recorded on the bodymap, then the first recorded lesion is made current and the latest image taken of that lesion is displayed in Photo B on the screen. If there is more than one image of the current lesion, the first image taken of that lesion will be displayed in Photo A. This "lesions are displayed" process will occur whenever the user alters the selection of the current bodymap or the current lesion.

In step 297, the user has several choices of action—to add to the record, to scroll through the record, to manipulate images, or to perform administrative functions.

Figure 17B:
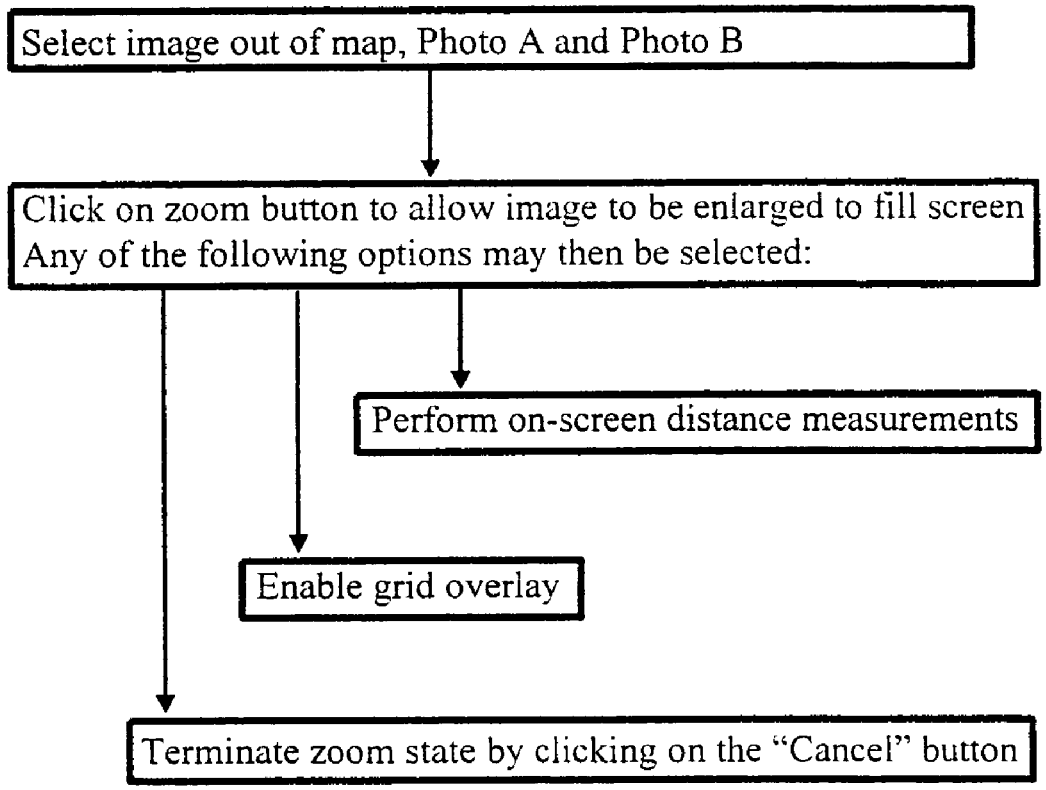
Figure 18:
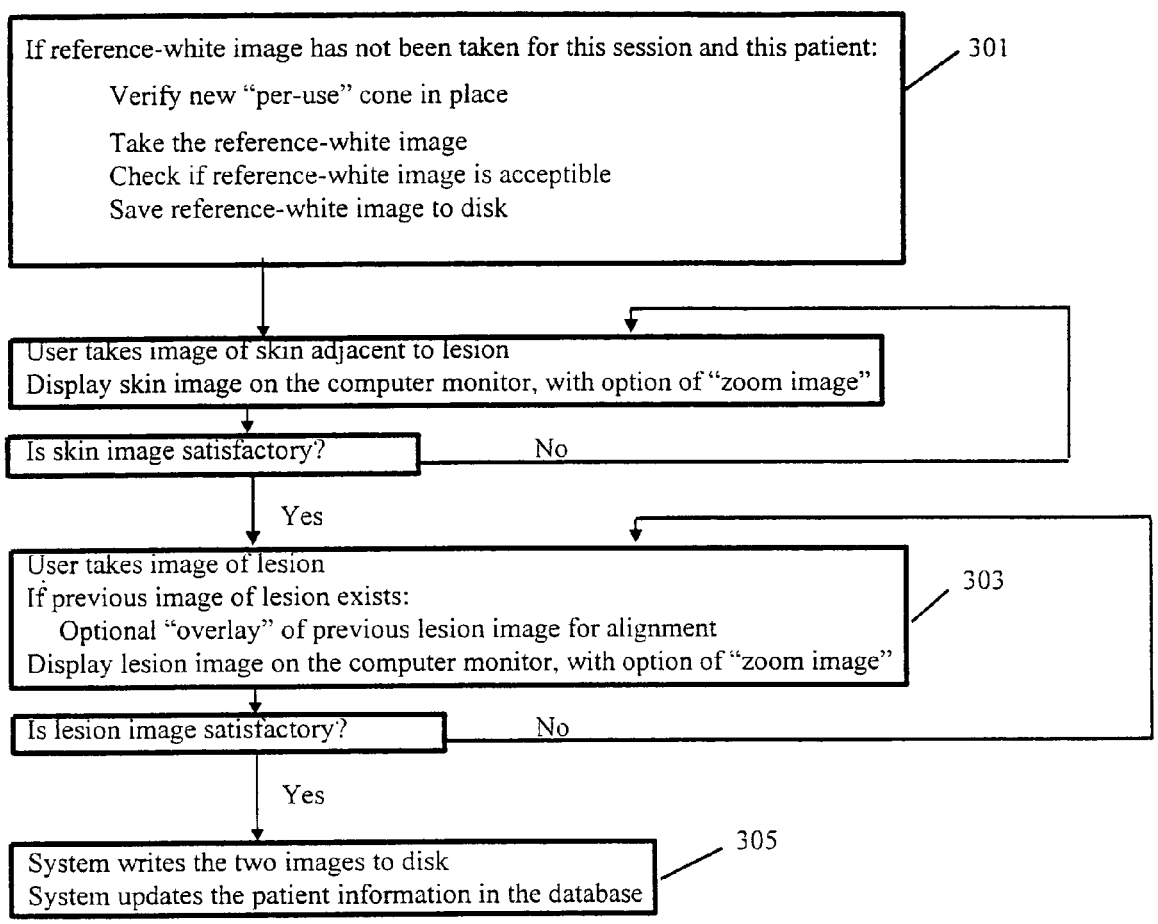
FIG. 18 is a flow chart showing how a new lesion image is added to the database.

The "add to record" option allows the addition of a photomap if this action has been enabled (option 341 in FIG. 21) and the bodymap is current, the addition of a lesion site to the current bodymap, and the addition of a new image of the current lesion (the details of which are shown in FIG. 18). Adding a new photomap and adding a new lesion site are done by clicking on the appropriate "+Map" and "+Lesion" buttons in boxes 477 and 479 (FIG. 13). For a new photomap, the user is then instructed to change to the wide angle cone 201 and to take the photo. The user gets the option to zoom the image to full-screen size (FIG. 17B) prior to accepting it. In each case the user is required to click on the appropriate spot on the map 489 to define the location. The system then displays the appropriate mark on the map 489 at that location.

Figure 21:
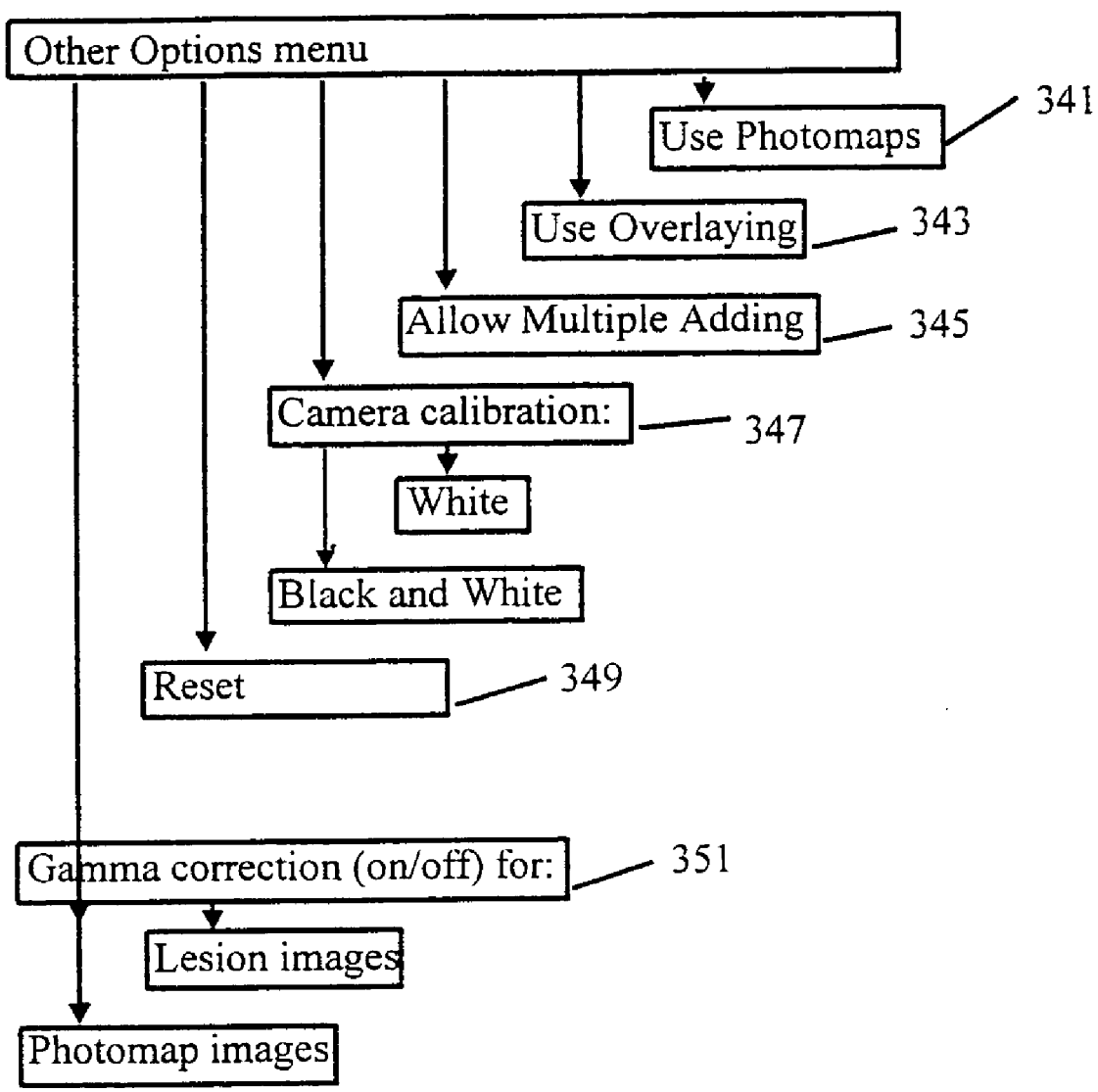

There is a special multiple adding option which can be enabled as shown in FIG. 21. This option allows the user to add a lesion image (plus the accompanying skin image) to each lesion site for a patient. The system cycles through all recorded lesions for the patient and prompts the taking of new images for each.

Figure 26A:
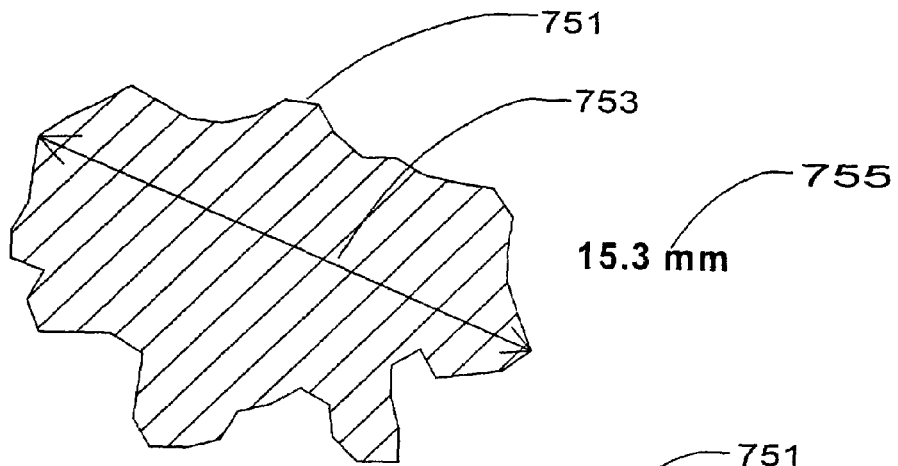
FIG. 26 illustrates the on-screen measurement facilities.
Figure 26B:
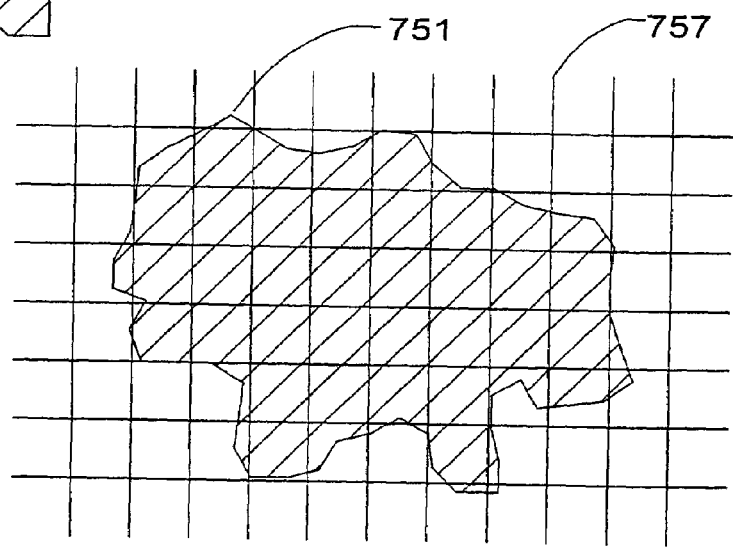
Figure 26C:
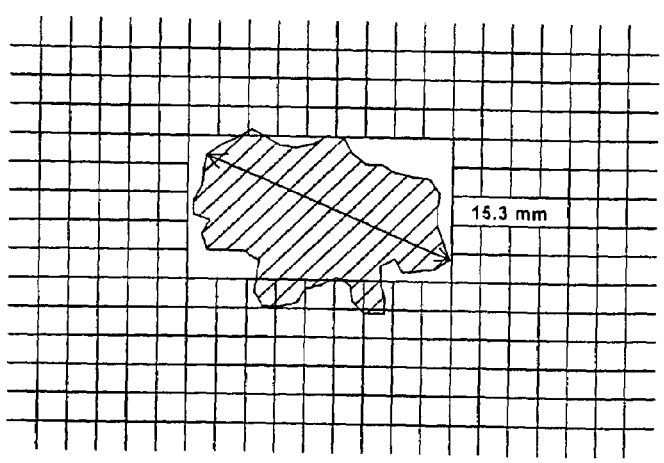

The "manipulate images" option in FIG. 16 allows the user to "tile" images or to "zoom" an image (FIG. 17B). Tiling means to fill the screen with up to four lesion images for the current site, in a 2 by 2 array and is invoked by clicking on button 487 (FIG. 13). This also allows for historical comparison of images of a lesion site to gauge growth or change. Zooming takes a single image up to the highest resolution provided by the camera. That is, all pixels from the camera are displayed. Measurements may then be made of a lesion feature, as shown in FIG. 26A, by clicking once at one side of the feature and then again at the other side. This will draw a line 753 on the screen between the two points and display the distance between them, as shown by the numeral 755. After the distance is displayed, clicking on the distance text will select it and allow it to be moved to any location on the screen where it will not obscure the features the user is examining. Also, as shown in FIG. 26B, it is possible to place a fine grid 757 over the image, with the lines at, say, 1 mm spacings. The two options may be combined, as shown in FIG. 26C. Zooming may be done on the image in Photo A or Photo B using button 485 or from one of the images in the tiled display. Cancelling a zoomed display deletes the measurement line 753, but going back to the tiled display retains the measurement line in the displayed version of the image. This is also useful for comparing images of a site on a historical basis. Although not illustrated, on-screen controls allow the grid to be rotated and shifted in order to facilitate measurements.

The patient record may be closed by clicking on button 471, removing all patient details from the screen to protect patient confidentiality at the end of a session. When this is done the system attempts to backup the main database file and the new images taken in the session for this patient to a small removable storage means 191 such as a "Zip disk". The user may defer this backup process to a more convenient time, but the system will not lose track of which images have yet to be backed up. The user will be prompted at later times about this.

The edit menu item found in the top bar 457 (see FIG. 12) permits the user to correct erroneously entered workstation or patient data, including photomap and lesion positions. This option requires the user to enter a valid password before taking effect, for security reasons.

The fourth option in FIG. 16, involving administration menu items, will be discussed below.

Figure 19:
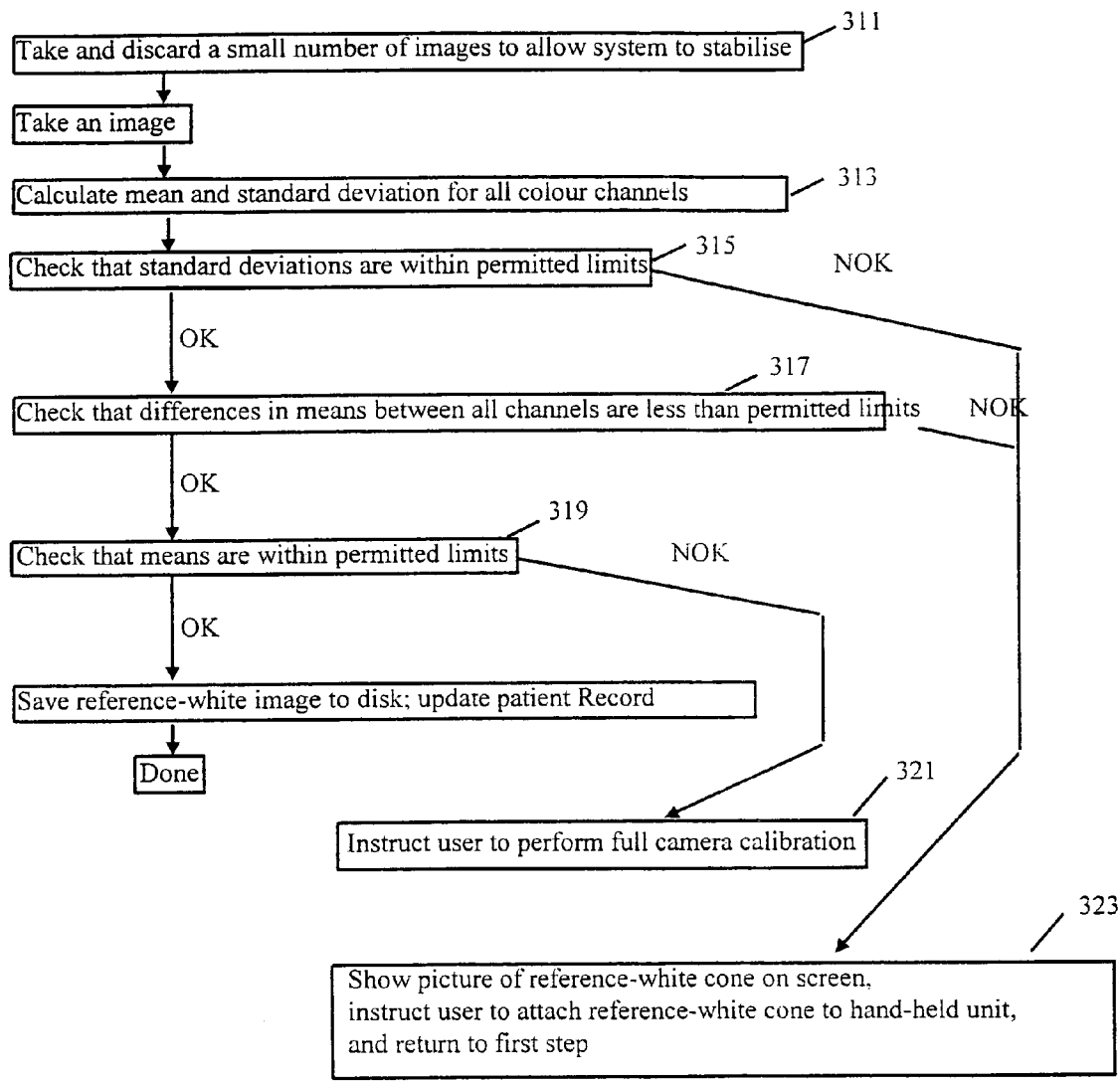
FIG. 19 illustrates the steps involved in performing a routine reference-white check.

FIG. 18 shows the steps involved in acquiring an image of a lesion for possible retention. This is done by clicking on button 483. Several actions will have already been performed by the time this routine is executed—the user will have already either created a new patient record as depicted in FIG. 15, or accessed an existing patient record as depicted at the start of FIG. 16. If a photomap (as opposed to the default bodymap) is required, this will have been displayed; and the user will have selected the lesion site of concern. However, as part of the emphasis on image quality, a dedicated reference-white image is required for every patient in every clinical session. The reference-white image is saved to disk in the patient record. As shown in step 301 of FIG. 18, a check is made that a new "per-use" window is in place on the cone, and if a suitable reference-white image has not been taken for the current session and patient, then the system ensures that such an image is first taken, checked and saved if necessary, all as shown in FIG. 19. In the next step, an image of skin adjacent to the lesion is taken. This image is taken by pressing the standard window 147 (or the narrow window 205 if it is to be used) against the skin of the patient in a region adjacent the lesion site of concern. The image is displayed in a separate frame which the user may position anywhere on the screen using the normal "click and drag" Windows method. This image may also be zoomed for checking as shown in FIG. 17B. The user then has the option of repeating the process of acquiring the skin image if the current one is not satisfactory.

In step 303 an image of the lesion is taken. In the next step the user has the option of repeating the preceding step if the lesion image is not satisfactory. Once a lesion image has been acquired, it may be treated in the same way as an old lesion image may be treated in step 297 of FIG. 16.

In step 305 the system saves the skin and lesion images in the patient record for the current lesion site. The database information in the patient record is also updated.

FIG. 19 shows the steps in acquiring and checking the reference-white image. This is crucial to the quality of the colour imaging, and is necessitated by the possibility of variations in both the intensity and colour temperature of the light source such as the quartz-iodine lamp in the illuminator 121, and in the intensity and uniformity of the illumination field created by the illumination sources or optical fibre bundles at ports 153. At entry to the reference-white image routine of FIG. 19, it is assumed that the reference-white cone 207 is already on the hand-held unit (as a result of the full camera calibration process initiated at start-up as in step 281 of FIG. 11).

In step 311 a small number of images are acquired by the frame grabber and discarded. This ensures that the frame grabber has time to synchronise with the camera controller. This step is not essential with all types of frame grabbers. In the next step an image of the reference-white window 209 is acquired. In step 313 the mean and standard deviation of the whole image is calculated, and in step 315 the standard deviation of the image is compared with predetermined upper limits for each colour channel. This checks for gross aberrations in the lighting and the reference-white window 209. In step 317 the differences between the means for all colour channels are calculated and compared with predetermined limits. This checks for correct colour balance. In step 319 the intensity values for each colour channel are compared with predetermined upper and lower limits. This again checks the lighting and the reference-white window 209. As an option, the reference-white image may also be compared to the last reference-white image recorded, and if sufficiently similar this latest reference-white image may be discarded and the last reference white used in its place henceforth.

Should either of the tests in steps 315 or 317 fail, it will probably be because the reference-white cone 207 is not on the hand-held unit. In this case, step 323 shows the user a picture of the reference-white cone and instructs the user to attach it to the hand-held unit. When the user signals that this has been done, the whole process is restarted at step 311. It is also possible for the user to cancel this process and to initiate a full camera calibration as depicted in FIG. 22. If the test in step 319 fails, the user is instructed in step 321 to perform a full camera calibration.

Figure 20:
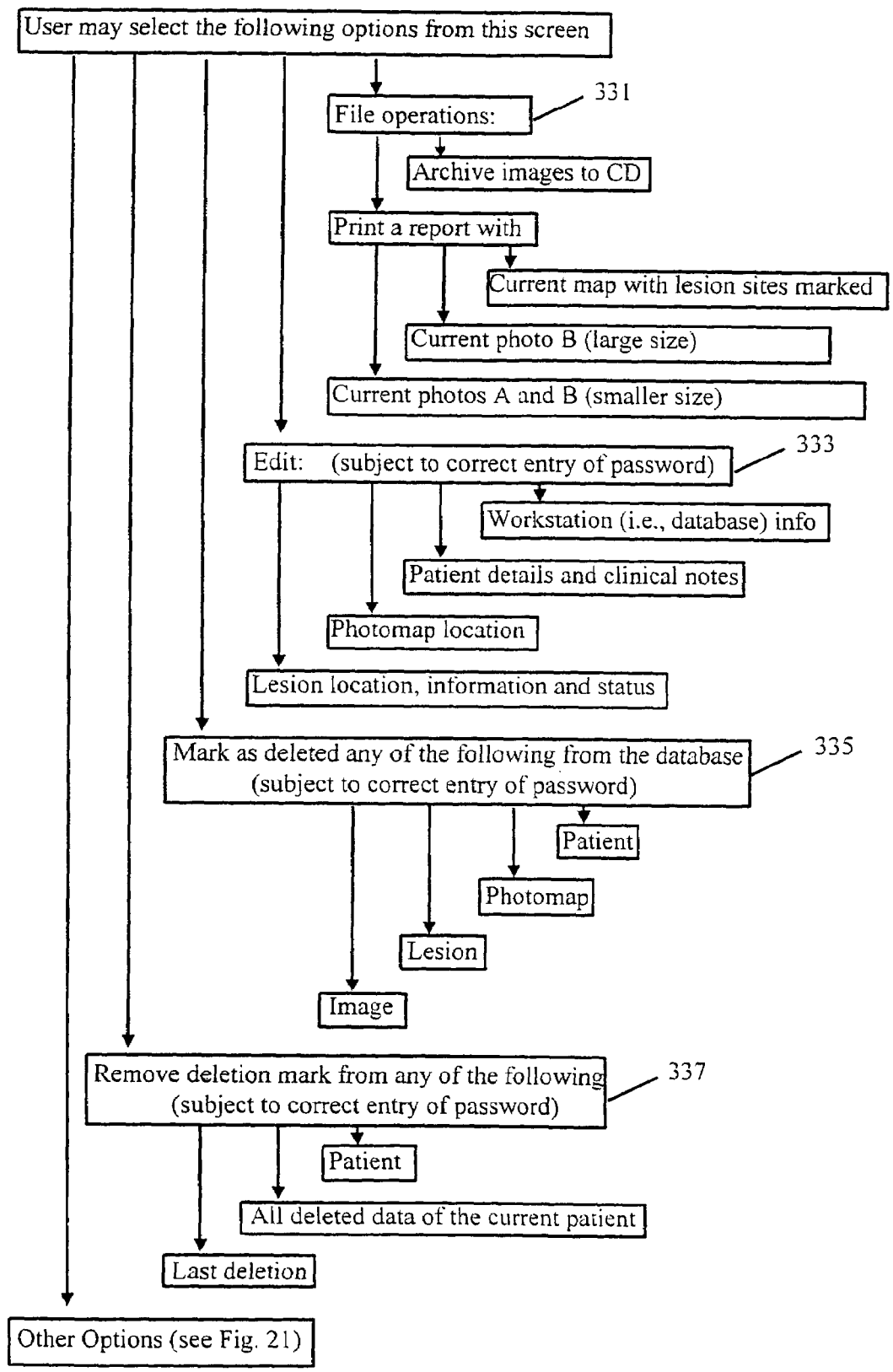
FIGS. 20 and 21 are flow charts illustrating the administrative-function options available to the user.

FIGS. 20 and 21 shows a range of administrative functions typically needed for system maintenance. The "File" category 331 covers archiving images onto removable storage means 191 (FIG. 5), typically a writable CD-ROM disk, from the magnetic storage means 189, and the printing of reports on the patient. The report will include patient details and an image—either the current bodymap image with lesion sites marked, the current image in Photo B, or the images in Photos A and B.

The "Edit" option 333 allows the user to modify existing information in the database, but access to this option is restricted by the use of a password. The intention is partly to emphasise to the user the need to be careful when altering data. Data which may be altered includes details about the workstation, patient details and clinical notes, photomap position on the default bodymap, and lesion position, information and status. The last refers to the possibility that a lesion may have been excised since the image was taken.

The "Delete" option 335 allows the user to delete a range of entries from the database, again subject to the correct entry of a password. The entries which may be deleted include a whole patient record, a photomap and all lesion sites and lesion images accessed through that photomap, and a lesion site and all images for that lesion site. When deleting a lesion image, the matching skin image is also deleted. The reference to the matching reference-white image is also deleted, but since one reference-white image may be associated with several lesion sites the reference-white image itself is not deleted. It should be noted that the term "delete" here actually means that the database entry is marked as "deleted"; it is not actually physically removed from the database but it is marked as removed and can be recovered if necessary.

The "Undelete" option 337, again subject to the correct entry of a password, reverses the deletion process by cancelling the "deleted" mark on an entry. It is possible to undelete a whole patient record in one step. To do this, access to the record is gained by searching for the patient name in the "deleted" patient list. Such a search is possible from the menu bar 457 at the top of the Top level menu screen when in the mode shown in FIG. 12. It is also possible to undelete all deleted data for the current patient, and to reverse the action of the last deletion command on whatever entity was involved.

The "Other Options" category shown in detail in FIG. 21 covers a range of software switches and hardware adjustments. The "Use Photomaps" software switch 341 allows the user to include photomap images in the patient record. When this switch is off, the system only permits the user to mark the lesion site on the default bodymap, which is a generic drawing. When the switch is on, the user can take photomap images and mark their sites on the bodymap, and can similarly mark the sites of lesions on any of the maps (both photomaps and the default bodymap). Where a patient has only a few widely spaced lesions, the switch would normally be left off, but when a patient with a large number of closely spaced lesions is encountered, the switch would be turned on.

The "Use Overlaying" software switch 343 causes the old image in the current Photo to appear as a background to the new lesion image being taken, as an overlay or "ghost". This is done by combining equal parts of the old and new lesion images prior to display, and allows the user to align the hand-held unit on the patient's skin such that the new image has the lesion in the same position as in the old image. If there has been little change in the lesion the alignment may be easy; conversely, if the lesion has grown since the old image was taken the boundaries will have grown, making the alignment more difficult, but reasonable alignment is still possible in practice.

The "Allow Multiple Adding" software switch 345 allows the user to scroll through all the lesions registered in the database for a patient in a predetermined order and to add a new current image to each of these lesions. This allows a user to maintain a pictorial history of a patient's lesions very easily. With this switch off, the user can only scroll through the lesion images for the current lesion site.

The "Camera calibration" option 347 causes the camera hardware to be recalibrated. The "Black and White" calibration is performed when the software system starts running (step 281, FIG. 11), but it can be repeated at the user's will. The process is shown in FIG. 22.

The "Reset" option 349 allows the user to reset the frame grabber and the camera controller. This reset option is designed to perform a low-level initialisation of the imaging hardware and to restore known good instrument settings.

The "Gamma Correction" option 351 allows the user to alter the gamma correction applied to the displayed versions of the photomap images and the lesion images. Gamma correction is intended to correct the appearance of an image for the non-linear characteristics of the phosphors found in conventional cathode ray TV screens and computer monitors.

FIG. 22 shows the process for doing a full camera calibration. This process actually encompasses both the camera and the frame grabber. For the "Black and White" option of FIG. 21, the process starts with the user being instructed in step 361 to remove the cone from the hand-held unit and to place a black baffle over the camera lens. This gives a "black" image. The frame grabber zero and gain parameters are set to nominal mid-range values, the camera gain is set to 0 dB, and the camera controller 121 is instructed to execute an automatic black balance (ABB, step 363) process. Instructions to the frame grabber are issued over the main computer bus while instructions to the camera controller are issued via a serial link 185 (FIG. 5). The ABB instruction causes the camera controller to adjust its internal red, green and blue channels to give equal signal levels for the "black" image by variations in internal zero settings. The frame grabber zeros are then adjusted to give average image levels of about 10 units (out of 255). By offsetting (to 10) the image values for a "black" image in this way, it is possible to handle slight variations in black levels. If the "black" image values were set to 0, it would not be possible later on to detect and handle negative swings in the input signal as the frame grabber can not give negative results.

After the black levels have been adjusted, the next two steps set up the colour balance and the white level, and it is at this point in the process that the "white" option enters the process flow. The user is instructed to place the reference-white cone 207 (FIG. 6C) on the hand-held unit. Then the camera controller executes an automatic white balance (AWB). This causes the camera controller to acquire a "white" image and to adjust its internal red, green and blue channels to give equal signal levels by variations in internal gain settings. This feature of the camera controller is designed to compensate for variations in the colour temperature of the scene illumination. Then the camera controller executes an automatic shading correction (SHD) in step 365. This causes the camera controller to adjust its internal red, green and blue channel parameters to give equal signal levels across the "white" image by dynamic variations in internal gain and/or zero settings. This feature of the camera controller is designed to compensate for variations in the colour of an image due to deficiencies of the optical components inside camera head 131 (FIG. 1). Such deficiencies are a known problem even in high-quality 3-CCD video cameras. It should be noted at this point that the ABB, AWB and SHD adjustments may not be available in all colour video cameras, especially the cheaper ones, and that remote control of these adjustments via a serial link is a feature of only very high-quality colour video cameras. However, this refinement is necessary to get the highest possible image quality in the skin and lesion images.

Once the camera controller has successfully executed these adjustments, the setting of camera and frame grabber gains is performed. It is desired that the reference-white image have an average value near the top of the available dynamic range (0–255). The camera controller is directed to increase its overall gain in 1 dB steps (finer steps are not available in the unit used) and to acquire a new image each time until the average level of the reference-white image is near the desired level. It should be noted that this causes the gain in all three colour channels to rise equally, and it does not alter the apparent colour of the image. Then in step 367 the frame grabber overall gain is adjusted until the average reference-white brightness is at the desired predetermined level. This sequence is used because the range of gain adjustment in the frame grabber is usually less than that available in the camera controller but the gain steps available are much finer.

It is possible that after the above adjustments have been performed that the three colour channels may not give equal average values, despite the AWB process. This can be adjusted in some frame grabbers by small adjustments to the gains for the individual red and blue channels to cause them to give average results matching that in the green channel as indicated in step 369, but this is not essential.

At the end of the process the system has an acceptable reference-white image. This image is available for use as shown in step 301 of FIG. 18.

Image normalisation is performed on both the skin images and the lesion images. It is not performed on an image obtained with the photomap cone 201 of FIG. 6D as the lighting conditions for the latter are different. The principle behind normalisation is that the reference-white window 209 is a substantially uniform white surface. Since perfect materials do not exist, there is no "perfect white surface" which will reradiate light that is spectrally identical to the incident light. Such matters are well covered in the standard literature such as in *Color Science: Concepts and Methods, Qualitative Data and Formulae*, Wyszecki et al., $2^{nd}$ Ed., Wiley, NY 1982. However, for the purposes of our invention it has been found that an opaque layer of well-mixed good quality white paint is acceptably uniform. Thus any variations across the digitised image of the reference-white window will be due to variations in the illumination field. These variations in the light field will still be there when the standard window 147 replaces the reference-white window 209 for images of skin and lesions. Thus if a single pixel at position (x,y) in the reference-white image is measured by the frame grabber as having intensity W(x,y) which May be some percentage less bright than the average level $W_{av}$, it may be expected that in some other image the same pixel P(x,y) will be equally less bright. By normalising the pixels in an image by using the equation P'(x,y)=P(x,y)/W(x,y), it is possible to correct the image to appear as if the illumination field was substantially uniform, i.e., the lesion image will be more accurate. By way of example, it may be seen that normalising the reference-white image itself results in every pixel having a preset value. It will be obvious that the effectiveness of such normalisation is limited by the presence of electronic noise in the image signals being digitised. However, this introduces only a very short-range noise into the normalisation. Such noise may be somewhat reduced by applying a spatial filter to the reference-white image. Suitable filters include arithmetic averages and median operators performed over square areas or on vectors along the X and Y directions. The above explanation of the normalisation process is given for grey-scale images where colour is not present. This case may be treated as a colour image with only one colour plane—grey. The process is extended to more conventional colour images by treating each of the colour planes (typically red, green and blue with a commercial video camera) in all images separately. It is intended that this be generalised to an imaging system providing any number of colour planes.

The reference-white material is assumed to cover the whole field of view and is therefore available to normalise even the targets in the corners. However, some implementations of the windows may leave the targets in place, obscuring the reference-white material behind them. In this case there are two options. The first is to note that the light field, while not flat, is at least smoothly varying. By measuring the slopes at the corners in the X and Y directions it is possible to extrapolate from the visible reference-white to predict what it should look like behind the targets. This information may then be used to normalise the targets. Alternatively, the targets may be measured with the reference-white material in place and no further normalisation done. This is less accurate as the light field over the target regions may be varying. However, the targets are principally used to monitor the system stability and only provide fine tuning. Thus, provided the shape of the light field does not change dramatically in the regions of the targets, they may still be used. Changes in the light field over the whole field of view are of course detectable from the rest of the reference-white image without the corners.

Discussions of "normalisation" may be found in the patent literature for photocopiers, but the references are usually to something different. Usually, normalisation involves a single scan across a white strip internal to the unit with a line sensor, with the subsequent correction process implemented in hardware (See, e.g., U.S. Pat. No. 4,129,853 entitled "Method and Apparatus for Producing Compensated Signals for Individual Light Sensors Arranged in a Predetermined Relation," in the name of Althauser et al.; U.S. Pat. No. 5,077,605 entitled "Colour Image Reading Apparatus having Shading Correction for Plural Colour Component Signals," in the name of Ikeda, et al.; and U.S. Pat. No. 4,314,281 entitled "Shading Compensation for Scanning Apparatus," in the name of Wiggins et al.) A more sophisticated 2D approach is disclosed in U.S. Pat. No. 4,970,598 entitled "Method for Correcting Shading Effects in Video Images," in the name of Vogel, but this approach seeks to embody the correction in two orthogonal functions, one for the X axis and one for the Y axis, and implements them in hardware in a photocopier. This assumes that the light distribution has certain symmetries and is extremely limited in comparison with full pixel-by-pixel normalisation. Full pixel-by-pixel normalisation is however known in the area of image analysis. Using an image taken in one colour band to normalise an image taken in another colour band is shown in U.S. Pat. Nos. 4,170,987 and 5,363,854. Normalisation with respect to a reference material is shown in publication WO 98/37811 and in Australian Patent No. 709,459 in the name of Adriaansen et al.

Figure 23:
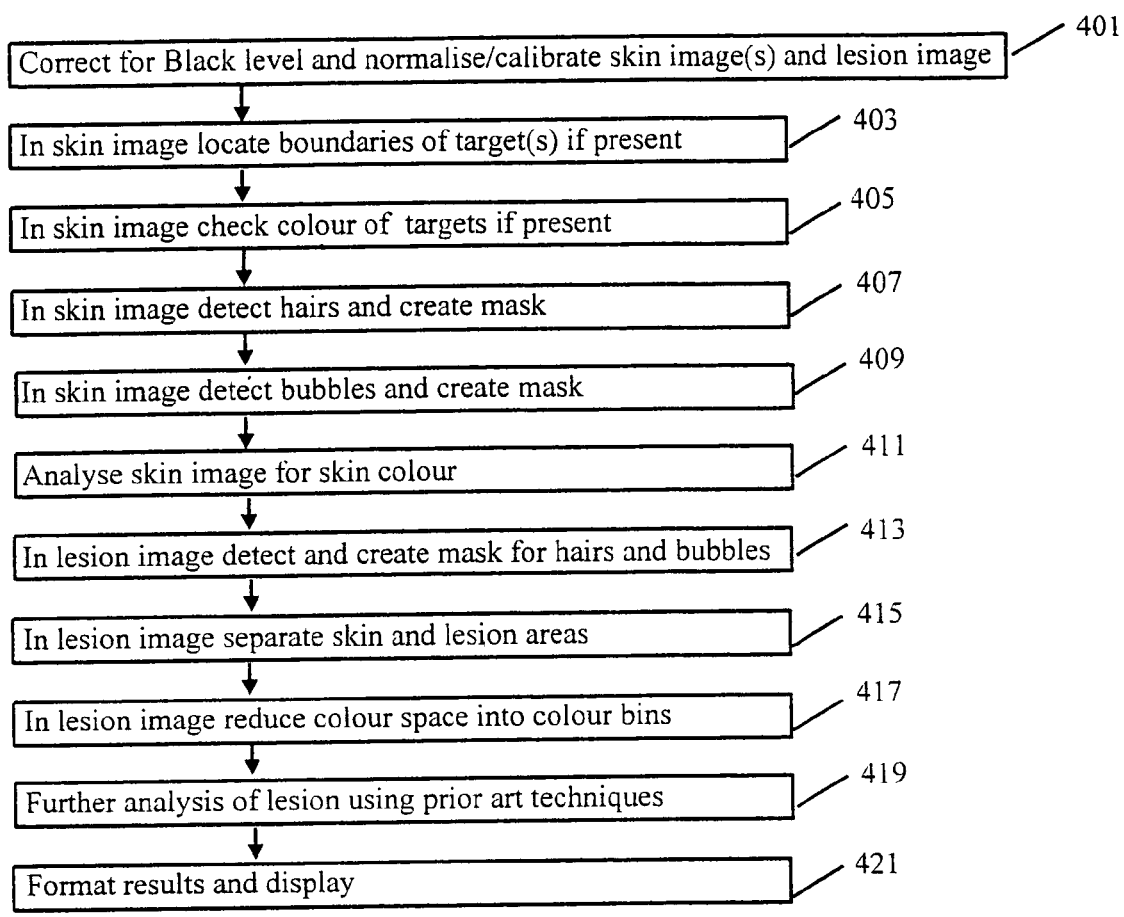
FIG. 23 is a flow chart that provides an overview of the steps in analysing a lesion image.

FIG. 23 is a flow chart illustrating broadly the steps in the analysis of a lesion image. The analysis of a lesion is not limited to the steps shown. With the passage of time and the acquisition of further images of lesions known to be either malignant or non-malignant, more knowledge about the significant characteristics of malignant melanomas will be acquired. It is expected that further research and development will enable other analyses and tests to be added to the flow chart of FIG. 23. One of the advantages of our invention is that by cataloguing and storing reproducible images, images that are reproducible from day to day and even machine to machine, a database can be developed from which better analytical routines will result.

Step 401 in FIG. 23 shows the normalisation of both the lesion image and the associated skin image. It should be noted that the image normalisation process applies when the standard cone 145 or narrow cone 203 is used, but not when the photomap cone 201 is used. A compensation step may be included here to correct the colour of the image if the colours of the targets 213–219 (FIG. 7A) indicate that this is necessary.

In step 403 the boundaries of the targets at the corners of the field of view are identified if they are present. This is determined by measuring the colour of the image in each of the four corners. If these four colours match the default colours, then the software may assume that a standard window 147 is present. If the software determines that the standard window 147 is not present, then it may check for other criteria.

Step 405 shows the colour of the targets (if present) being measured and checked against nominal values stored in the program or elsewhere in the system. If the target colours are close enough to the nominal values, then the image may be accepted as suitable for the next stage of processing; if not, then the user is advised that the system is not operating within calibration and that steps will have to be taken to rectify this problem. The option exists to re-calibrate, even if the target colours are only slightly different from their nominal values, in order to correct all pixel values in the image to bring the target colours to nominal.

It will be apparent that the processing of the images from a standard cone 145 and a narrow cone 203 to identify the targets will differ slightly. In fact, the differences in the images may be used by the software to determine which of the two cones is being used. That is, if the software determines that there is a substantial periphery of black or white around a small central circular area of colour, and the central area has a diameter matching that expected for the narrow cone, it may classify the image as having been taken with a narrow cone. On the other hand, if uniform areas of appropriate shades of grey are found just in the four corners, with a central coloured area of appropriate diameter, the system may classify the image as having been taken with the standard cone. The four colours may be all the same or may be of different values for each corner. Similarly, the use of other sized cones and windows may be detected by analysis of the image.

The targets are permanently in the field of view of the camera while both skin and lesion images are being viewed and recorded. Thus they are available in all images for the purpose of checking the calibration of the images and making any small adjustments as might be needed to correct for small colour variations. A related technique is mentioned in U.S. Pat. No. 5,016,173 in the name of Kenet et al., but there a small removable target is used for the calibration of the whole image. Full image normalisation as done here for the primary means of calibration is not included. The '173 patent also includes provision for calibrating and correcting images for aberrations, but these appear to be mainly due to the action of condensing 3D information into 2D, which does not apply here either. Another version of the target concept is described in PCT publication WO 96/05489 entitled "Colour Inspection System", in the name of Conolly et al. Here, reliance is on a small reference object of known colour in the field of view to provide an error signal or means of adjusting the camera such that subsequent images are of the correct colour, at least in the region of the reference object. Again, full image normalisation by software as done in our invention for the primary means of calibration is not contemplated.

Once an image has been identified as being of a certain type, e.g., as having been taken with a standard cone 145, the location of the targets in the corners can be obtained by image analysis. Those pixels in the corners of the image with values close to the nominal target values may be labelled as targets. Furthermore, the location of the pixels marking the transition from target to skin or lesion may be obtained by image analysis. One method of doing this is based on the use of shades of grey for the targets. Neither skin nor lesion will have a colour where all three colour values (red, green and blue) are very close together, while grey targets have this property. Identification of the target areas allows them to be subsequently excluded from processing. This exclusion may be done either by setting all excluded pixels to zero or some other predetermined value, which is then recognised by the rest of the software, or by creating a logical mask image containing a distinct flag for every pixel to be excluded and referring to this mask during processing. Further image processing, using the knowledge of the expected circular shape of the target edges, is used to determine the most likely diameter of the circle in the image and to ensure all pixels outside that circle are treated as excluded. The method for such determination may involve a least squares fit to the centre of all transition pixels, with a check to ensure that the diameter and centre so determined are reasonable for the cone previously determined to have been used for taking the image. These geometrical techniques are all prior art in image analysis.

Step 407 shows the skin image being analysed for the presence of hairs; hairs interfere with the assessment of skin properties. Those regions found to contain hairs are masked out from the skin image and excluded from further analysis. Methods for doing this are known to those skilled in the art of image analysis. The same process is applied to the lesion image, although it tends to be effective only in the skin region.

Step 409 shows the skin image being analysed for any small air bubbles left in the oil between the window and the skin. These are typically manifested by reflection highlights, often taking the local pixel values into saturation. Such areas are also excluded from further analysis. The method for removal of areas which are in saturation or very close to it are well known to those skilled in the art of image analysis, but this does not handle the full problem. When dealing with skin and lesions it may be assumed that there should be no abruptly bright regions except those due to bubbles. Accordingly, any small area or group of pixels which is significantly brighter than its immediate surroundings may be treated as a bubble and a mask created to remove it. For optical reasons the image of a bubble may be generally bright, but it will often have a dark ring around the edge of the bubble. This is due to the angles of the liquid surfaces with respect to the window, a phenomenon well known to those skilled in the art. Thus any region which has been assessed as being a bubble according to the above criterion must be checked for an abrupt dark ring. This is detected by performing a morphological gradient filter on the image and looking for strong edges associated with the bubble regions. Any area containing a strong edge with a brightness shift over a threshold is added to the previously determined bubble area.

Step 411 shows the associated skin image being analysed for colour—for average level and other statistics such as range and standard deviation.

In Step 413 the lesion image is analysed for hairs and bubbles, and these are masked out. The detection of hairs in the lesion area is more complex than over skin as the general lesion colour may more closely match that of the hairs. Therefore, a more complex algorithm is appropriate for the lesion image.

Previous attempts to automatically distinguish between skin and lesion have had limited success. One of the more successful attempts is described in *Unsupervised Color Image Segmentation with Application to Skin Tumor Borders*, Hance, et al., IEEE Engineering in Medicine and Biology, January/February 1996, pp. 104–111. Several methods are described in that paper, but the best all but one method could achieve was to separate the whole image into three colours. The fourth method used four colours by design. This is not sufficient sensitivity for melanoma diagnosis.

The problem is rendered difficult by the fact that human skin can show a wide range of colours, ranging from very pale in Northern European Caucasians to very dark brown, almost black, in Negroid races, and with other variations as found in some Asian races. Without some a priori information about the skin colour in an image, it is virtually impossible to separate skin and lesion unless there is an abrupt boundary. This is mentioned in *Computerized Evaluation of Pigmented Skin Lesion Images Recorded by a Video Microscope: Comparison between Polarizing Mode Observation and Oil/Slide Mode Observation*, Seidenari, et al., Skin Research and Technology, 1995, vol 1, pp. 187–191, where the authors write: "Borders of the lesion are automatically identified by means of edge following algorithms. In complex cases (low gradient at the border) the outline can be corrected after segmentation of the image." As many early-stage lesions and lesions on heavily tanned skin can appear to have such low-gradient boundaries, this is obviously unsatisfactory for an automated system.

Some researchers have relied on having the operator identify a region on the image which is pure skin in order for the system to have a reference point. This may be done for instance in the system in publication WO 96/16698. However, this is unsatisfactory for an automated system. For one thing, it relies on operator judgment, and different operators may pick slightly different areas and derive different results. For another thing, it assumes that there will be a significant area of clean skin in the image to serve as a reference. Images of large lesions, which are the most critical ones from the medical point of view, frequently do not have large areas of clean skin available for this purpose. There may still be a fair amount of skin in the image, but it is often scattered or broken up by the irregular shape and border of the lesion. As such irregularity is a strong indicator of malignant melanoma, these images are the most critical ones for diagnosis.

By having a separate skin image available for automated analysis, the above problems are eliminated. Additional advantages accrue with this approach. Placing a window on the patient skin can put local pressure on parts of the field of view, such that some blood is excluded from those parts. This alters the apparent colour of the skin in those parts. By having a whole image of just skin, these sorts of colour variations can also be assessed and allowed for.

Figure 24A:
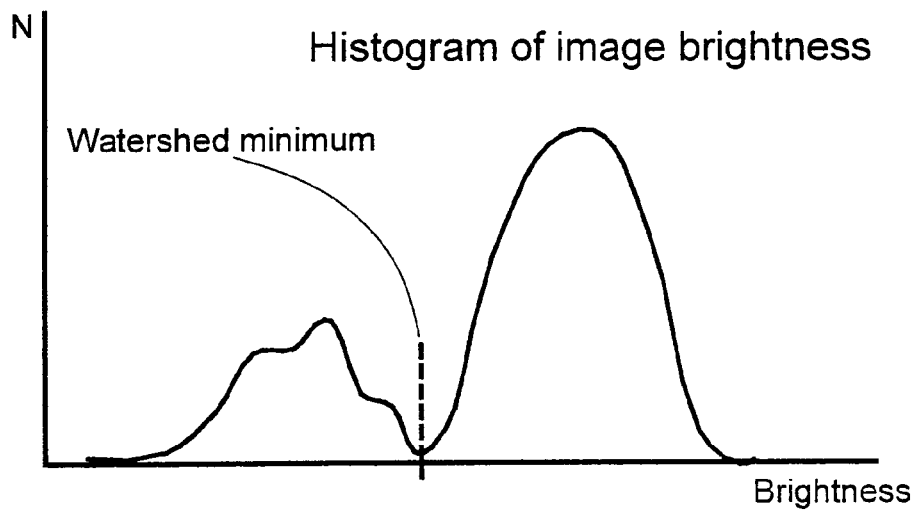
FIG. 24 illustrates two methods of image segmentation using histograms.
Figure 24B:
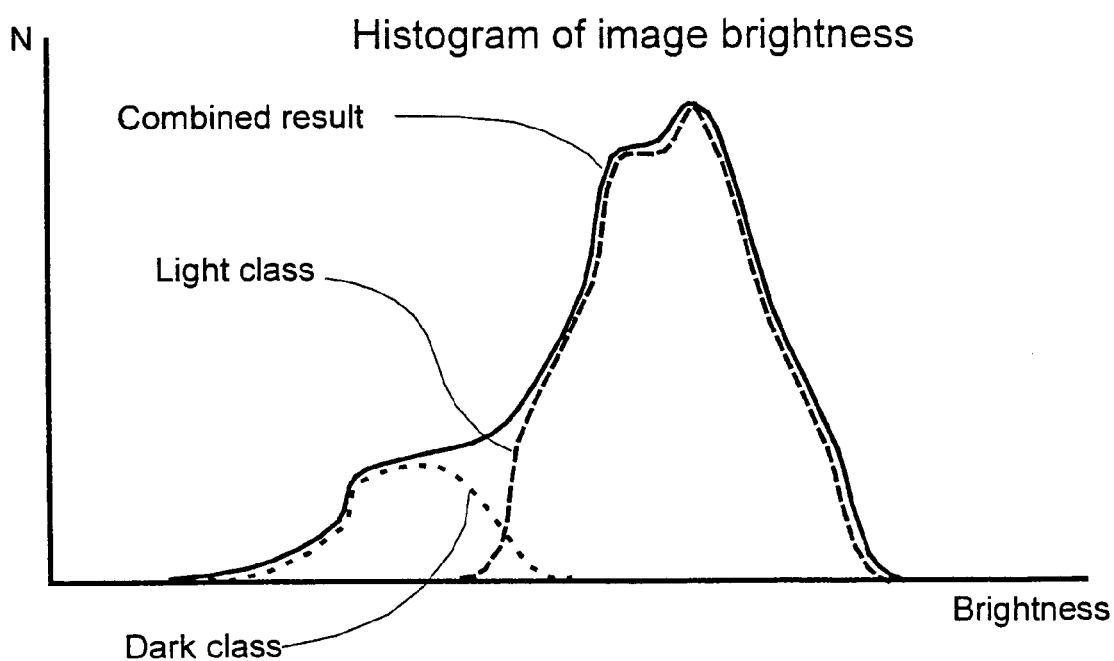

Actual distinction between skin and lesion can be done in a number of ways. The general form of this problem and methods of solution are well known to those skilled in the art of image analysis. A common method involves the creation of a histogram of colour distribution in a 2D colour space. Suitable colours here are the reds and the browns. (It is not necessary to be restricted to the red/green/blue space obtained from the camera.) The shape of the skin image histogram can be obtained and then fitted to the lesion image. Typically, a watershed will be found in the histogram between the skin colours and the lesion colours. This is illustrated in FIGS. 24A and 24B for the 1 D case of light and dark colours. The simple case of a clear watershed (or valley) is shown in FIG. 24A. Those pixels in the image with brightness less than the watershed or threshold value are put in one class (e.g., lesion) while those with brightness values greater than the watershed or threshold are put in another class (e.g., skin). The more difficult case where there is no obvious watershed is shown in FIG. 24B. In this case, it is possible to fit a known histogram shape for one class (a light class, e.g., skin) to the unknown histogram (for the lesion image) and to then subtract it. This leaves a smaller histogram representing the second class (the dark class, in this case a lesion). There is obviously some overlap. This may be resolved by simply drawing a threshold at the middle of the overlap, or more sophisticated methods may be used. An example of a more sophisticated method for deciding into which class a pixel with a value in the overlap region should be placed is to examine the surrounding areas in the image. The pixel is placed into the more common class in the surrounding areas. These methods are all known in the art.

Returning to FIG. 23, in step 415 the remaining unmasked area of the lesion image is analysed in conjunction with the skin statistics obtained in the previous step to allow a distinction to be drawn between skin and lesion. Subsequent processing then focuses solely on pixels in the lesion area, henceforth referred to as the "lesion area." The distinction is managed in the form of a mask image similar to that used for hair and bubbles.

At this stage it is appropriate to note that many digital images are rendered with one 8-bit byte for each of three colours, giving 256*256*256 possible colours. Even higher levels of resolution for each colour are possible, giving even larger numbers of possible colours. Step 417 reduces the potentially enormous number of colours present into a small number of medically significant colour bins. These bins may include such medically significant colours as red, brown, black and blue, and different boundaries of the colours used may be established by different medical experts. This step includes some degree of spatial filtering to reduce the amount of very short range speckle in the image due to electronic noise.

Step 417 then determines the area of each colour present, compares these areas with minimally significant areas also determined by medical experts, and saves the resulting list of colours and their areas found to be significantly present.

Step 419 performs image analysis on the normalised image using prior art techniques. Finally, in step 421 the results are formatted and presented on the screen of the computer monitor 107 in a form which is easy for the user to assess. The significance of each result is assessed against statistical levels established by medical experts and a total score of significance is presented to the user as a guide to the possibility that the lesion imaged is or is not a malignant melanoma.

The medical background to the colours used is as follows. The colour of pigmented skin lesions can be modelled by the number and type of blood vessels (various shades of red and blue) and the position of the pigment melanin in the skin (An Atlas of Surface Microscopy of Pigmented Skin Lesions, Menzies et al). Melanin found in the superficial component of skin is seen as black, and with increasing depth as dark brown, tan, grey and blue. Melanoma cells retain melanin pigment at many depths of skin—hence melanomas are seen as multicoloured. In addition, the highly melanoma-specific colour "blue-white veil" is found in Menzies et al, "Automated instrumentation for the diagnosis of invasive melanoma", Melanoma Research v6 1996 S47. This is due to both melanin position in combination with pathological changes in the superficial layer of skin.

Since the colours outlined above are of particular significance for medical diagnosis, care is taken to classify pixel colours into the colour ranges or bins commonly used by a skilled dermatologist. By having a skilled dermatologist identify regions of colour in many images, it is possible to set boundaries which classify pixel colours in a similar manner.

The imaging system uses three filters in the video camera, red, green and blue. The response of these filters may vary between camera manufacturers. To bring all cameras (and therefore systems of the invention) into agreement (so that data for any given lesion image will result in an image that looks the same on all systems), it is first necessary to link the RGB measurements from a given camera with some international accepted standard such as the XYZ colour system. It is known that this may be done with a linear transform (see, e.g., *Fundamentals of Image Processing*, Jain, p 67, Prentice Hall, 1989, ISBN 0-13-336165-9). This may be done using a set of uniform coloured materials as transfer standards between a calibrated calorimeter and each camera system. However, special arrangements have to be made to cater for the consequences of the previously described Total Internal Reflection effect. Suitable transfer standards may be created in two forms: as bare surfaces or as coloured materials applied to windows. A wide range of coloured materials are available for use as bare surfaces. The advantage of using a material applied to a window is that experience has shown that most coloured materials such as paint or printed surfaces can become scratched and dirty over time, and thereby change in appearance and measured properties. Also, many materials can absorb oil from skin or from residual traces of the optical coupling oil on the hand-held unit 103, and thereby change in appearance. This is unsatisfactory for a calibration system. On the other hand, a thick layer of paint or other coloured material viewed through a window is protected against mechanical damage and other contamination on the coloured surface used. Furthermore, the surface of the window is substantially flat and therefore the coloured surface being measured is also substantially flat, such that there are no variations in apparent colour due to variations in surface angle. The window material may be selected to be reasonably resistant itself against damage.

However, the two forms of coloured surfaces show different optical behaviours. A bare surface may be measured on a conventional calorimeter in the conventional manner. A surface on a window has to be measured through that window, and is therefore also subject to the TIR effect. Furthermore, if a small area window is used the amount of shift in brightness due to the TIR effect will be less at the edges of the window than in the middle. Either a reasonably large area surface and window must be used or care must be taken to make the measurement only over the central region where the influence of the edges is minimal. Since the window area is constrained in the camera system described, the latter method must be used when measuring through the window.

The advantage of doing the calorimeter measurement of the transfer standards on bare surfaces is that the ensuing camera calibration will relate the image colour as seen by the camera to the colour on a patient's bare skin as seen by a user, despite the presence of the TIR effect. The disadvantage is that the transfer standard surfaces are subject to possible damage, as described above.

The advantage of doing the calorimeter measurement of the transfer standard surfaces through the window is the greater robustness of the transfer standard. It also means that the camera calibration will then relate to the colour on a patient's skin as seen through a dermatoscope. Some but not all users will be familiar with the use of a dermatoscope. Thus it may be seen that both forms of transfer standard have value and may be used, but with different purposes. The method of handling the results is essentially the same for both forms.

Implied in the above description, and now made explicit, is that the measurement of the transfer standards on the camera system are made through a standard window with the standard index matching oil in place.

Figure 27:
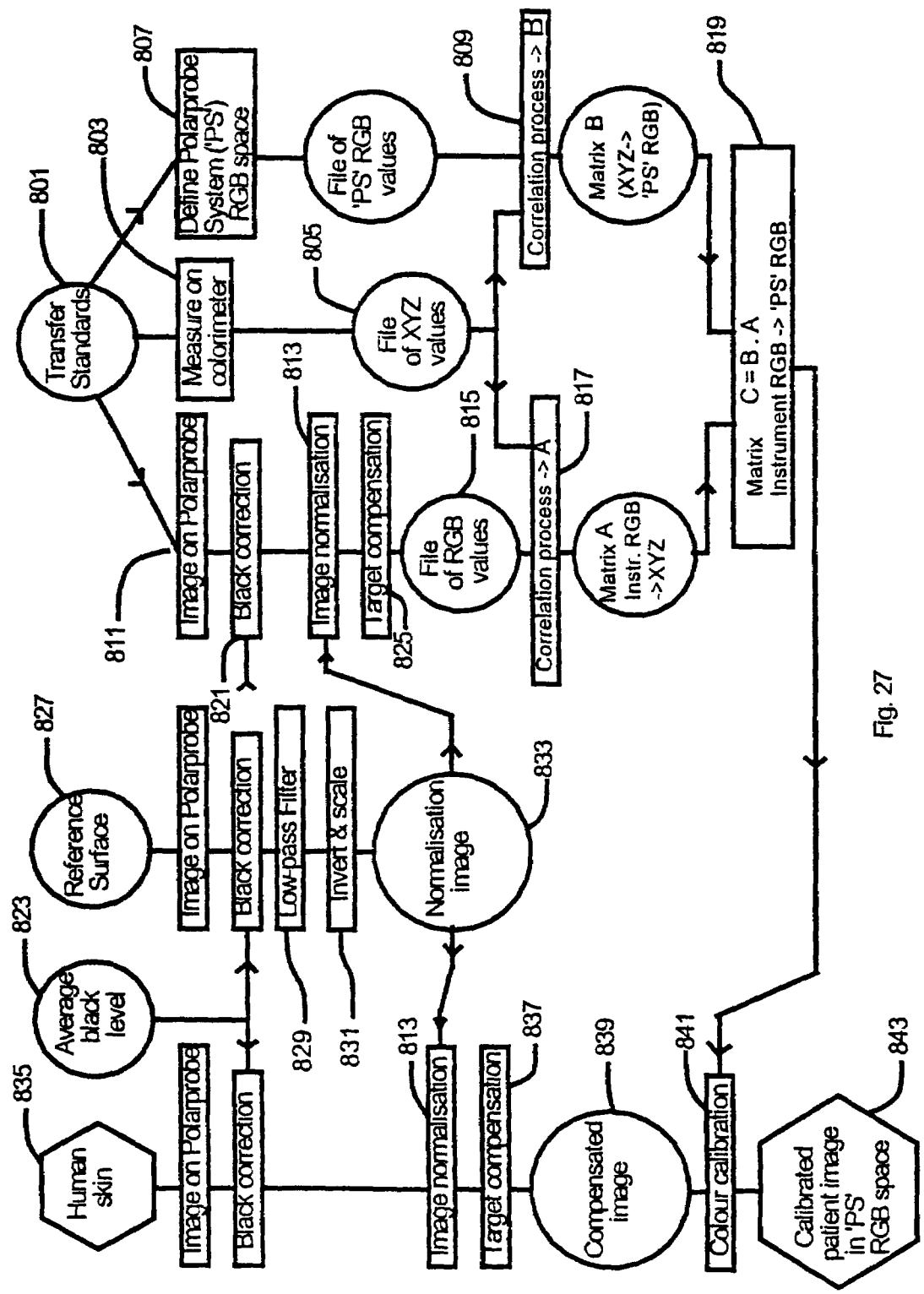
FIG. 27 is a flow chart of the colour calibration and subsequent image normalisation processes.

The full calibration process is illustrated in the flow chart in FIG. 27, and contains several parallel paths. In step 803, the transfer standards 801 are measured on a calibrated calorimeter to give a file of XYZ values 805. A Polarprobe System (the trademark used by applicants' assignee, hereinafter 'PS') RGB colour space (file) is defined in step 807 and the two are correlated in step 809 to give a conversion matrix B. This matrix defines a common RGB space in which all image processing will be done: it is then necessary to convert the images from each camera to this colour space. In practice it is advantageous to select this 'PS' RGB colour space fairly close to that normally produced by the camera 131 in order to minimise any numerical errors introduced by the conversion process.

In path 811 the transfer standards are measured (or imaged) on the camera system. All images are corrected in step 821 for the instrument black level, measured in step 823. As previously indicated this is normally set to approximately 10 units in 255. After black level correction the images are normalised in step 813 as previously described. If the targets 213–219 are present, then the images may optionally be compensated for the TIR effect as shown in step 825. This involves adjusting the images such that the targets 213–219 are at their nominal colours. From the images the average RGB values are then obtained and stored in a data file 815. This is then correlated with the file of XYZ values 805 in step 817 to give the instrument RGB-XYZ correlation matrix A.

A large number of coloured transfer standard materials 801 should preferably be used such that the equations involved in the mathematics of the correlation step 817 are over-determined. By using techniques involving a least-squares fit to the data, some elimination of the effects of noise in the measurements may be effected. Such mathematical techniques include the Generalised Matrix Inverse (see, e.g., *Generalized Inverse Methods for the Best Least-squares Solution of Systems of Non-linear Equations*, Fletcher, Computer J, vol. 10, pp. 392–399, and *GINV, A Subroutine in ANSI Fortran for Generalized Matrix Inversion*, Holdaway, Australian Computer J, vol. 9/4, November 1977) and other mathematical methods of model fitting commonly known as Hill-Climbing (see, e.g., *A rapidly convergent descent method for minimisation*, Fletcher et al., The Computer Journal, vol. 6, pp 163–8, 1964).

The values in the matrix A will in principle be unique to the camera used. Then for every camera, a matrix C=B·A may be calculated in step 819 which will allow the conversion of RGB measurements made on that camera to the equivalent values in the 'PS' RGB space.

Before a skin or lesion image is taken, the reference white surface 827 has to be imaged. This is black-corrected as shown in step 821, then is subjected to a low pass filter in step 829. This is designed to reduce the effects of electronic noise and any small surface blemishes such as spots of dirt from the image. This image is used to normalise the skin and lesion images 835, but for convenience is normally inverted and scaled in step 831 to produce a normalisation image 833. The inversion is done once on this reference white for a technical reason of computing efficiency only. The normalisation process involves applying the division operator on every pixel in every image, which is a slower operation on a computer than a multiply. By doing the inversion once beforehand, the subsequent normalisation process on all associated skin and lesion images 835 may be done with the faster multiply operator.

Skin and lesion images 835 are processed in a somewhat similar manner. Black correction is done first, as in step 821, then image normalisation is done as in step 813. Target compensation may then be done in step 837 to minimise the consequences of the TIR effect: this creates the TIR-compensated image 839. Finally, in step 841 the calibration matrix C is used to create the calibrated image 843. Although the invention has been described with reference to a particular embodiment, it is to be understood that this embodiment is merely illustrative of the application of the principles of the invention. For example, instead of storing data that pertains to individual pixel information, the data stores may contain data that pertains to information derived from the images. Thus it is to be understood that numerous modifications may be made in the illustrative embodiment of the invention and other arrangements may be devised without departing from the spirit and scope of the invention.

What we claim is:

1. A hand-held unit for facilitating the imaging of an area of a patient's skin comprising
    a hand-held case,
    a source of light inside the case for directing light toward the front of the case,
    an imaging device in the case for generating imaging signals from light derived from said area of skin, and
    at least two cones attachable to the front of said case each having
        a transparent window for bearing against an area of skin,
    each of said cones serving a different function and having properties different from the other cones, but all cones positioning their respective windows at the same distance from said imaging device.

2. A hand-held unit in accordance with claim 1 wherein at least one cone has multiple colours around its transparent window permanently in the field of view of said imaging device to aid in the calibration of said imaging device.

3. A hand-held unit in accordance with claim 2 wherein said colours are on the outside of said window so that the colours are imaged in the same plane and under the same optical conditions as the patient's skin when the window bears against the patient's skin.

4. A hand-held unit in accordance with claim 1 further including a cone attachable to the front of said case and having
    a non-transparent planar section at the front thereof whose colour is a known reproducible reference colour.

5. A hand-held unit in accordance with claim 1 wherein at least one cone is adapted to have a removable layer of a known reproducible colour attached thereto.

6. A hand-held unit in accordance with claim 5 wherein said removable layer is on said window such that upon removal it cannot be re-used.

7. A hand-held unit in accordance with claim 1 wherein at least one of said cones is adapted to permit the imaging of a lesion, and another of said cones is adapted to permit the imaging of a relatively substantial portion of the patient.

8. A hand-held unit in accordance with claim 1 wherein said source of light includes a plurality of individual light sources facing the front of the case with a diffuser in front of each of said sources.

9. A hand-held unit in accordance with claim 8 wherein said plurality of individual light sources are arranged in a plane, with each of said light sources being slightly inclined to a central axis of the hand-held unit.

10. A hand-held unit in accordance with claim 1 wherein said source of light includes a plurality of individual light sources facing the front of the case and arranged in a plane, with each of said light sources being slightly inclined to a central axis of the hand-held unit.

11. A hand-held unit in accordance with claim 9 or 10 wherein pairs of intensity distributions from said individual light sources are spatially separated such that they overlap at their half-intensity levels so that the resulting summation of their intensities has a flat central region.

12. A hand-held unit in accordance with claim 9 or 10 wherein pairs of intensity distributions from said individual light sources are spatially separated such that they satisfy the Raleigh criterion for the separation of two Gaussian pulses.

13. A hand-held unit in accordance with claim 1 wherein said source of light includes a plurality of individual light sources facing the front of the case and arranged in a plane, with pairs of intensity distributions from said individual light sources being spatially separated such that they overlap at their half-intensity levels so that the resulting summation of their intensities has a flat central region.

14. A hand-held unit in accordance with claim 13 wherein there are four individual light sources arranged at the corners of a square.

15. A hand-held unit in accordance with claim 1 wherein said source of light includes a plurality of individual light sources facing the front of the case and arranged in a plane, with said individual light sources being spatially separated such that they satisfy the Raleigh criterion for the separation of two Gaussian pulses.

16. A hand-held unit in accordance with claim 15 wherein there are four individual light sources arranged at the corners of a square.

17. A hand-held unit in accordance with claim 16 wherein said individual light sources are sufficiently separated that the reflections of each individual light source from the patient's skin or the surface of said window lie outside the field of view of said imaging device.

18. A hand-held unit in accordance with claim 1 wherein said source of light includes a plurality of individual light sources sufficiently separated that the reflections of each individual light source from the patient's skin or the surface of said window lie outside the field of view of said imaging device.

19. A hand-held unit in accordance with claim 1 wherein at least one of said cones is adapted to permit the imaging of a lesion and another of said cones is adapted to permit the imaging of a reference material, and said cones have windows of the same thickness.

20. A hand-held unit in accordance with claim 19 wherein said same thickness is at least 5 millimeters.

21. A hand-held unit for facilitating the imaging of an area of a patient's skin comprising
   a hand-held case,
   a source of light inside the case for directing light toward the front of the case,
   an imaging device in the case for generating imaging signals from light derived from said area of skin, and
   at least two different cones having different functions attachable to the front of said case each having
      a transparent window of the same thickness for bearing against an area of skin,
   said at least two different cones positioning their respective windows at the same distance from said imaging device.

22. A hand-held unit in accordance with claim 21 wherein said same thickness is at least 5 millimeters.

23. A cone for a hand-held unit that facilitates the imaging of an area of a patient's skin, said hand-held unit having
   a case,
   a source of light inside the case for directing light toward the front of the case, and
   an imaging device for generating an imaging signal from light derived from said area of skin,
   said cone having a transparent window at the front thereof with a plurality of reference targets of known colours on an outer surface that bears against the skin of a patient,
   said cone being attachable to the front of said case and having a removable reference material thereon.

24. A cone in accordance with claim 23 wherein said reference material is on said window such that upon removal it cannot be re-used.

25. A cone for a hand-held unit that facilitates the imaging of an area of a patient's skin, said hand-held unit having
   a case,
   a source of light inside the case for directing light toward the front of the case, and
   an imaging device for generating an imaging signal from light derived from said area of skin,
   said cone being attachable to the front of said case and having a transparent window at the front thereof with a plurality of reference targets of known colours on an outer surface that bears against the skin of a patient.

26. A cone for a hand-held unit that facilitates the imaging of an area of a patient's skin, said hand-held unit having
   a case,
   a source of light inside the case for directing light toward the front of the case, and
   an imaging device for generating imaging signals from light derived from said area of skin,
   said cone being attachable to the front of said case and having a transparent window at the front thereof whose thickness is at least 5 millimeters for bearing against the skin of a patient.

27. A cone in accordance with claim 26 wherein said transparent window has side edges that are absorptive and non-radiating.

28. A hand-held unit for facilitating the imaging of an area of a patient's skin comprising
   a hand-held case,
   a source of light inside the case for directing light toward the front of the case,
   an imaging device in the case for generating imaging signals from light derived from said area of skin, and
   at least two cones attachable to the front of said case each having
      a transparent window for bearing against an area of skin,
   each of said cones serving a different function and having properties different from the other cones, but all cones positioning their respective windows at the same distance from said imaging device,
   wherein at least one cone has multiple colours around its transparent window permanently in the field of view of said imaging device to aid in the calibration of said imaging device.

29. A hand-held unit in accordance with claim 28 wherein said colours are on the outside of said window so that the colours are imaged in the same plane and under the same optical conditions as the patient's skin when the window bears against the patient's skin.

30. A hand-held unit in accordance with claim 28 further including a cone attachable to the front of said case and having
a non-transparent planar section at the front thereof whose colour is a known reproducible reference colour.

31. A hand-held unit in accordance with claim 28 wherein at least one cone is adapted to have a removable layer of a known reproducible colour attached thereto.

32. A hand-held unit in accordance with claim 5 wherein said removable layer is on said window such that upon removal it cannot be re-used.

33. A hand-held unit in accordance with claim 28 wherein at least one of said cones is adapted to permit the imaging of a lesion, and another of said cones is adapted to permit the imaging of a relatively substantial portion of the patient.

34. A hand-held unit in accordance with claim 28 wherein said source of light includes a plurality of individual light sources facing the front of the case with a diffuser in front of each of said sources.

35. A hand-held unit in accordance with claim 34 wherein said plurality of individual light sources are arranged in a plane, with each of said light sources being slightly inclined to a central axis of the hand-held unit.

36. A hand-held unit in accordance with claim 28 wherein said source of light includes a plurality of individual light sources facing the front of the case and arranged in a plane, with each of said light sources being slightly inclined to a central axis of the hand-held unit.

37. A hand-held unit in accordance with claim 35 or 36 wherein pairs of intensity distributions from said individual light sources are spatially separated such that they overlap at their half-intensity levels so that the resulting summation of their intensities has a flat central region.

38. A hand-held unit in accordance with claim 35 or 36 wherein pairs of intensity distributions from said individual light sources are spatially separated such that they satisfy the Raleigh criterion for the separation of two Gaussian pulses.

39. A hand-held unit in accordance with claim 28 wherein said source of light includes a plurality of individual light sources facing the front of the case and arranged in a plane, with pairs of intensity distributions from said individual light sources being spatially separated such that they overlap at their half-intensity levels so that the resulting summation of their intensities has a flat central region.

40. A hand-held unit in accordance with claim 39 wherein there are four individual light sources arranged at the corners of a square.

41. A hand-held unit in accordance with claim 28 wherein said source of light includes a plurality of individual light sources facing the front of the case and arranged in a plane, with said individual light sources being spatially separated such that they satisfy the Raleigh criterion for the separation of two Gaussian pulses.

42. A hand-held unit in accordance with claim 41 wherein there are four individual light sources arranged at the corners of a square.

43. A hand-held unit in accordance with claim 42 wherein said individual light sources are sufficiently separated that the reflections of each individual light source from the patient's skin or the surface of said window lie outside the field of view of said imaging device.

44. A hand-held unit in accordance with claim 28 wherein said source of light includes a plurality of individual light sources sufficiently separated that the reflections of each individual light source from the patient's skin or the surface of said window lie outside the field of view of said imaging device.

45. A hand-held unit in accordance with claim 28 wherein at least one of said cones is adapted to permit the imaging of a lesion and another of said cones is adapted to permit the imaging of a reference material, and said cones have windows of the same thickness.

46. A hand-held unit in accordance with claim 45 wherein said same thickness is at least 5 millimeters.

47. A hand-held unit for facilitating the imaging of an area of a patient's skin comprising
a hand-held case,
a source of light inside the case for directing light toward the front of the case,
an imaging device in the case for generating imaging signals from light derived from said area of skin, and
at least two different cones having different functions attachable to the front of said case each having
at least one cone having a transparent window at the front thereof with a plurality of reference targets of known colours on an outer surface that bears against the skin of a patient,
said one cone being attachable to the front of said case and having a removable reference material thereon, and
said at least two different cones positioning their respective windows at the same distance from said imaging device.

48. A hand-held unit in accordance with claim 47 wherein said same thickness is at least 5 millimeters.

49. A cone for a hand-held unit that facilitates the imaging of an area of a patient's skin, said hand-held unit having
a case,
a source of light inside the case for directing light toward the front of the case, and
an imaging device for generating imaging signals from light derived from said area of skin,
said cone being attachable to the front of said case and having a transparent window at the front thereof with a plurality of reference targets of known colours on an outer surface that bears against the skin of a patient,
said cone being attachable to the front of said case and having a removable reference material thereon,
said transparent window having a thickness that is at least 5 millimeters for bearing against the skin of a patient.

50. A cone in accordance with claim 49 wherein said transparent window has side edges that are absorptive and non-radiating.

* * * * *